(12) United States Patent
Takaoka et al.

(10) Patent No.: US 8,143,404 B2
(45) Date of Patent: *Mar. 27, 2012

(54) NITROGENOUS HETEROCYLIC DERIVATIVE AND MEDICINE CONTAINING THE SAME AS AN ACTIVE INGREDIENT

(75) Inventors: Yoshikazu Takaoka, Mishima-gun (JP); Shiro Shibayama, Tsukuba (JP); Rena Nishizawa, Mishima-gun (JP)

(73) Assignee: Ono Pharmaceutical Co., Ltd, Osaka (JP)

( * ) Notice: Subject to any disclaimer, the term of this patent is extended or adjusted under 35 U.S.C. 154(b) by 1099 days.

This patent is subject to a terminal disclaimer.

(21) Appl. No.: 11/662,639

(22) PCT Filed: Sep. 12, 2005

(86) PCT No.: PCT/JP2005/017209
§ 371 (c)(1),
(2), (4) Date: Mar. 13, 2007

(87) PCT Pub. No.: WO2006/030925
PCT Pub. Date: Mar. 23, 2006

(65) Prior Publication Data
US 2008/0057074 A1 Mar. 6, 2008

(30) Foreign Application Priority Data

Sep. 13, 2004 (JP) ................................. 2004-264855
Apr. 26, 2005 (JP) ................................. 2005-127359

(51) Int. Cl.
*C07D 211/68* (2006.01)
*A61K 31/445* (2006.01)

(52) U.S. Cl. ........................................ 546/194; 514/318
(58) Field of Classification Search .................. 546/194, 546/223, 208, 210; 514/317, 318, 326
See application file for complete search history.

(56) References Cited

U.S. PATENT DOCUMENTS

| | | | |
|---|---|---|---|
| 3,375,256 A | 3/1968 | Bach et al. | |
| 5,169,855 A | 12/1992 | Cain et al. | |
| 5,486,534 A | 1/1996 | Lee et al. | |
| 6,096,780 A | 8/2000 | Shiraishi et al. | |
| 6,268,354 B1 | 7/2001 | Nishimura et al. | |
| 6,376,536 B1 | 4/2002 | Shiraishi et al. | |
| 6,515,027 B1 | 2/2003 | Bondinell et al. | |
| 6,720,321 B2 | 4/2004 | Cirillo et al. | |
| 6,765,009 B2 | 7/2004 | Francesco et al. | |
| 6,894,063 B2 | 5/2005 | Greenlee et al. | |
| 6,903,085 B1 | 6/2005 | Thom et al. | |
| 7,053,090 B2 | 5/2006 | Habashita et al. | |
| 7,071,213 B2 | 7/2006 | Friary et al. | |
| 7,247,725 B2 | 7/2007 | Butora et al. | |
| 8,003,642 B2 * | 8/2011 | Kusuda et al. ............. | 514/235.5 |
| 2002/0165223 A1 | 11/2002 | Greenlee et al. | |
| 2003/0008877 A1 | 1/2003 | Miller | |
| 2003/0069276 A1 | 4/2003 | Edlin et al. | |
| 2003/0083333 A1 | 5/2003 | Cirillo et al. | |
| 2003/0100608 A1 | 5/2003 | Cirillo et al. | |
| 2003/0114517 A1 | 6/2003 | Greenlee et al. | |
| 2003/0195192 A1 | 10/2003 | Haviv et al. | |
| 2004/0006081 A1 | 1/2004 | Burrows et al. | |
| 2004/0010013 A1 | 1/2004 | Friary et al. | |
| 2004/0082584 A1 | 4/2004 | Habashita et al. | |
| 2004/0158067 A1 | 8/2004 | Hutchison et al. | |
| 2005/0038100 A1 | 2/2005 | Greenlee et al. | |
| 2005/0215557 A1 | 9/2005 | Habashita et al. | |
| 2005/0250792 A1 | 11/2005 | Thom et al. | |
| 2005/0261325 A1 | 11/2005 | Butora et al. | |
| 2005/0267114 A1 | 12/2005 | Takaoka et al. | |
| 2005/0282861 A1 | 12/2005 | Friary et al. | |
| 2006/0178397 A1 | 8/2006 | MacDonald et al. | |

(Continued)

FOREIGN PATENT DOCUMENTS

EP 0449187 A2 10/1991

(Continued)

OTHER PUBLICATIONS

Millet et al, "Potent and Selective Farnesy/Transferase Inhibitors", J. Med. Chem., 2004, 47:6812-6820.
U.S. Office Action for U.S. Appl. No. 10/549,120 dated Feb. 13, 2009.
Extended European Search Report dated Feb. 18, 2010 in European Application No. 05785808.6-1521.
Subhash P. Khanapure et al. , "Synthesis and Structure—Activity Relationship of Novel, Highly Potent Metharyl and Methcycloalkyl Cyclooxygenase-2 (COX-2) Selective Inhibitors", Journal of Medicinal Chemistry, 2003, pp. 5484-5504, vol. 46, No. 25, American Chemical Society.

(Continued)

*Primary Examiner* — Janet Andres
*Assistant Examiner* — John Mabry
(74) *Attorney, Agent, or Firm* — Sughrue Mion, PLLC

(57) ABSTRACT

A compound represented by formula (I), a salt thereof, an N-oxide thereof, a solvate thereof or a prodrug thereof:

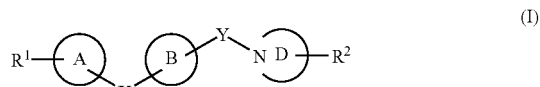

(wherein each symbol is as defined in the description.) The compounds represented by formula (I) has the antagonistic activity against CCR5, so they are useful in preventing and/or treating CCR5-related diseases, for example, various inflammatory diseases (asthma, nephritis, nephropathy, hepatitis, arthritis, rheumatoid arthritis, rhinitis, conjunctivitis, inflammatory bowel disease such as ulcerative colitis, etc.), immunological diseases (autoimmune diseases, rejection in organ transplantation (rejection of graft of solid organ, rejection of graft of pancreatic islet cells in therapy for diabetes, graft-versus-host disease, etc.), immunosuppression, psoriasis, multiple sclerosis, etc.), infectious diseases (infection with human immunodeficiency virus, acquired immunodeficiency syndrome, infection with RSV, etc.), allergic diseases (atopic dermatitis, urticaria, allergic bronchopulmonary aspergillosis, allergic eosinophilic gastroenteritis, etc.), cardiovascular diseases (arteriosclerosis, ischemic reperfusion injury, etc.), acute respiratory distress syndrome, shock accompanying bacterial infection, diabetes, cancer metastasis and so on.

3 Claims, No Drawings

U.S. PATENT DOCUMENTS

| | | | |
|---|---|---|---|
| 2006/0178399 | A1 | 8/2006 | Nishizawa et al. |
| 2007/0066624 | A1 | 3/2007 | Zhou et al. |
| 2007/0167459 | A1 | 7/2007 | Habashita et al. |
| 2007/0254886 | A1 | 11/2007 | Habashita et al. |
| 2008/0057074 | A1 | 3/2008 | Takaoka et al. |
| 2011/0152520 | A1* | 6/2011 | Takaoka et al. ............ 544/130 |

FOREIGN PATENT DOCUMENTS

| | | | |
|---|---|---|---|
| EP | 0748805 A1 | 12/1996 | |
| EP | 1020445 A1 | 7/2000 | |
| EP | 1 236 726 A1 | 9/2002 | |
| EP | 1378510 A1 | 1/2004 | |
| EP | 1422219 A1 | 5/2004 | |
| EP | 1541574 A1 | 6/2005 | |
| EP | 1604981 A1 | 12/2005 | |
| EP | 1790637 A1 | 5/2007 | |
| JP | 4-356462 A | 12/1992 | |
| JP | 2000-128782 A2 | 5/2000 | |
| JP | 2001-518505 A | 10/2001 | |
| JP | 2004-528318 A | 9/2004 | |
| JP | 2004-534787 A | 11/2004 | |
| JP | 2007-63268 A | 3/2007 | |
| RU | 2199535 C2 | 2/2003 | |
| WO | 96/10012 A1 | 4/1996 | |
| WO | 97/36903 A1 | 10/1997 | |
| WO | 99-01127 A1 | 1/1999 | |
| WO | 9917773 A1 | 4/1999 | |
| WO | 99/31062 A1 | 6/1999 | |
| WO | 99-32100 A2 | 7/1999 | |
| WO | 00/66558 A1 | 11/2000 | |
| WO | 00/66559 A1 | 11/2000 | |
| WO | 0224636 A2 | 3/2002 | |
| WO | 02053560 A1 | 7/2002 | |
| WO | 02/074758 A2 | 9/2002 | |
| WO | 02/074770 A1 | 9/2002 | |
| WO | 02/083628 A1 | 10/2002 | |
| WO | WO 02/079186 A2 | 10/2002 | |
| WO | 02/098869 A2 | 12/2002 | |
| WO | WO 03/020703 A1 | 3/2003 | |
| WO | 03-037271 A2 | 5/2003 | |
| WO | 03/066592 A1 | 8/2003 | |
| WO | 03/104230 A1 | 12/2003 | |
| WO | 2004/026873 A1 | 4/2004 | |
| WO | 2004/043925 A2 | 5/2004 | |
| WO | 2004/046110 A1 | 6/2004 | |
| WO | 2004/080966 A1 | 9/2004 | |
| WO | WO 2004/080966 A1 | 9/2004 | |
| WO | WO 2004-096131 A2 | 11/2004 | |
| WO | 2006/030925 A1 | 3/2006 | |
| WO | 2007/022371 A2 | 2/2007 | |
| WO | 2007/105637 A1 | 9/2007 | |

OTHER PUBLICATIONS

Daniel Ledniger et al., "Mammalian Antifertility Agents. IV. Basic 3,4-Dihydronaphthalenes and 1,2,3,4-Tetrahydro-1-Naphthols", 1967, pp. 79-84, vol. 10, Jounal Medicinal Chemistry.
Third Party Observations for EP 05785808.6 dated May 13, 2008.
Mashkovskiy, M.D., "Medicinal Drugs", 2001, p. 11, vol. 1, 14th Ed., S.B. Divov, Moscow.
Russian Office Action dated Jul. 9, 2009 in Russian Application No. 2007113814.
International Search Report dated Jun. 1, 2004.
Office Action, App. No. 2004800130029, Chinese Patent Office, May 11, 2007.
Office Action, App. No. 2005131833/04 (035684), Russian Patent Office, Aug. 30, 2007.
http://wordnetweb.princeton.edu/perl/webwn?s=medicament.— Definition of the term "medicament"; 1 page in total.
Singaporean Office Action dated Jan. 19, 2010 in Singapore Application No. 200806533-6.
Chinese Office Action dated Mar. 10, 2010 in Chinese application No. 200810133648.0.
Office Action issued May 11, 2010 in the counterpart Chinese Application No. 200810133649.5 of co-pending U.S. Appl. No. 10/549,120.
Office Action issued on Apr. 14, 2010 in the counterpart Russian Application No. 2007113814 of co-pending U.S. Appl. No. 10/549,120.
New Zealand Office Action dated Apr. 8, 2010 in New Zealand application No. 571019.
Vietnamese Office Action dated Jun. 10, 2010 in Vietnamese application No. 1-2005-01233.
Japanese Office Action issued May 18, 2010 in Japanese Application No. 2005-503613.
Office Action issued in European Application No. 04720257.7, dated Sep. 10, 2010.
Office Action issued in Norwegian Application No. 2005-4244, dated Sep. 23, 2010.
Office Action issued in European Application No. 05785808.6, dated Sep. 28, 2010.
Extended European Search Report issued in Application No. 07738169.7, dated Oct. 19, 2010.
Ghosh, S., et al.; "Design, synthesis and progress toward optimization of potent small molecule antagonists of CC chemokine receptor 8 (CCR8)"; Journal of Medicinal Chemistry, May 4, 2006; vol. 49 No. 9; pp. 2669 2672; XP002603811; ISSN 0022-2623.
McClellan William, et al., "Preparation of N-arylcarbonyl- and heteroarylcarbonyl benzenesulfonamide inhibitors of Bcl-Xl and Bcl-2 as promoters of apoptosis" XP002503148, Database (Online) Chemical Abstract Service, pp. 1-3, Nov. 10, 2008.
Supplementary European Search Report dated Nov. 26, 2008.
Office Action dated Oct. 19, 2010 from the Canadian Intellectual Property Office issued Canadian application No. 2,517,888, which is a foreign counterpart application to co-pending U.S. Appl. No. 10/549,120.
The Second Office Action dated Oct. 12, 2010 from The Patent Office of the People's Republic of China issued in counterpart Chinese application No. 200580038925.4.
Office Action issued Jul. 25, 2011, in counterpart Taiwanese Application No. 094131265.
U.S. Office Action dated Jun. 20, 2008 in U.S. Appl. No. 10/549,120.
U.S. Office Action dated Nov. 26, 2008 in U.S. Appl. No. 10/549,120.
U.S. Office Action dated Oct. 9, 2009 in U.S. Appl. No. 10/549,120.
European Office Action dated Dec. 15, 2009 issued in Application No. 04720257.7.
http://wordnetweb.princeton.edu/perl/webwn?s=medicament.— Definition of the term "medicament", Oct. 6, 2009.
Australian Office Action issued in Application No. 2005-283326; dated Nov. 9, 2010.

* cited by examiner

NITROGENOUS HETEROCYLIC DERIVATIVE AND MEDICINE CONTAINING THE SAME AS AN ACTIVE INGREDIENT

TECHNICAL FIELD

The present invention relates to a nitrogen-containing heterocyclic derivative which is useful as medicament and a drug containing the same as the active ingredient.

Explaining in more detail about the present invention, it relates to
(1) a compound represented by formula (I)

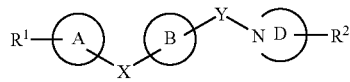

(wherein all symbols have the same meanings as described hereinafter.), a salts thereof, an N-oxide thereof or a solvate thereof, or prodrugs thereof,
(2) treatment and/or prevention for CCR5-related diseases comprising compounds represented by formula (I), a salt thereof, an N-oxide thereof or a solvate thereof, or prodrugs thereof, as an active ingredient, and
(3) a process for the preparation thereof.

BACKGROUND OF THE INVENTION

Chemokine is known as an endogeneous basic protein having leukocyte chemotactic and activating abilities and strong heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the AGM region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naive T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokine deeply takes part in the migration of such various cells. Chemokine receptors are greatly related to the control of inflammation and immune responses through a mechanism in which they are expressed at certain specified periods in variously specific cells and the effector cells are accumulated in a region where chemokine is produced.

For example, it is reported an investigation in animal models such as CCR5-knockout mouse suggesting that CCR5 as a chemokine receptor plays a significant role in rejection in organ transplantation or autoimmune disease, etc. (*Transplantation*, Vol. 72(7), 1199-1205 (2001); *Diabetes*, Vol. 51(8), 2489-2495 (2002); *Journal of Virology*, Vol. 77(1), 191-198 (2003); *Journal of Immunology*, Vol. 164(12), 6303-6312 (2000)). It is also reported which make a comparison a risk of developing several diseases and a length of the survival of the transplanted graft, etc. between a human having inactive CCR and a human having wild-type one (Ref. *The Lancet*, Vol. 357, 1758-1761 (2001); *Arthritis & Rheumatism*, Vol. 42(5), 989-992 (1999); *The Lancet*, Vol. 354, 1264-1265 (1999); *European Journal of Immunogenetics*, Vol. 29(6) 525-528 (2002)). It is suggested that CCR5 is related to several diseases, but they make no reference to the effect of drugs which antagonizes CCR in their reports.

At present, immunosuppressive treatment for diseases in transplantation area is provided. That is, a calcineurin inhibitor such as cyclosporin or tacrolimus (FK506) is used mainly with various type of an immunosuppressant agent, for example, a TOR (target of rapamycin) inhibitor such as sirolimus (rapamycin), a non-specific antiphlogistic such as corticosteroids, an antiproliferative drug such as azathioprine, mycophenolate mofetil, etc. But, it frequently causes a chronic rejection or a severe side effect, so it is desired a useful novel immunosuppressant agent which prolongs a length of the survival of the transplanted graft and reduces the side effects in comparison with existing drugs.

An antiinflammatory drug or a drug which modulates immune function such as nonsteroidal antiinflammatory drug (NSAIDs) which have an inhibitory activity against cyclooxygenase (COX), disease modifying anti-rheumatic drug (DMARDs), steroids, etc. is used for treatment for autoimmune disease or allergic diseases. The more effective a drug is, the severer a side effect caused by it is, and it is suggested that the treatment with these drugs is not an underlying remedy for the disease, but a mere symptomatic treatment.

At the same time, acquired immunodeficiency syndrome (hereinafter referred to as "AIDS") which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with *pneumocystis carinii* pneumonia and the like various opportunistic infections. Such conditions are the onset of AIDS, and it is well known that they induce and worsen Kaposi sarcoma and the like malignant tumors.

As the recent preventive and/or therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell*, 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

CCR5, which is a receptor of RANTES, MIP-1α and MIP-1β, is also used at the time of the infection with a macrophage tropic (R5) HIV (*Science*, 272, 1955 (1996)).

Accordingly, substances which can compete with CCR5 for HIV, or which can bind to HIV virus thus causing the virus unable to bind to CCR5, could become HIV infection inhibitors.

It is also reported a possibility that the CCR5 is used in the infection with Respiratory Syncytial Virus (hereinafter referred to as "RSV").

It is reported that CCR5 are expressed in arteriosclerotic plaque, so it is considered that chemokine receptor modulators are also useful in treating cardiovascular diseases.

Based on the above, it is considered that chemokine (for example, RANTES, MIP-1α (, MIP-1β, etc.) receptors, especially CCR5 are deeply related to the inflammation, immunological diseases, infectious diseases (infection with HIV, infection with RSV, etc.), and cardiovascular diseases. For example, it is considered that they are related to various inflammatory diseases (asthma, nephritis, nephropathy, hepatitis, arthritis, rheumatoid arthritis, rhinitis, conjunctivitis, inflammatory bowel disease such as ulcerative colitis, etc.), immunological diseases (autoimmune diseases, rejection in organ transplantation (rejection of graft of solid organ, rejection of graft of pancreatic islet cells in therapy for diabetes, graft-versus-host disease, etc.), immunosuppression, psoriasis, multiple sclerosis, etc.), infectious diseases (infection with human immunodeficiency virus, acquired immunodeficiency syndrome, infection with RSV, etc.), allergic diseases (atopic dermatitis, urticaria, allergic bronchopulmonary aspergillosis, allergic eosinophilic gastroenteritis, etc.), cardiovascular diseases (arteriosclerosis, ischemic reperfusion injury, etc.), acute respiratory distress syndrome, shock accompanying bacterial infection, diabetes mellitus, cancer metastasis and the like.

It is reported that the aminopiperidine derivatives represented by formula (Z)

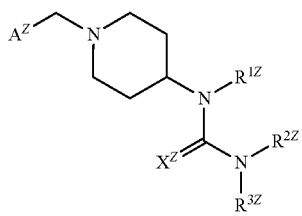

(wherein $R^{1Z}$ is hydrogen atom or C1-12 alkyl, $R^{2Z}$ and $R^{3Z}$ are each independently hydrogen atom or C1-12 alkyl, $X^Z$ is nitrogen atom or oxygen atom, AZ is

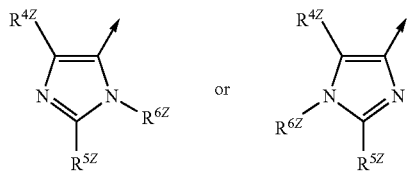

(wherein $R^{4Z}$ is hydrogen atom, C1-12 alkyl, C3-8 cycloalkyl, aryl, substituted aryl, aryl-C(=O)— or aryl-CH(OH)—, $R^{5Z}$ is hydrogen, C1-12 alkyl, C1-4 alkoxy, halogen or COR, $R^{6Z}$ is hydrogen, C1-12 alkyl or substituted C1-4 alkyl. With the proviso that the definition of each symbol is an excerpt partially.) are useful as inhibitors of the chemokine receptors (ref specification of WO02/079186).

It is described that the sulfonic acid compounds represented by formula (W)

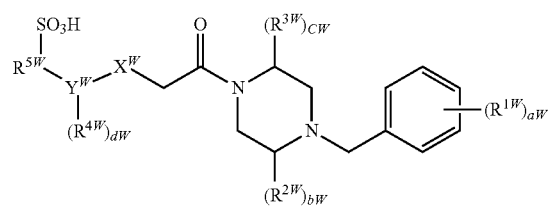

(wherein $X^W$ is —O—, —S—, —CH$_2$— or —NR$^6$—, $Y^W$ is C6-10 aryl or C2-9 heteroaryl, $R^{1W}$ is selected from the group consisting of: H—, HO—, halo-, C1-8 alkyl- optionally substituted with 1-3 fluorine atoms, etc., $R^{2W}$ and $R^{3W}$ is selected from the group consisting of: H—, oxo, C1-8 alkyl- optionally substituted with 1-3 fluorine atoms, etc., $R^{4W}$ is selected from the group consisting of: H—, HO—, halo-, NC—, etc., $R^{5W}$ is C1-8 alkyl, aW is 0-5, bW is 0-2, cW is 0-2, and dW is 0-4. With the proviso that the definition of each symbol is an excerpt partially.), pharmacological acceptable salts thereof and prodrugs thereof are selective antagonists of CCR1 (ref specification of WO02/102787).

Moreover, 1-(4-pyridyl)-piperazine derivatives are described as CCR5 antagonists (ref specification of U.S. Pat. No. 6,391,865).

On the other hand, it is reported that triazaspiro[5.5]undecane derivatives, quaternary ammonium salts thereof or N-oxides thereof, or pharmacologically acceptable salts thereof regulate the effect of chemokine/chemokine receptor, so they are used for prevention and/or treatment of various inflammatory diseases, asthma, atopic dermatitis, urticaria, allergic diseases (allergic bronchopulmonary aspergillosis or allergic eosinophilic gastroenteritis etc.), nephritis, nephropathy, hepatitis, arthritis, rheumatoid arthritis, psoriasis, rhinitis, conjunctivitis, ischemic reperfusion disorder, multiple sclerosis, ulcerative colitis, acute respiratory distress syndrome, cytotoxic shock, diabetes, autoimmune disease, in transplanted organ rejection reactions, immunosuppression, cancer metastasis and acquired immune deficiency syndrome (ref specification of WO01/40227).

It is described that the compounds represented by formula (M)

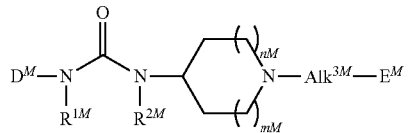

(wherein mM and nM, which are the same or different, is each zero or the integer 1 or 2, Alk$^{3M}$ is a covalent bond or a straight or branched C1-6 alkylene chain, R$^{1M}$ and R$^{2M}$, which are the same or different, is each a hydrogen atom or a straight or branched C1-6 alkyl group, D$^M$ is an optionally substituted aromatic or heteroaromatic ring group, E$^M$ is an optionally substituted C7-10 cycloalkyl, C7-10 cycloalkenyl or C7-10 polycycloaliphatic group.) are modulators of CXCR3 (ref specification of WO03/070242).

DISCLOSURE OF THE INVENTION

The compound which has the antagonistic activity against CCR5 is useful in preventing and/or treating CCR5-related diseases. Therefore it is desired that safety CCR5 antagonists are developed.

In order to find a compound which specifically binds chemokine receptor, especially CCR5, and has the antagonistic activity against it, the present inventors have conducted intensive studies and found, as a result, that the objects can be accomplished by the compound represented by formula (I), and thus the present invention has been accomplished.

The present invention relates to
1. a compound represented by formula (I)

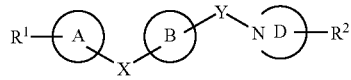

wherein R$^1$ represents (1) —N(R$^{1A}$)SO$_2$—R$^{1B}$, (2) —SO$_2$NR$^{1C}$R$^{1D}$, (3) —COOR$^{1E}$, (4) —OR$^{1F}$, (5) —S(O)$_m$R$^{1G}$, (6) —CONR$^{1H}$R$^{1J}$, (7) —NR$^{1K}$COR$^{1L}$, or (8) cyano, wherein m is 0, 1 or 2; R$^{1A}$, R$^{1B}$, R$^{1C}$, R$^{1D}$, R$^{1E}$, R$^{1F}$, R$^{1G}$, R$^{1H}$, R$^{1J}$, R$^{1K}$ and R$^{1L}$ each independently represents a hydrogen atom, a hydrocarbon group which may have a substituent(s), or a 3- to 15-membered heterocyclic group which may have a substituent(s), and wherein R$^{1C}$ and R$^{1D}$ or R$^{1H}$ and R$^{1J}$ may form a nitrogen-containing heterocyclic group which may have a substituent(s) together with a nitrogen atom to which they bind;

X and Y each independently represents a bond or a spacer containing 1 to 3 atoms as a main chain;

ring A and ring B, which are the same or different, each represents a 3- to 15-membered carbocyclic group or heterocyclic group which may have a substituent(s);

ring D is a 3- to 15-membered nitrogen-containing heterocyclic group which may have a substituent(s);

R$^2$ is (1) a hydrogen atom, (2) a hydrocarbon group which may have a substituent(s), (3) a cyano group, (4) a hydroxy group which may be protected, (5) an amino group which may have a substituent(s), (6) an oxo group, (7) a 3- to 15-membered heterocyclic group which may have a substitu- ent(s) or (8)=N—OR$^6$, wherein R$^6$ represents a hydrogen atom or C1-4 alkyl, a salt thereof, an N-oxide thereof or a solvate thereof, or a prodrug thereof;

2. the compound according to the above-described 1, wherein X and Y are each independently a bond or a divalent group comprising a combination of one or two unit(s) selected from (1) —CR$^7$R$^8$—, (2) —NR$^9$—, (3) —CO—, (4) —O—, (5) —S—, (6) —SO—, (7) —SO$_2$— and (8) —C(=N—OR$^{10}$)—, wherein R$^7$ and R$^8$ each independently represents a hydrogen atom, C1-4 alkyl, —OR$^{11}$ or phenyl, R$^9$ represents a hydrogen atom, C1-4 alkyl, or phenyl; R$^{10}$ and R$^{11}$ each independently represents a hydrogen atom or C1-4 alkyl;

3. the compound according to the above-described 2, wherein X is a bond, —O— or —CH$_2$—;

4. the compound according to the above-described 2, wherein Y is C1-2 alkylene;

5. the compound according to the above-described 1, wherein ring D is a 5- to 10-membered nitrogen-containing heterocyclic group which may have a substituent(s);

6. the compound according to the above-described 5, wherein ring D is a tropane, pyrrolidine, piperidine or azepane ring which may have a substituent(s);

7. the compound according to the above-described 6, wherein ring D is a piperidine ring which may have a substituent(s);

8. the compound according to the above-described 1, wherein ring A and ring B, which are the same or different, are each a 5- or 6-membered aromatic ring group which may have a substituent(s);

9. the compound according to the above-described 1, wherein R$^2$ is

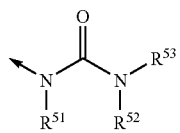

wherein the arrow represents a binding position to ring D, R$^{51}$, R$^{52}$ and R$^{53}$ each independently represents (1) a hydrogen atom, (2) a hydrocarbon group which may have a substituent(s), (3) a 3- to 15-membered heterocyclic group which may have a substituent(s), (4) a C1-4 alkoxy group which may have a substituent(s), (5) a phenoxy group which may have a substituent(s) or (6) a benzyloxy group which may have a substituent(s);

10. the compound according to the above-described 1, wherein R$^2$ is

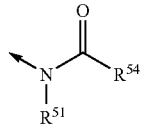

wherein the arrow represents a binding position to ring D, R$^{51}$ and R$^{54}$ each independently represents (1) a hydrogen atom, (2) a hydrocarbon group which may have a substituent(s), (3) a 3- to 15-membered heterocyclic group which may have a substituent(s), (4) a C1-4 alkoxy group which may have a substituent(s), (5) a phenoxy group which may have a substituent(s) or (6) a benzyloxy group which may have a substituent(s);

11. the compound according to the above-described 1, which is represented by formula (Ib)

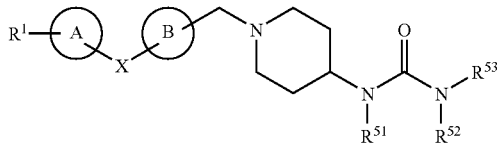

wherein all symbols have the same meanings as those described in the above-described 1 and 9;

12. the compound according to the above-described 9, wherein the hydrocarbon group which may have a substituent(s) or the 3- to 15-membered heterocyclic group which may have a substituent(s) represented by $R^{51}$ is an aromatic ring group which may have a substituent(s);

13. the compound according to the above-described 12, wherein the aromatic ring group which may have a substituent(s) is a benzene, pyrrole, imidazole, triazole, tetrazole, pyrazole, pyridine, pyrazine, pyrimidine, pyridazine, oxazole, isoxazole, thiazole, isothiazole, furazan, oxadiazole, or thiadiazole ring;

14. the compound according to the above-described 12, which is represented by formulae (Ie), (If), (Ig), or (Ih)

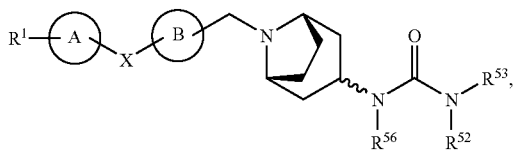

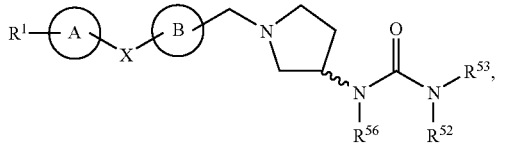

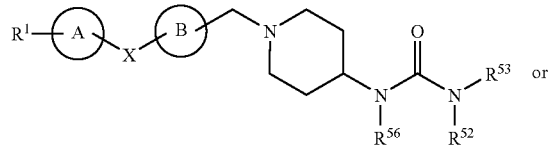

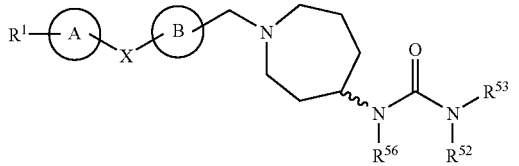

wherein symbol ⧹ represents β-configuration and symbol ⤳ represents α-configuration, β-configuration or the mixture of them; $R^{56}$ is aromatic ring group which may have a substituent(s); other symbols have the same meanings as those described in the above-described 1 and 9;

15. the compound according to the above-described 1, wherein the hydrocarbon group which may have a substituent(s) represented by $R^{51}$ is C1-15 alkyl;

16. the compound according to the above-described 15, which is selected from the group consisting of
(1) 5-({[butyl(1-{4-[4-(methylsulfonyl)phenoxy]benzyl}-4-piperidinyl)amino]carbonyl}amino)-2,4-difluorobenzamide,
(2) 5-[({butyl[1-({6-[4-(methylsulfonyl)phenoxy]-3-pyridinyl}methyl)-4-piperidinyl]amino}carbonyl)amino]-2,4-difluorobenzamide,
(3) 5-({[butyl(1-{[6-(4-{[(2-methoxyethyl)amino]carbonyl}phenoxy)-3-pyridinyl]methyl}-4-piperidinyl)amino]carbonyl}amino)-2,4-difluorobenzamide,
(4) 5-{[(butyl{1-[(6-{4-[(ethylsulfonyl)amino]phenoxy}-3-pyridinyl)methyl]-4-piperidinyl}amino)carbonyl]amino}-2,4-difluorobenzamide,
(5) 5-{[(butyl{1-[(6-{2-methyl-4-[(methylsulfonyl)amino]phenoxy}-3-pyridinyl)methyl]-4-piperidinyl}amino)carbonyl]amino}-2-chloro-4-fluorobenzamide,
(6) 2-(5-{[(butyl{1-[(6-{4-[(methylsulfonyl)amino]phenoxy}-3-pyridinyl)methyl]-4-piperidinyl}amino)carbonyl]amino}-2,4-difluorophenyl)acetamide,
(7) 5-[({butyl[1-(4-{4-[(methylsulfonyl)amino]phenoxy}benzyl)-4-piperidinyl]amino}carbonyl)amino]-2,4-difluoro-N-methylbenzamide,
(8) 5-{[(butyl{1-[(6-{4-[(methylsulfonyl)amino]phenoxy}-3-pyridinyl)methyl]-4-piperidinyl}amino)carbonyl]amino}-2,4-difluorobenzamide, and
(9) 5-[({butyl[1-(4-{4-[(methylamino)sulfonyl]phenoxy}benzyl)-4-piperidinyl]amino}carbonyl)amino]-2,4-difluorobenzamide;

17. the compound according to the above-described 12, wherein the aromatic ring group represented by $R^{51}$ is a mono-carbocyclic group or mono-heterocyclic group which have aromaticity;

18. the compound according to the above-described 17, which is selected from the group consisting of
(1) N-(4-{[5-({4-[{[(4-fluorophenyl)amino]carbonyl}(phenyl)amino]-1-piperidinyl}methyl)-2-pyridinyl]oxy}-3-methoxyphenyl)methanesulfonamide,
(2) N-(4-{[5-({4-[{[(4-fluorophenyl)amino]carbonyl}(phenyl)amino]-1-piperidinyl}methyl)-2-pyridinyl]oxy}phenyl)methanesulfonamide,
(3) N-(4-{[5-({4-[{[(4-fluorophenyl)amino]carbonyl}(3-thienyl)amino]-1-piperidinyl}methyl)-2-pyridinyl]oxy}phenyl)methanesulfonamide,
(4) N-[4-({5-[(4-{3-thienyl[(3-thienylamino)carbonyl]amino}-1-piperidinyl)methyl]-2-pyridinyl}oxy)phenyl] methane sulfonamide,
(5) 2-fluoro-5-({[{1-[(6-{4-[(methylsulfonyl)amino]phenoxy}-3-pyridinyl)methyl]-4-piperidinyl}(phenyl)amino]carbonyl}amino)benzamide,
(6) N-{4-[4-({4-[{[(4-fluorophenyl)amino]carbonyl}(phenyl)amino]-1-piperidinyl}methyl)-3,5-dimethyl-1H-pyrazol-1-yl]phenyl}methanesulfonamide,
(7) 4-[4-({4-[{[(4-fluorophenyl)amino]carbonyl}(phenyl)amino]-1-piperidinyl}methyl)-3,5-dimethyl-1H-pyrazol-1-yl]-N-[2-(4-morpholinyl)ethyl]benzenesulfonamide,
(8) N-(4-{[5-({4-[{[(2,4-difluorophenyl)amino]carbonyl}(3-thienyl)amino]-1-piperidinyl}methyl)-2-pyridinyl]oxy}phenyl)methanesulfonamide,
(9) 2-chloro-N-methyl-5-({[{1-[(6-{4-[(methylsulfonyl)amino]phenoxy}-3-pyridinyl)methyl]-4-piperidinyl}(phenyl)amino]carbonyl}amino)benzamide,
(10) N-(4-{[5-({4-[({[4-chloro-3-(4-morpholinylcarbonyl)phenyl]amino}carbonyl)(phenyl)amino]-1-piperidinyl}methyl)-2-pyridinyl]oxy}phenyl)methanesulfonamide,

(11) 2-fluoro-5-{[((3-fluorophenyl){1-[(6-{4-[(methylsulfonyl)amino]phenoxy}-3-pyridinyl)methyl]-4-piperidinyl}amino)carbonyl]amino}benzamide,
(12) N-(3-fluorophenyl)-N'-(6-methyl-3-pyridinyl)-N-[1-({6-[4-(methylsulfonyl)phenoxy]-3-pyridinyl}methyl)-4-piperidinyl]urea,
(13) 2-[4-({4-[[({4-fluoro-3-[(methylsulfonyl)amino]phenyl}amino)carbonyl](phenyl)amino]-1-piperidinyl}methyl)phenoxy]-5-[(methylsulfonyl)amino]benzamide,
(14) 2-fluoro-N-methyl-5-({[{1-[(6-{4-[(methylsulfonyl)amino]phenoxy}-3-pyridinyl)methyl]-4-piperidinyl}(phenyl)amino]carbonyl}amino)benzamide,
(15) 2-fluoro-N-methyl-5-({[[1-({6-[4-(methylsulfonyl)phenoxy]-3-pyridinyl}methyl)-4-piperidinyl](phenyl)amino]carbonyl}amino)benzamide,
(16) 2-[4-({4-[({[3-(acetylamino)-4-fluorophenyl]amino}carbonyl)(phenyl)amino]-1-piperidinyl}methyl)phenoxy]-5-[(methylsulfonyl)amino]benzamide,
(17) N-(4-{[5-({4-[{[(6-methyl-3-pyridinyl)amino]carbonyl}(phenyl)amino]-1-piperidinyl}methyl)-2-pyridinyl]oxy}phenyl)methanesulfonamide,
(18) N-[2-fluoro-5-({[{1-[(6-{4-[(methylsulfonyl)amino]phenoxy}-3-pyridinyl)methyl]-4-piperidinyl}(phenyl)amino]carbonyl}amino)phenyl]acetamide,
(19) N-{4-[(5-{[4-((3-fluorophenyl){[(6-methyl-3-pyridinyl)amino]carbonyl}amino)-1-piperidinyl]methyl}-2-pyridinyl)oxy]phenyl}methanesulfonamide, and
(20) N'-(4-fluorophenyl)-N-[1-({6-[4-(methylsulfonyl)phenoxy]pyridin-3-yl}methyl)piperidin-4-yl]-N-phenylurea;
19. the compound according to the above-described 11, which is selected from a group the group consisting of:
(1) 2-fluoro-5-({[{1-[(6-{4-[(methylsulfonyl)amino]phenoxy}-3-pyridinyl)methyl]-4-piperidinyl}(phenyl)amino]carbonyl}amino)benzamide,
(2) N-(4-{[5-({4-[{[(6-methyl-3-pyridinyl)amino]carbonyl}(phenyl)amino]-1-piperidinyl}methyl)-2-pyridinyl]oxy}phenyl)methanesulfonamide,
(3) N-[2-fluoro-5-({[{1-[(6-{4-[(methylsulfonyl)amino]phenoxy}-3-pyridinyl)methyl]-4-piperidinyl}(phenyl)amino]carbonyl}amino)phenyl]acetamide, and
(4) N-{4-[(5-{[4-((3-fluorophenyl){[(6-methyl-3-pyridinyl)amino]carbonyl}amino)-1-piperidinyl]methyl}-2-pyridinyl)oxy]phenyl}methanesulfonamide;
20. the compound according to the above-described 11, which is selected from the group consisting of:
(1) 5-[({butyl[1-(4-{2-methyl-4-[(methylsulfonyl)amino]phenoxy}benzyl)-4-piperidinyl]amino}carbonyl)amino]-2,4-difluorobenzamide,
(2) N-(4-{[5-({4-[{[(2,4-difluorophenyl)amino]carbonyl}(phenyl)amino]-1-piperidinyl}methyl)-2-pyridinyl]oxy}-3-methoxyphenyl)methanesulfonamide,
(3) N-(4-{[5-({4-[{[(4-methylphenyl)amino]carbonyl}(phenyl)amino]-1-piperidinyl}methyl)-2-pyridinyl]oxy}phenyl)methanesulfonamide,
(4) N-(4-{[5-({4-[{[(4-chlorophenyl)amino]carbonyl}(phenyl)amino]-1-piperidinyl}methyl)-2-pyridinyl]oxy}phenyl)methanesulfonamide, and
(5) N-(4-{[5-({4-[{[(4-fluorophenyl)amino]carbonyl}(phenyl)amino]-1-piperidinyl}methyl)-2-pyridinyl]oxy}phenyl)acetamide;
21. the compound according to the above-described 1, which is selected from the group consisting of:
(1) 2-fluoro-5-({[{1-[(6-{4-[(methylsulfonyl)amino]phenoxy}-3-pyridinyl)methyl]-4-piperidinyl}(phenyl)amino]carbonyl}amino)benzamide,
(2) N-(4-{[5-({4-[{[(6-methyl-3-pyridinyl)amino]carbonyl}(phenyl)amino]-1-piperidinyl}methyl)-2-pyridinyl]oxy}phenyl)methanesulfonamide dihydrochloride,
(3) N-[2-fluoro-5-({[{1-[(6-{4-[(methylsulfonyl)amino]phenoxy}-3-pyridinyl)methyl]-4-piperidinyl}(phenyl)amino]carbonyl}amino)phenyl]acetamide hydrochloride,
(4) N-{4-[(5-{[4-((3-fluorophenyl){[(6-methyl-3-pyridinyl)amino]carbonyl}amino)-1-piperidinyl]methyl}-2-pyridinyl)oxy]phenyl}methanesulfonamide dihydrochloride,
(5) 5-[({butyl[1-(4-{2-methyl-4-[(methylsulfonyl)amino]phenoxy}benzyl)-4-piperidinyl]amino}carbonyl)amino]-2,4-difluorobenzamide hydrochloride,
(6) N-(4-{[5-({4-[{[(2,4-difluorophenyl)amino]carbonyl}(phenyl)amino]-1-piperidinyl}methyl)-2-pyridinyl]oxy}-3-methoxyphenyl)methanesulfonamide hydrochloride,
(7) N-(4-{[5-({4-[{[(4-methylphenyl)amino]carbonyl}(phenyl)amino]-1-piperidinyl}methyl)-2-pyridinyl]oxy}phenyl)methanesulfonamide,
(8) N-(4-{[5-({4-[{[(4-chlorophenyl)amino]carbonyl}(phenyl)amino]-1-piperidinyl}methyl)-2-pyridinyl]oxy}phenyl)methanesulfonamide, and
(9) N-(4-{[5-({4-[{[(4-fluorophenyl)amino]carbonyl}(phenyl)amino]-1-piperidinyl}methyl)-2-pyridinyl]oxy}phenyl)acetamide hydrochloride;
22. a pharmaceutical composition, which comprises the compound according to the above-described 1, a salt thereof, an N-oxide thereof, a solvate thereof, or a prodrug thereof;
23. the pharmaceutical composition according to the above-described 22, which is a chemokine receptor antagonist;
24. the pharmaceutical composition according to the above-described 23, which is a CCR5 antagonist;
25. the pharmaceutical composition according to the above-described 24, which is an agent for treatment and/or prevention for a CCR5-related disease;
26. the pharmaceutical composition according to the above-described 25, wherein the CCR5-related disease is infectious diseases, immunological diseases, inflammatory diseases and/or cardiovascular diseases;
27. the pharmaceutical composition according to the above-described 26, wherein the CCR5-related disease is infection with human immunodeficiency virus, acquired immunodeficiency syndrome, infection with Respiratory Syncytial Virus, rejection in organ transplantation, multiple sclerosis, inflammatory bowel disease, and/or asthma;
28. the pharmaceutical composition according to the above-described 26, wherein the immunological diseases is rejection in organ transplantation;
29. the pharmaceutical composition according to the above-described 22, which is an agent for prevention and/or treatment for infectious diseases, immunological diseases, inflammatory diseases and/or cardiovascular diseases;
30. a medicament comprising a combination of the compound represented by formula (I) according to the above-described 1, a salt thereof, an N-oxide thereof, a solvate thereof, or a prodrug thereof, and one or more agent(s) selected from a reverse transcriptase inhibitor, a protease inhibitor, an integrase inhibitor, a CCR2 antagonist, a CCR3 antagonist, a CCR4 antagonist, a CCR5 antagonist, a CXCR3 antagonist, a CXCR4 antagonist, a fusion inhibitor, an antibody against a surface antigen of HIV, and a vaccine of HIV;
31. a medicament comprising a combination of the compound represented by formula (I) according to the above-described 1, a salt thereof, an N-oxide thereof, a solvate thereof, or a prodrug thereof, and one or more agent(s) selected from an immunosuppressant agent, a nonsteroidal antiinflammatory drug, a disease modifying anti-rheumatic drug, steroids, an antiinflammatory enzyme preparations, a chondroprotective agents, a T-cell inhibitor, a TNFα inhibitor, a prostaglandin synthase inhibitor, an IL-1 inhibitor, an IL-6 inhibitor, an interferon gamma agonist, prostaglandins, a phosphodiesterase inhibitor, and a metalloproteinase inhibitor;

32. a method for preventing or treating a CCR5-related disease in a mammal, which comprises administering to a mammal an effective amount of a compound represented by formula (I) according to the above-described 1, a salt thereof, an N-oxide thereof, a solvate thereof, or a prodrug thereof;

33. use of a compound represented by formula (I) according to the above-described 1, a salt thereof, an N-oxide thereof, a solvate thereof, or a prodrug thereof for the manufacture of an agent for prevention and/or treatment of a CCR5-related disease;

34. a pharmaceutical composition according to the above-described 22, which is an inhibitor of cell migration; and 35. a process for preparation of the compound represented by formula (I) according to the above-described 1, a salt thereof, an N-oxide thereof or a solvate thereof, or a prodrug thereof.

The "hydrocarbon group" in the "hydrocarbon group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$ includes, for example, (a) C1-15 alkyl such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl etc.; (b) C3-8 cycloalkyl such as cyclopropyl, cyclobutyl, cyclopentyl, cyclohexyl etc.; (c) C2-10 alkenyl such as vinyl, allyl, 2-methylallyl, 2-butenyl, 3-butenyl, 3-octenyl etc.; (d) C2-10 alkynyl such as ethynyl, 2-propynyl, 3-hexynyl etc.; (e) C3-10 cycloalkenyl such as cyclopropenyl, cyclopentenyl, cyclohexenyl etc.; (f) C6-14 aryl such as phenyl, naphthyl etc., (g) C7-16 aralkyl such as benzyl, phenylethyl etc.; (h) (C3-8 cycloalkyl)-(C1-4 alkyl) such as cyclohexylmethyl, cyclohexylethyl, cyclohexylpropyl, 1-methyl-1-cyclohexylmethyl, cyclopropylethyl etc.

The "3- to 15-membered heterocycle" in the "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$ includes a "3- to 15-membered unsaturated heterocycle" or a "3- to 15-membered saturated heterocycle".

The "3- to 15-membered unsaturated heterocycle" includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, dihydroacridine, tetrahydroacridine, dihydrodibenzofuran, dihydrodibenzothiophene, tetrahydrodibenzofuran, tetrahydrodibenzothiophene, dioxaindan, benzodioxane, chroman, benzodithiolane, benzodithiane etc.

The "3- to 15-membered saturated heterocycle" includes, for example, aziridine, azetidine, azocane, pyrrolidine, imidazolidine, triazolidine, tetrazolidine, pyrazolidine, piperidine, piperazine, perhydropyrimidine, perhydropyridazine, azepane (perhydroazepine), perhydrodiazepine, oxirane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine, perhydrodibenzofuran, perhydrodibenzothiophene, dioxolane, dioxane, dithiolane, dithiane,

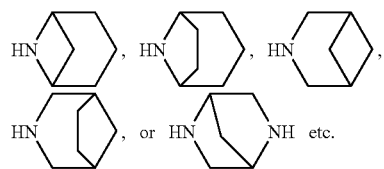

The "substituents" in the "hydrocarbon group which may have a substituent(s)" or 3- to 15-membered heterocyclic group represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$ include, for example, (1) nitro, (2) hydroxy group, (3) oxo, (4) thioxo, (5) cyano, (6) carbamoyl, (7) aminocarbonyl substituted by C1-8 hydrocarbon substituted by one or two substituent(s) selected from (a) hydroxyl, (b) amino, (c) C1-4 alkoxy, (d) mono- or disubstituted amino substituted by C1-8 hydrocarbon group, etc., (e) carboxyl, (f) C1-6 alkoxy-carbonyl etc. (e.g., N-methylaminocarbonyl, N-ethylaminocarbonyl, N-propylaminocarbonyl, N-butylaminocarbonyl, N-cyclohexylmethylaminocarbonyl, N,N-dimethylaminocarbonyl, N-butyl-N-cyclohexylmethylaminocarbonyl, N-cyclohexylaminocarbonyl, phenylaminocarbonyl, N-(2-methoxyethyl)aminocarbonyl, N-(2-hydroxyethyl)aminocarbonyl, N-(2-aminoethyl)aminocarbonyl, N-[2-(N',N'-dimethylamino)ethyl]aminocarbonyl, N-(2-carboxyethyl)aminocarbonyl, N-(2-methoxycarbonylethyl)aminocarbonyl, etc.), (8) carboxy, (9) C1-6 alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl, etc., (10) sulfo, (11) halogen such as fluorine, chlorine, bromine or iodine, (12) C1-6 alkoxy which may be substituted by halogen (e.g., methoxy, ethoxy, propoxy, isopropoxy, butoxy, isobutoxy, sec-butoxy, tert-butoxy, difluoromethoxy or trifluoroethoxy), (13) phenoxy, (14) halogenophenoxy such as o-, m- or p-chlorophenoxy, or o-, m- or p-bromophenoxy etc., (15) C1-6 alkylthio such as methylthio, ethylthio, propylthio, isopropylthio, butylthio, tert-butylthio etc., (16) phenylthio, (17) C1-6 alkylsulfinyl such as methylsulfinyl ethylsulfinyl, propylsulfinyl, butylsulfinyl, etc., (18) C1-6 alkylsulfonyl such as methylsulfonyl or ethylsulfonyl, propylsulfonyl, butylsulfonyl, etc., (19) amino, (20) C1-6 lower acylamino such as acetylamino or propionylamino etc., (21) mono- or disubstituted amino substituted by hydrocarbon group (the "hydrocarbon group" has the same meanings as above "hydrocarbon group" and may be substituted by oxo, amino which may be substituted by optional substituents (e.g., hydrocarbon), carbamoyl, halogen or hydroxy group etc.) (e.g., methylamino, ethylamino, propylamino, isopropylamino, butylamino, dimethylamino, diethylamino, cyclohexylamino, 1-carbamoyl-2-cyclohexylethylamino, N-butyl-N-cyclohexylmethylamino or phenylamino etc.), (22) C1-8 alkanoyl such as formyl or acetyl, propionyl, butyryl, isobutyryl, cyclohexylcarbonyl, etc., (23) C6-10 aryl-C1-4 lower acyl such as benzoyl, benzylcarbonyl, (24) 3- to 15-membered heterocyclic group, which includes 1 to 4 hetero atoms selected from oxygen, sulfur and nitrogen besides carbon atom, and optionally has 1 to 4 substituents selected from (a) halogen such as bromine, chlorine, or fluorine, (b) hydrocarbon optionally substituted by oxo or hydroxy group etc., (the "hydrocarbon group" has the same meanings as above "hydrocarbon group") such as methyl, ethyl, propyl, isopropyl, benzyl, cyclohexyl, cyclohexylmethyl or cyclohexylethyl etc., (c) halogenophenoxy such as o-, m- or p-chlorophenoxy, or o-, m- or p-bromophenoxy etc., and (d) oxo etc., such as thienyl, furyl, pyrazolyl, tetrahydropyranyl, thiazolyl, isothiazolyl, oxazolyl, isoxazolyl, imidazolyl, triazolyl, tetrazolyl, pyridyl, pyromidinyl, pyridazinyl, quinolyl, isoquinolyl, indolyl, aziridinyl, azetidinyl, pyrrolidinyl, pyrrolinyl, pyrrolyl, imidazolidinyl, piperidino, morpholino, dihydropyridyl, N-methylpiperazinyl, N-ethylpiperazinyl etc., (25) C1-10 haloalkyl such as difluoromethyl, trifluoromethyl, trifluoroethyl, chloromethyl, dichloromethyl, or trichloroethyl etc., (26) hydroxyimino, (27) alkyloxyimino such as methyloxyimino or ethyloxyimino etc., (28) alkylsulfonylamino such as methylsulfonylamino, ethylsulfonylamino or benzylsulfonylamino etc., or (29) arylsulfonylamino such as phenylsulfonylamino or p-toluenesulfonylamino etc., (30) cyclic aminocarbonyl such as 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl etc., (31) C1-8 hydrocarbon group substituted by 1 or 2 substituents selected from (a) hydroxy, (b) amino, (c) C1-4 alkoxy, (d) mono- or disubstituted amino substituted by C1-8 hydrocarbon group, etc., (e) aminocarbonyl substituted by C1-8 hydrocarbon group, etc. which may have a substituent(s) (This substituents are selected from, for example, (a) hydroxy, (b) amino, (c) C1-4 alkoxy, (d) mono- or disubstituted amino substituted by C1-8 hydrocarbon group, etc., (e) carboxy, (f) C1-6 alkoxy-carbonyl, and may have 1 or 2 group(s).), such as hydroxymethyl, hydroxyethyl, aminomethyl, methoxymethyl, N,N-dimethylaminomethyl, carbamoylmethyl, N-methylaminocarbonylmethyl, N,N-dimethylaminocarbonylmethyl, etc., (32) (C1-4 alkoxy)-(C1-4 alkyl) group such as methoxyethyl etc., (33) C1-8 alkanoyloxy group such as formyloxy, acetyloxy, propyonyloxy, butyryloxy, isobutyryloxy or cyclohexylcarbonyloxy etc., or benzoyloxy group, (34) amidino group, (35) imino group, (36) C1-8 alkanoylamide group such as formamide, acetamide, trifluoroacetamide, propionylamide, butyrylamide, isobutyrylamide, cyclohexylcarbonylamino etc., (37) benzamide group, (38) carbamoylamino group, (39) N—C1-4 alkylcarbamoylamino group such as N-methylcarbamoylamino, N-ethylcarbamoylamino, N-propylcarbamoylamino, N-isopropylcarbamoylamino, N-butylcarbamoylamino etc., (40) N,N-di-C1-4 alkylcarbamoylamino group such as N,N-dimethylcarbamoylamino, N,N-diethylcarbamoylamino, N,N-dipropylcarbamoylamino, N,N-dibutylcarbamoylamino etc., (41) C1-3 alkylenedioxy group such as methylenedioxy or ethylenedioxy etc., (42) —B(OH)$_2$, (43) epoxy group, (44) mercapto group, (45) sulfino group, (46) phosphono group, (47) sulfamoyl group, (48) C1-6 monoalkylsulfamoyl such as N-methylsulfamoyl, N-ethylsulfamoyl, N-propylsulfamoyl, N-isopropylsulfamoyl or N-butylsulfamoyl etc., (49) di-C1-4 alkylsulfamoyl group such as N,N-dimethylsulfamoyl, N,N-diethylsulfamoyl, N,N-dipropylsulfamoyl or N,N-dibutylsulfamoyl etc., (50) phenylsulfinyl group, (51) phenylsulfonyl group, (52) azide group, or (53) hydrocarbon group (This "hydrocarbon group" have the same meanings as the above-described "hydrocarbon group", for example, methyl, ethyl, propyl, isopropyl, vinyl, ethynyl, cyclohexenyl, phenyl, naphthyl, benzyl, cyclohexyl, cyclohexylmethyl, cyclohexylethyl, etc.). The "hydrocarbon group which may have a substituent(s)" or "3- to 15-membered heterocyclic group which may have a substituent(s)" can have 1 to 10 of substituents selected from above (1) to (53). When the number of substituents is two or more, each substituent may be same or different.

The "nitrogen-containing heterocyclic group" in the "nitrogen-containing heterocyclic group which may have a substituent(s)" formed by $R^{1C}$ and $R^{1D}$ or $R^{1H}$ and $R^{1J}$ together with a nitrogen atom to which they bind include, for example, aziridine, azetidine, pyrroline, pyrrolidine, imidazoline, imidazolidine, dihydropyridine, tetrahydropyridine, piperidine, dihydropyrazine, tetrahydropyrazine, piperazine, perhydropyrimidine, perhydropyridazine, tetrahydroazepine, azepane (perhydroazepine), tetrahydrodiazepine, perhydrodiazepine, tetrahydrooxazole (oxazolidine), tetrahydrothiazole (thiazolidine), tetrahydrooxazine, perhydrooxazepine, tetrahydrothiazine, perhydrothiazepine, morpholine, thiomorpholine ring, etc.

The "substituents" in the "nitrogen-containing heterocyclic group which may have a substituent(s)" formed by $R^{1C}$ and $R^{1D}$ or $R^{1H}$ and $R^{1J}$ together with a nitrogen atom to which they bind include have the same meanings as the "substituents" in the "hydrocarbon group which may have a substituent(s)" or "3- to 15-membered heterocyclic group which may have a substituent(s)" has the same meaning as the "hydrocarbon group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$.

The "spacer containing 1 to 3 atoms as a main chain" represented by X and Y means a space formed by 1 to 3 continued atoms of a main chain. In this case, the "number of atoms as a main chain" should be counted such that the number of atoms as a main chain becomes minimized. The "spacer having from 1 to 3 atoms as a main chain" include, for example, a bivalent group comprising 1 to 3 selected from —$CR^7R^8$—, —$NR^9$—, —CO—, —O—, —S—, —SO—, —$SO_2$— and —$C(=N—OR^{10})$— (wherein $R^7$ and $R^8$ are each independently hydrogen atom, C1-4 alkyl, —$OR^{11}$ or phenyl, $R^9$ is hydrogen atom, C1-4 alkyl or phenyl, $R^{10}$ and $R^{11}$ are each independently hydrogen atom or C1-4 alkyl.). In the case, the "C1-4 alkyl" represented by $R^7$ to $R^{10}$ includes, for example, methyl, ethyl, propyl, isopropyl, butyl, isobutyl, sec-butyl, tert-butyl etc. Concretely, the "spacer having from 1 to 3 atoms as a main chain" include, for example, —$CR^7R^8$—, —$NR^9$—, —CO—, —O—, —S—, —$C(=N—OR^{10})$—, —$NR^9CO$—, —$CONR^9$—, —$NR^9COCR^7R^8$— or —$CONR^9CR^7R^8$— (wherein $R^7$-$R^{10}$ have the same meanings as described above.).

"C1-2 alkylene" represented by Y is methylene or ethylene.

The "3- to 15-membered carbocyclic group" in the "3- to 15-membered carbocyclic group or heterocyclic group which may have a substituent(s)" represented by ring A and ring B includes, for example, a "3- to 15-membered cyclic hydrocarbon" etc. The "cyclic hydrocarbon" in the "3- to 15-membered cyclic hydrocarbon" includes, for example, an "unsaturated cyclic hydrocarbon" or a "saturated cyclic hydrocarbon". The "saturated cyclic hydrocarbon" includes, for example, cycloalkane such as cyclopropane, cyclobutane, cyclopentane, cyclohexane, cycloheptane, cyclooctane, cyclononane, cyclodecane, cycloundecane, cyclododecane, cyclotridecane, cyclotetradecane or cyclopentadecane etc; perhydropentalene; perhydroazulene; perhydroindene; perhydronaphthalene; perhydroheptalene; spiro[4.4]nonane; spiro[4.5]decane; spiro[5.5]undecane; bicyclo[2.2.1]heptane; bicyclo[3.1.1]heptane; bicyclo[2.2.2]octane; adamantane; noradamantane etc. The "unsaturated cyclic hydrocarbon" includes, for example, cycloalkene such as cyclopentene, cyclohexene, cycloheptene, cyclooctene, cyclopentadiene, cyclohexadiene, cycloheptadiene or cyclooctadiene etc; benzene; pentalene; azulene; indene; indan; naphthalene; dihydronaphthalene; tetrahydronaphthalene; heptalene; biphenylene; as-indacene; s-indacene; acenaphthene; acenaphthylene; fluorene; phenalene; phenanthrene; anthracene; bicyclo[2.2.1]hept-2-ene; bicyclo[3.1.1]hept-2-ene; bicyclo[2.2.2]oct-2-ene etc.

The "3- to 15-membered heterocyclic group" in "3- to 15-membered carbocyclic group or heterocyclic group which may have a substituent(s)" represented by ring A and ring B have the same meanings as the above-described "3- to 15-membered heterocyclic group" in "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$.

The "substituents" in "3- to 15-membered carbocyclic group or heterocyclic group which may have a substituent(s)" represented by ring A and ring B have the same meanings as the "substituents" in the "hydrocarbon group which may have a substituent(s)" or "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$. The 1 to 10 substituents may exist wherever possible. When the number of substituents is two or more, each substituent may be same or different.

The "5- or 6-membered aromatic ring group" in the "5- or 6-membered aromatic ring group which may have a substituent(s)" represented by ring A and ring B, include, for example, benzene, pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole or thiadiazole ring etc.

The "substituents" in the "5- or 6-membered aromatic ring group which may have a substituent(s)" represented by ring A and ring B have the same meanings as the "substituents" in the "hydrocarbon group which may have a substituent(s)" or "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$. The 1 to 10 substituents may exist wherever possible. When the number of substituents is two or more, each substituent may be same or different.

The "nitrogen-containing heterocyclic group" in the "3- to 15-membered nitrogen-containing heterocyclic group which may have a substituent(s)" represented by ring D refers to a heterocycle which may contain, in addition to at least one nitrogen atom besides carbon atom, 1 to 3 hetero atoms selected from nitrogen, oxygen and sulfur atoms. The "3- to 15-membered nitrogen-containing heterocycle" includes a "3- to 15-membered nitrogen-containing unsaturated heterocycle" and "3- to 15-membered nitrogen-containing saturated heterocycle".

The "3- to 15-membered nitrogen-containing unsaturated heterocyclic group" includes, for example, pyrrole, imidazole, triazole, tetrazole, pyrazole, indole, isoindole, indazole, purine, benzimidazole, benzoazepine, benzodiazepine, benzotriazole, carbazole, β-carboline, phenothiazine, phenoxazine, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzoazepine, tetrahydrobenzoazepine, dihydrobenzodiazepine, tetrahydrobenzodiazepine, dihydrobenzooxazepine, tetrahydrobenzooxazepine, dihydrocarbazole, tetrahydrocarbazole, dihydroacridine, tetrahydroacridine; or 3- to 15-membered nitrogen-containing saturated heterocyclic group includes, for example, aziridine, azetidine, azocane, pyrrolidine, imidazolidine, triazolidine, tetrazolidine, pyrazolidine, piperidine, piperazine, perhydropyrimidine, perhydropyridazine, azepane (perhydroazepane), perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, tetrahydrothiazepine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine,

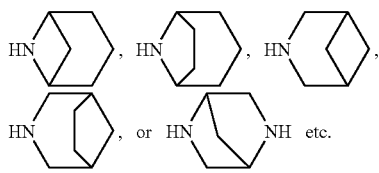

The "substituents" in the "3- to 15-membered nitrogen-containing heterocyclic group which may have a substituent(s)" represented by ring D have the same meanings as the "substituents" in the "hydrocarbon group which may have a substituent(s)" or "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$. The 1 to 10 substituents may exist wherever possible. When the number of substituents is two or more, each substituent may be same or different.

The "5- to 10-membered nitrogen-containing heterocyclic group" in the "5- to 10-membered nitrogen-containing heterocyclic group which may have a substituent(s)" represented by ring D refers to "5- to 10-membered nitrogen-containing heterocyclic group" of the above-described "3- to 15-membered nitrogen-containing heterocyclic group" represented by ring D. Examples of pyrrolidine, piperidine, piperazine, azepane, or tropane, etc. are included.

The "substituents" in the "5- to 10-membered nitrogen-containing heterocyclic group which may have a substituent(s)" represented by ring D have the same meanings as the "substituents" in the "hydrocarbon group which may have a substituent(s)" or "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$. The 1 to 10 substituents may exist wherever possible. When the number of substituents is two or more, each substituent may be same or different.

The "hydroxy group which may be protected" represented by $R^2$ is the "hydroxy group" which may be protected by a "protecting group". The "protecting group" of hydroxy group includes, for example, (1) C1-6 alkyl group (e.g., methyl, ethyl, propyl, isopropyl, butyl, tert-butyl, etc.) which may have 1 to 4 of substituents selected from (a) halogen atom such as chlorine, bromine or fluorine etc.; (b) C6-10 aryl such as phenyl or naphthyl etc.; (c) C7-12 aralkyl group such as benzyl or phenylethyl etc.; and (d) nitro group etc., (2) C6-10 aryl (e.g., phenyl or naphthyl etc.) which may have 1 to 4 of substituents selected from (a) halogen atom such as chlorine, bromine or fluorine etc.; (b) C1-6 alkyl group such as methyl, ethyl or propyl etc.; (c) C6-10 aryl such as phenyl or naphthyl etc.; (d) C7-12 aralkyl group such as benzyl or phenylethyl etc.; and (e) nitro group etc., (3) C7-12 aralkyl group (e.g., benzyl, phenylethyl or naphthylmethyl etc.) which may have 1 to 4 of substituents selected from (a) halogen atom such as chlorine, bromine or fluorine etc.; (b) C1-6 alkyl group such as methyl, ethyl or propyl etc.; (c) C6-10 aryl such as phenyl or naphthyl etc.; (d) C7-12 aralkyl group such as benzyl or phenylethyl etc.; and (e) nitro group etc., (4) formyl, (5) C1-6 alkyl-carbonyl group (e.g., acetyl or propionyl etc.) which may have 1 to 4 of substituents selected from (a) halogen atom such as chlorine, bromine or fluorine etc.; (b) C1-6 alkyl group such as methyl, ethyl or propyl etc.; (c) C6-10 aryl such as phenyl or naphthyl etc.; (d) C7-12 aralkyl group such as benzyl or phenylethyl etc.; and (e) nitro group etc., (6) C6-10 aryl-oxycarbonyl group (e.g., phenyloxycarbonyl or naphthyloxycarbonyl etc.) which may have 1 to 4 of substituents selected from (a) halogen atom such as chlorine, bromine or fluorine etc.; (b) C1-6 alkyl group such as methyl, ethyl or propyl etc.; (c) C6-10 aryl such as phenyl or naphthyl etc.; (d) C7-12 aralkyl group such as benzyl or phenylethyl etc.; and (e) nitro group etc., (7) C6-10 aryl-carbonyl group (e.g., benzoyl or naphthylcarbonyl etc.) which may have 1 to 4 of substituents selected from (a) halogen atom such as chlorine, bromine or fluorine etc.; (b) C1-6 alkyl group such as methyl, ethyl or propyl etc.; (c) C6-10 aryl such as phenyl or naphthyl etc.; (d) C7-12 aralkyl group such as benzyl or phenylethyl etc.; and (e) nitro group etc., (8) C7-12 aralkyl-carbonyl group (e.g., benzylcarbonyl or phenethylcarbonyl etc.) which may have 1 to 4 of substituents selected from (a) halogen atom such as chlorine, bromine or fluorine etc.; (b) C1-6 alkyl group such as methyl, ethyl or propyl etc.; (c) C6-10 aryl such as phenyl or naphthyl etc.; (d) C7-12 aralkyl group such as benzyl or phenylethyl etc.; and (e) nitro group etc., (9) pyranyl or furanyl which may have 1 to 4 of substituents selected from (a) halogen atom such as chlorine, bromine or fluorine etc.; (b) C1-6 alkyl group such as methyl, ethyl or n-propyl etc.; (c) C6-10 aryl such as phenyl or naphthyl etc.; (d) C7-12 aralkyl group such as benzyl or phenylethyl etc.; and (e) nitro group etc., or (10) tri-C1-4 alkylsilyl such as trimethylsilyl or triethylsilyl etc.

The "substituents" in the "amino group which may have a substituent(s)" represented by $R^2$ includes hydrocarbon group which may have a substituent(s), $-SO_2R^{201}$ or $=NR^{202}$ (wherein $R^{201}$ and $R^{202}$ is hydrocarbon group which may have a substituent(s)). The "hydrocarbon group which may have a substituent(s)" has the same meaning as the "hydrocarbon group which may have a substituent(s)" represented by $R^{1A}$, $R^{1B}$, $R^{1C}$, $R^{1D}$, $R^{1E}$, $R^{1F}$, $R^{1G}R^{1H}$, $R^{1J}$, $R^{1K}$, and $R^{1L}$. The 1 or 2 substituents which amino group has may exist wherever possible. When the number of substituents is two or more, each substituent may be same or different. "Amino group which may have a substituent(s)" represented by $R^2$ is

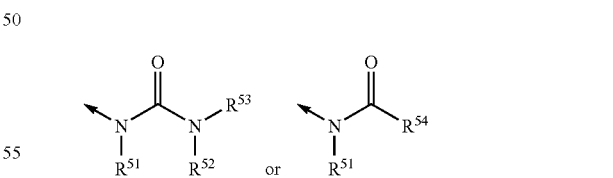

(wherein the arrow represents a binding position to ring D, and $R^{51}$, $R^{52}$, $R^{53}$ and $R^{54}$ are each independently hydrogen atom, hydrocarbon group which may have a substituent(s), 3- to 15-membered heterocyclic group which may have a substituent(s), C1-4 alkoxy group which may have a substituent(s), phenoxy which may have a substituent(s) or benzyloxy which may have a substituent(s).). The "hydrocarbon group which may have a substituent(s)" and "3- to 15-membered heterocyclic group which may have a substituent(s)" have the same meanings as the "hydrocarbon group which may have a substituent(s)" and "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$ respectively. "C1-4 alkoxy group" in the "C1-4 alkoxy group which may have a substituent(s)" includes, for example, methoxy, ethoxy, propoxy, isopropoxy, butoxy, isobutoxy, sec-butoxy or tert-butoxy etc. The "substituents" of "C1-4 alkoxy group which may have a substituent(s)", "phenoxy group which may have a substituent(s)" and "benzyloxy group which may have a substituent(s)" include, for example, the "substituents" in the "hydrocarbon group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$ etc.

The "hydrocarbon group which may have a substituent(s)" represented by $R^2$ have the same meanings as the "hydrocarbon group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$. The 1 to 10 substituents which the hydrocarbon group has may exist wherever possible. When the number of substituents is two or more, each substituent may be same or different. The "hydrocarbon group which may have a substituent(s)" represented by $R^2$ is

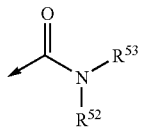

(wherein the arrow represents a binding position to ring D, and $R^{52}$ and $R^{53}$ have the same meanings as described above.)

The "3- to 15-membered heterocyclic group which may have a substituent(s)" represented by $R^2$ has the same meanings as the "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$.

C1-4 alkyl represented by $R^6$ includes, for example, methyl, ethyl, propyl, isopropyl, butyl, isobutyl, sec-butyl, tert-butyl, etc.

The "hydrocarbon group which may have a substituent(s)" represented by $R^{51}$ have the same meanings as the "hydrocarbon group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$.

The "C1-15 alkyl" represented by $R^{51}$ have the same meanings as the "C1-15 alkyl" as the "hydrocarbon group" in the "hydrocarbon group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$.

The "aromatic ring group" in the "aromatic ring group which may have a substituent(s)" represented by $R^{51}$ refers to the "mono-, bi- or tricyclic carbocyclic group or heterocyclic group which have aromaticity" of the "hydrocarbon group" in the "hydrocarbon group which may have a substituent(s)" and "3- to 15-membered heterocyclic group" in the "3- to 15-membered heterocyclic group which may have a substituent(s)" represented by $R^{51}$. The "mono-, bi- or tricyclic carbocyclic group which have aromaticity" include, for example, benzene, azulene, naphthalene, phenanthrene, anthracene ring, etc. The "mono-, bi- or tricyclic heterocyclic group which have aromaticity" include, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, beta-carboline, acridine, phenazine, dibenzofuran, dibenzothiophene, phenanthridine, phenanthroline, perimidine ring, etc.

The "substituents" in the "aromatic ring group which may have a substituent(s)" represented by $R^{51}$ have the same meanings as the "substituents" in the "hydrocarbon group which may have a substituent(s)" or "3- to 15-membered heterocyclic group which may have a substituent(s)" represented by $R^{1A}$, $R^{1B}$, $R^{1C}$, $R^{1D}$, $R^{1E}$, $R^{1F}$, $R^{1G}$, $R^{1H}$, $R^{1J}$, $R^{1K}$, and $R^{1L}$. The 1 to 10 substituents may exist wherever possible. When the number of substituents is two or more, each substituent may be same or different.

The "mono-carbocyclic group or mono-heterocyclic group which have aromaticity" represented by $R^{51}$ refers to monocyclic group of the above-described "aromatic ring group" represented by $R^{51}$. Examples of benzene, pyrrole, imidazole, triazole, tetrazole, pyrazole, pyridine, pyrazine, pyrimidine, pyridazine, oxazole, isoxazole, thiazole, isothiazole, furazan, oxadiazole or thiadiazole ring etc. are included.

The "aromatic ring group which may have a substituent(s)" represented by $R^{56}$ have the same meanings as the above-described "aromatic ring group which may have a substituent(s)" represented by $R^{51}$.

Unless otherwise specifically mentioned, all isomers are included in the present invention. For example, alkyl, alkenyl, Alkynyl, alkoxy, alkylthio, alkylene, alkenylene and alkynylene include straight chain and branched ones. Moreover, all of isomers due to double bond, ring and fused ring (E-, Z-, cis- and trans-forms), isomers due to presence of asymmetric carbon(s) etc. (R-, S-, α- and β-configuration, enantiomer and diastereomer), optically active substances having optical rotation (D-, L-, d- and l-forms), polar compound by chromatographic separation (more polar compound and less polar compound), equilibrium compounds, rotational isomers, a mixture thereof in any proportion and a racemic mixture are included in the present invention.

According to the present invention, symbol ⇀ represents β-configuration and symbol ⇁ represents α-configuration, β-configuration or the mixture of them. There is no particular limitation for the ratio of α-configuration and β-configuration in the mixture.

Salts:

The salt of the compound of formula (I) includes all of the salt which are non-toxic salts or pharmaceutically acceptable salts. With regard to the pharmaceutically acceptable salts, those which are low-toxic and soluble in water are preferred. Examples of appropriate salts of the compound of formula (I) are salt with alkaline metal (such as potassium, sodium and lithium), salt with alkaline earth metal (such as calcium and magnesium), ammonium salt (such as tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl)methylamine, lysine, arginine and N-methyl-D-glucamine) and acid addition salt [such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate), etc.]. The salt of the compound of the present invention also includes solvates and also solvates with the above-mentioned alkaline (earth) metal salt, ammonium salt, organic amine salt and acid addition salt. The solvate is preferably low-toxic and water-soluble. Examples of an appropriate solvate are solvates with water and with alcoholic solvent (such as ethanol). The compounds of the present invention are converted to low-toxic salts or pharmaceutically acceptable salts by known methods.

Moreover, the salt includes a quaternary ammonium salt. The quaternary ammonium salt of the compound represented by formula (I) is the compound where nitrogen of the compounds represented by formula (I) is quarternalized by $R^0$ ($R^0$ is C1-8 alkyl or C1-8 alkyl substituted by phenyl.).

The salt also includes an N-oxide. The compound of the present invention can be converted into an N-oxide by known methods. The N-oxide is the compound where nitrogen of the compound represented by formula (I) is oxidized.

Prodrugs:

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g., compounds in which the hydroxyl group of the compound of formula (I) is acetylated, palmitoylated, propanoylated, pivaloylated, succinylated, fumarylated, alanylated or dimethylaminomethylcarbonylated); and that the carboxyl group of the compound of formula (I) is, for example, esterified or amidated (e.g., compounds in which the carboxyl group of the compound of formula (I) is made into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound of formula (I) may be either a hydrate or a non-hydrate. A prodrug of the compound of formula (I) may also be a compound which is converted to the compound of formula (I) under physiologic condition as described in "Iyakuhin no kaihatsu, Vol. 7 (Bunshi-sekkei), pp. 163-198 (Hirokawa-Shoten), 1990". And the compound of formula (I) may also be labeled by a radio isotope (such as $^3H$, $^{14}C$, $^{35}S$, $^{125}I$, etc,).

All definition represented by $R^1$, X, Y, ring A, ring B, ring D, and $R^2$ in the formula (I) in the present invention is preferred. All symbols in each preferred group listed below have the same meanings as described above.

Preferred as $R^1$ is, for example, —N($R^{1A}$)SO$_2$—$R^{1B}$, —SO$_2$NR$^{1C}$R$^{1D}$, —S(O)$_m$R$^{1G}$, —CONR$^{1H}$R$^{1J}$, —NR$^{1K}$COR$^{1L}$, etc., and more preferred is, for example, —N(R$^{1A}$)SO$_2$—R$^{1B}$, —SO$_2$NR$^{1C}$R$^{1D}$, —S(O)$_m$R$^{1G}$, —CONR$^{1H}$R$^{1J}$, etc. Preferred as R$^{1A}$, R$^{1B}$, R$^{1C}$, R$^{1D}$, R$^{1E}$, R$^{1F}$, R$^{1G}$, R$^{1H}$, R$^{1J}$, R$^{1K}$, and R$^{1L}$ is, for example, hydrogen atom or hydrocarbon group which may have a substituent(s), etc. Most preferred as $R^1$ is, for example, —NHSO$_2$CH$_3$, —NHSO$_2$CH$_2$CH$_3$, —SO$_2$NHCH$_3$, —SO$_2$CH$_3$, —CONHCH$_2$CH$_2$OCH$_3$, etc.

Preferred as X is, for example, a bond, —CR$^7$R$^8$—, —NR$^9$—, —CO—, —O—, —S—, —SO—, —SO$_2$—, or —C(=N—OR$^{10}$)—, etc. More preferably, X is bond, —O—, or —CH$_2$—, etc.

Preferred as Y is, for example, methylene, ethylene or propylene etc. More preferably, Y is methylene, ethylene. Most preferably, Y is methylene.

Preferably, ring A or ring B is, for example, a "5- to 10-membered carbocyclic group or heterocyclic group" (it refers to 5- to 10-membered carbocyclic group or heterocyclic group of the above-described 3- to 15-membered carbocyclic or heterocyclic group) etc. More preferably is, for example, a "5- to 10-membered unsaturated carbocyclic group or heterocyclic group" (it refers to 5- to 10-membered unsaturated carbocyclic group or heterocyclic group of the above-described 3- to 15-membered carbocyclic or heterocyclic group) etc. More preferred is, for example, 5- or 6-aromatic ring such as benzene, pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole or thiadiazole ring etc. Most preferred is, for example, benzene or pyridine ring etc. Preferably, the substituent of ring A or ring B is, for example, hydrocarbon group, alkoxy, halogen atom, carboxy, alkanoylamide, etc., and more preferred is, for example, hydrocarbon group, alkoxy, halogen atom, etc., and most preferred is, for example, chloro atom, methyl, or methoxy, etc.

Preferably, ring D is, for example, a "5- to 10-membered nitrogen-containing heterocyclic group" (it refers to 5- to 10-membered nitrogen-containing heterocyclic group of the above-described 3- to 15-membered nitrogen-containing heterocyclic group) etc., and more preferred is, for example, tropane, pyrrolidine, piperidine, azepane, or piperazine ring, etc., and most preferred is, for example, piperidine ring. Preferably, ring D has no substituent or is substituted by hydrocarbon group, mono-C1-4 alkylamino group or di-C1-4 alkylamino group etc. More preferably, ring D has no substituent.

Preferred as $R^2$ is, for example, hydrocarbon group which may have a substituent(s) or amino group which may have a substituent(s), etc. Preferred as the "substituents" is the "hydrocarbon group which may have a substituent(s)". Concretely, more preferred as $R^2$, for example,

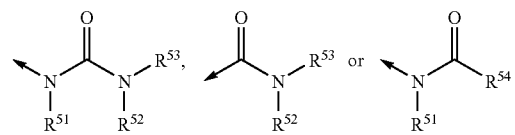

(wherein the arrow represents a binding position to ring D, each $R^{51}$, $R^{52}$, $R^{53}$ and $R^{54}$ has the same meanings as described above.), etc., independently. Preferably, $R^{51}$, $R^{52}$, $R^{53}$ or $R^{54}$ is, for example, hydrogen atom, hydrocarbon group which may have a substituent(s) or 3- to 15-membered heterocyclic group which may have a substituent(s) etc. Moreover, the compound wherein either among $R^{52}$ and $R^{53}$ is hydrogen atom is preferred. More preferred as $R^2$ is, for example,

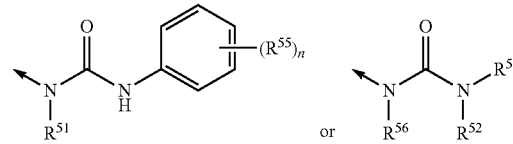

($R^{55}$ has the same meaning as the "substituents" in the "hydrocarbon group which may have a substituent(s)" represented by R$^{1A}$, R$^{1B}$, R$^{1C}$, R$^{1D}$, R$^{1E}$, R$^{1F}$, R$^{1G}$, R$^{1H}$, R$^{1J}$, R$^{1K}$, and R$^{1L}$; n is 0 to 5, and other symbols have the same meanings as described above.), etc. Preferred as $R^{51}$ is, for example, hydrocarbon group which may have a substituent(s), etc., and more preferred is, for example, C1-15 alkyl which may have a substituent(s), C6-14 aryl which may have a substituent(s), or $R^{56}$, etc., and most preferred is, for example, butyl or phenyl which may have a substituent(s), etc. Preferred as the substituent is methyl, methoxy, trifluoromethyl, fluorine atom, etc., and more preferred is methyl or fluorine atom. Preferred as $R^{55}$ is, for example, halogen atom, carbamoyl, or aminocarbonyl substituted by C1-8 hydrocarbon group, etc., and more preferred is, for example, fluorine atom, chlorine atom, carbamoyl, N-methylaminocarbonyl, etc. Preferred as n is 1 to 3.

Preferred as $R^{56}$ is mono-carbocyclic group or mono-heterocyclic group which have aromaticity which may have a substituent(s), and more preferred is benzene, pyrrole, imidazole, triazole, tetrazole, pyrazole, pyridine, pyrazine, pyrimidine, pyridazine, oxazole, isoxazole, thiazole, isothiazole, furazan, oxadiazole or thiadiazole ring which may have a substituent(s), and most preferred is benzene ring which may have a substituent(s). Preferred as the substituent is methyl, methoxy, trifluoromethyl, fluorine atom, etc., and more preferred is methyl or fluorine atom.

In the present invention, the compound represented by formula (I) including the combination of the above-described preferable group and ring is preferred.

For example, a compound wherein ring D is piperidine and Y is methylene group, i.e., a compound represented by formula (Ia)

(Ia)

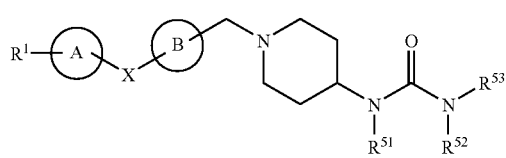

(wherein all symbols have the same meanings as described above.); a compound wherein ring D is piperidine and Y is methylene group, $R^2$ is

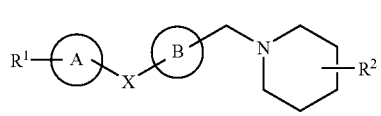

(wherein all symbols have the same meanings as described above.), i.e., a compound represented by formula (Ib)

(Ib)

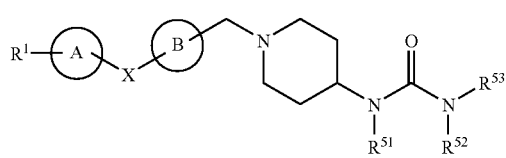

(wherein all symbols have the same meanings as described above.); a compound wherein X is —O—, Y is methylene group, ring A and ring B are each independently benzene which may have a substituent(s), ring D is piperidine, $R^2$ is

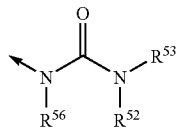

(wherein all symbols have the same meanings as described above.), i.e., a compound represented by formula (Ic)

(Ic)

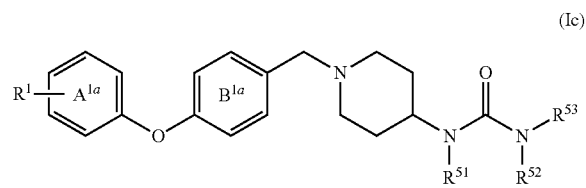

(wherein ring $A^{1a}$ and ring $B^{1a}$ are each independently benzene which may have a substituent(s) and other symbols have the same meanings as described above.); a compound wherein X is —O—, Y is methylene group, ring A and ring B are each independently benzene which may have a substituent(s), ring D is piperidine, $R^2$ is

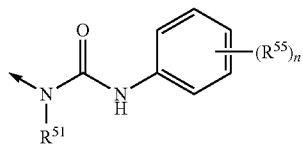

(wherein all symbols have the same meanings as described above.), i.e., a compound represented by formula (Id)

(Id)

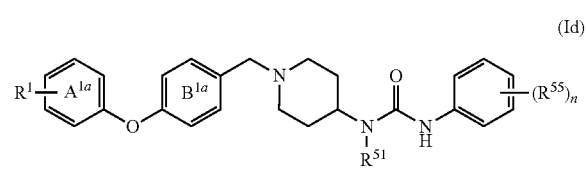

(wherein all symbols have the same meanings as described above.); a compound wherein ring D is tropane ring and Y is methylene group, $R^2$ is

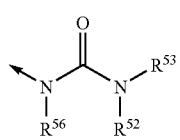

(wherein all symbols have the same meanings as described above.), i.e., a compound represented by formula (Ie)

(Ie)

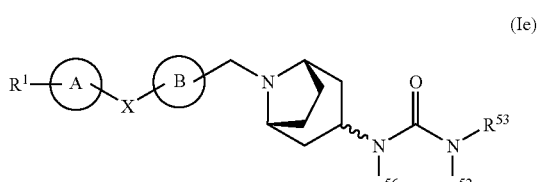

(wherein all symbols have the same meanings as described above.); a compound wherein ring D is pyrrolidine ring and Y is methylene group, $R^2$ is

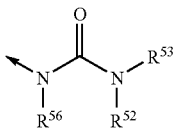

(wherein all symbols have the same meanings as described above.), i.e., a compound represented by formula (If)

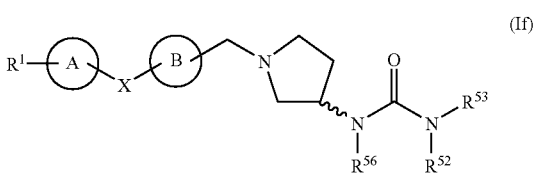

(wherein all symbols have the same meanings as described above.); a compound wherein ring D is piperidine and Y is methylene group, $R^2$ is

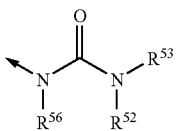

(wherein all symbols have the same meanings as described above.), i.e., a compound represented by formula (Ig)

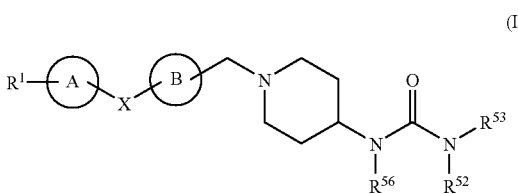

(wherein all symbols have the same meanings as described above.); a compound wherein ring D is azepane ring and Y is methylene group, $R^2$ is

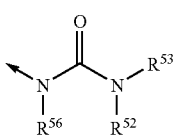

(wherein all symbols have the same meanings as described above.), i.e., a compound represented by formula (Ih)

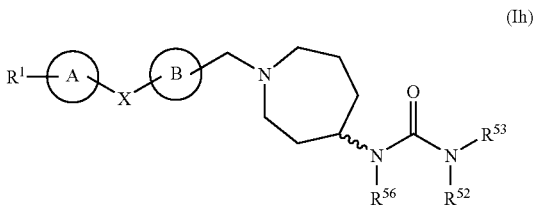

(wherein all symbols have the same meanings as described above.), salts thereof, N-oxides thereof, solvates thereof, and prodrugs thereof are preferred.

Preferred are compounds described in Examples, salts thereof, N-oxides thereof, solvates thereof, and prodrugs thereof. More preferred are (1) 5-({[butyl(1-{4-[4-(methylsulfonyl)phenoxy]benzyl}-4-piperidinyl)amino]carbonyl}amino)-2,4-difluorobenzamide,
(2) 5-[({butyl[1-({6-[4-(methylsulfonyl)phenoxy]-3-pyridinyl}methyl)-4-piperidinyl]amino}carbonyl)amino]-2,4-difluorobenzamide,
(3) 5-({[butyl(1-{[6-(4-{[(2-methoxyethyl)amino]carbonyl}phenoxy)-3-pyridinyl]methyl}-4-piperidinyl)amino]carbonyl}amino)-2,4-difluorobenzamide,
(4) 5-{[(butyl{1-[(6-{4-[(ethylsulfonyl)amino]phenoxy}-3-pyridinyl)methyl]-4-piperidinyl}amino)carbonyl]amino}-2,4-difluorobenzamide,
(5) N-(4-{[5-({4-[{[(4-fluorophenyl)amino]carbonyl}(phenyl)amino]-1-piperidinyl}methyl)-2-pyridinyl]oxy}-3-methoxyphenyl)methanesulfonamide,
(6) 5-{[(butyl{1-[(6-{2-methyl-4-[(methylsulfonyl)amino]phenoxy}-3-pyridinyl)methyl]-4-piperidinyl}amino)carbonyl]amino}-2-chloro-4-fluorobenzamide,
(7) 2-(5-{[(butyl{1-[(6-{4-[(methylsulfonyl)amino]phenoxy}-3-pyridinyl)methyl]-4-piperidinyl}amino)carbonyl]amino}-2,4-difluorophenyl)acetamide,
(8) 5-[({butyl[1-(4-{4-[(methylsulfonyl)amino]phenoxy}benzyl)-4-piperidinyl]amino}carbonyl)amino]-2,4-difluoro-N-methylbenzamide,
(9) 5-{[(butyl{1-[(6-{4-[(methylsulfonyl)amino]phenoxy}-3-pyridinyl)methyl]-4-piperidinyl}amino)carbonyl]amino}-2,4-difluorobenzamide,
(10) N-(4-{[5-({4-[{[(4-fluorophenyl)amino]carbonyl}(phenyl)amino]-1-piperidinyl}methyl)-2-pyridinyl]oxy}phenyl)methanesulfonamide,
(11) 5-[({butyl[1-(4-{4-[(methylamino)sulfonyl]phenoxy}benzyl)-4-piperidinyl]amino}carbonyl)amino]-2,4-difluorobenzamide,
(12) N-(4-{[5-({4-[{[(4-fluorophenyl)amino]carbonyl}(3-thienyl)amino]-1-piperidinyl}methyl)-2-pyridinyl]oxy}phenyl)methanesulfonamide,
(13) N-[4-({5-[(4-{3-thienyl[(3-thienylamino)carbonyl]amino}-1-piperidinyl)methyl]-2-pyridinyl}oxy)phenyl]methanesulfonamide,
(14) 2-fluoro-5-({[{1-[(6-{4-[(methylsulfonyl)amino]phenoxy}-3-pyridinyl)methyl]-4-piperidinyl}(phenyl)amino]carbonyl}amino)benzamide,
(15) N-{4-[4-({4-[{[(4-fluorophenyl)amino]carbonyl}(phenyl)amino]-1-piperidinyl}methyl)-3,5-dimethyl-1H-pyrazol-1-yl]phenyl}methanesulfonamide,
(16) 4-[4-({4-[{[(4-fluorophenyl)amino]carbonyl}(phenyl)amino]-1-piperidinyl}methyl)-3,5-dimethyl-1H-pyrazol-1-yl]-N-[2-(4-morpholinyl)ethyl]benzenesulfonamide,
(17) N-(4-{[5-({4-[{[(2,4-difluorophenyl)amino]carbonyl}(3-thienyl)amino]-1-piperidinyl}methyl)-2-pyridinyl]oxy}phenyl)methanesulfonamide,
(18) 2-chloro-N-methyl-5-({[{1-[(6-{4-[(methylsulfonyl)amino]phenoxy}-3-pyridinyl)methyl]-4-piperidinyl}(phenyl)amino]carbonyl}amino)benzamide,
(19) N-(4-{[5-({4-[({[4-chloro-3-(4-morpholinylcarbonyl)phenyl]amino}carbonyl)(phenyl)amino]-1-piperidinyl}methyl)-2-pyridinyl]oxy}phenyl)methanesulfonamide,
(20) 2-fluoro-5-{[((3-fluorophenyl){1-[(6-{4-[(methylsulfonyl)amino]phenoxy}-3-pyridinyl)methyl]-4-piperidinyl}amino)carbonyl]amino}benzamide,
(21) N-(3-fluorophenyl)-N'-(6-methyl-3-pyridinyl)-N-[1-({6-[4-(methylsulfonyl)phenoxy]-3-pyridinyl}methyl)-4-piperidinyl]urea,

(22) 2-[4-({4-[[({4-fluoro-3-[(methylsulfonyl)amino]phenyl}amino)carbonyl](phenyl)amino]-1-piperidinyl}methyl)phenoxy]-5-[(methylsulfonyl)amino]benzamide,
(23) 2-fluoro-N-methyl-5-({[{1-[(6-{4-[(methylsulfonyl)amino]phenoxy}-3-pyridinyl)methyl]-4-piperidinyl}(phenyl)amino]carbonyl}amino)benzamide,
(24) 2-fluoro-N-methyl-5-({[[1-({6-[4-(methyl sulfonyl)phenoxy]-3-pyridinyl}methyl)-4-piperidinyl](phenyl)amino]carbonyl}amino)benzamide,
(25) 2-[4-({4-[({[3-(acetylamino)-4-fluorophenyl]amino}carbonyl)(phenyl)amino]-1-piperidinyl}methyl)phenoxy]-5-[(methylsulfonyl)amino]benzamide,
(26) N'-(4-fluorophenyl)-N-[1-({6-[4-(methylsulfonyl)phenoxy]pyridin-3-yl}methyl)piperidin-4-yl]-N-phenylurea,
(27) N-(4-{[5-({4-[{[(6-methyl-3-pyridinyl)amino]carbonyl}(phenyl)amino]-1-piperidinyl}methyl)-2-pyridinyl]oxy}phenyl)methanesulfonamide,
(28) N-[2-fluoro-5-({[{1-[(6-{4-[(methylsulfonyl)amino]phenoxy}-3-pyridinyl)methyl]-4-piperidinyl}(phenyl)amino]carbonyl}amino)phenyl]acetamide,
(29) N-{4-[(5-{[4-((3-fluorophenyl){[(6-methyl-3-pyridinyl)amino]carbonyl}amino)-1-piperidinyl]methyl}-2-pyridinyl)oxy]phenyl}methanesulfonamide,
(30) 5-[({butyl[1-(4-{2-methyl-4-[(methylsulfonyl)amino]phenoxy}benzyl)-4-piperidinyl]amino}carbonyl)amino]-2,4-difluorobenzamide,
(31) N-(4-{[5-({4-[{[(2,4-difluorophenyl)amino]carbonyl}(phenyl)amino]-1-piperidinyl}methyl)-2-pyridinyl]oxy}-3-methoxyphenyl)methanesulfonamide,
(32) N-(4-{[5-({4-[{[(4-methylphenyl)amino]carbonyl}(phenyl)amino]-1-piperidinyl}methyl)-2-pyridinyl]oxy}phenyl)methanesulfonamide,
(33) N-(4-{[5-({4-[{[(4-chlorophenyl)amino]carbonyl}(phenyl)amino]-1-piperidinyl}methyl)-2-pyridinyl]oxy}phenyl)methanesulfonamide,
(34) N-(4-{[5-({4-[{[(4-fluorophenyl)amino]carbonyl}(phenyl)amino]-1-piperidinyl}methyl)-2-pyridinyl]oxy}phenyl)acetamide,
salts thereof, N-oxides thereof, solvates thereof, and pro-drugs thereof, etc. Most preferred are
2-fluoro-5-({[{1-[(6-{4-[(methylsulfonyl)amino]phenoxy}-3-pyridinyl)methyl]-4-piperidinyl}(phenyl)amino]carbonyl}amino)benzamide,
N-(4-{[5-({4-[{[(6-methyl-3-pyridinyl)amino]carbonyl}(phenyl)amino]-1-piperidinyl}methyl)-2-pyridinyl]oxy}phenyl)methanesulfonamide,
N-[2-fluoro-5-({[{1-[(6-{4-[(methylsulfonyl)amino]phenoxy}-3-pyridinyl)methyl]-4-piperidinyl}(phenyl)amino]carbonyl}amino)phenyl]acetamide,
N-{4-[(5-{[4-((3-fluorophenyl){[(6-methyl-3-pyridinyl)amino]carbonyl}amino)-1-piperidinyl]methyl}-2-pyridinyl)oxy]phenyl}methanesulfonamide,
5-[({butyl[1-(4-{2-methyl-4-[(methylsulfonyl)amino]phenoxy}benzyl)-4-piperidinyl]amino}carbonyl)amino]-2,4-difluorobenzamide,
N-(4-{[5-({4-[{[(2,4-difluorophenyl)amino]carbonyl}(phenyl)amino]-1-piperidinyl}methyl)-2-pyridinyl]oxy}-3-methoxyphenyl)methanesulfonamide,
N-(4-{[5-({4-[{[(4-methylphenyl)amino]carbonyl}(phenyl)amino]-1-piperidinyl}methyl)-2-pyridinyl]oxy}phenyl)methanesulfonamide,
N-(4-{[5-({4-[{[(4-chlorophenyl)amino]carbonyl}(phenyl)amino]-1-piperidinyl}methyl)-2-pyridinyl]oxy}phenyl)methanesulfonamide,
N-(4-{[5-({4-[{[(4-fluorophenyl)amino]carbonyl}(phenyl)amino]-1-piperidinyl}methyl)-2-pyridinyl]oxy}phenyl)acetamide,
salts thereof, N-oxides thereof, solvates thereof, and pro-drugs thereof, etc.

In the present invention,
(1) N-{4-[(5-{[4-((3-methylphenyl){[(6-methyl-3-pyridinyl)amino]carbonyl}amino)-1-piperidinyl]methyl}-2-pyridinyl)oxy]phenyl}methanesulfonamide,
(2) N-(2-fluoro-5-{([(((3-methylphenyl){1-[(6-{4-[(methylsulfonyl)amino]phenoxy}-3-pyridinyl)methyl]-4-piperidinyl}amino)carbonyl]amino}phenyl)acetamide,
(3) N-(2-fluoro-5-{[(((3-fluorophenyl){1-[(6-{4-[(methylsulfonyl)amino]phenoxy}-3-pyridinyl)methyl]-4-piperidinyl}amino)carbonyl]amino}phenyl)acetamide,
(4) N-(2-fluoro-5-{[(((3-fluorophenyl){1-[(6-{2-methyl-4-[(methylsulfonyl)amino]phenoxy}-3-pyridinyl)methyl]-4-piperidinyl}amino)carbonyl]amino}phenyl)acetamide,
(5) N-[5-({[{1-[(6-{2-chloro-4-[(methylsulfonyl)amino]phenoxy}-3-pyridinyl)methyl]-4-piperidinyl}(3-fluorophenyl)amino]carbonyl}amino)-2-fluorophenyl]acetamide,
(6) N-{4-[(5-{[4-((3-fluorophenyl){[(6-methyl-3-pyridinyl)amino]carbonyl}amino)-1-piperidinyl]methyl}-2-pyridinyl)oxy]-3-methylphenyl}methane sulfonamide,
(7) N-{3-chloro-4-[(5-{[4-((3-fluorophenyl){[(6-methyl-3-pyridinyl)amino]carbonyl}amino)-1-piperidinyl]methyl}-2-pyridinyl)oxy]phenyl}methanesulfonamide,
(8) 2-[(5-{[4-((3-fluorophenyl){[(6-methyl-3-pyridinyl)amino]carbonyl}amino)-1-piperidinyl]methyl}-2-pyridinyl)oxy]-5-[(methylsulfonyl)amino]benzamide,
(9) 2-[(5-{[4-((3-fluorophenyl){[(6-methyl-3-pyridinyl)amino]carbonyl}amino)-1-piperidinyl]methyl}-2-pyridinyl)oxy]-N-methyl-5-[(methylsulfonyl)amino]benzamide,
(10) N-[4-{[5-({4-[{[(6-methyl-3-pyridinyl)amino]carbonyl}(phenyl)amino]-1-piperidinyl}methyl)-2-pyridinyl]oxy}-3-(methylsulfonyl)phenyl]methanesulfonamide,
(11) N-{2-[(5-{[4-((3-methylphenyl){[(6-methyl-3-pyridinyl)amino]carbonyl}amino)-1-piperidinyl]methyl}-2-pyridinyl)oxy]-5-[(methylsulfonyl)amino]phenyl}acetamide,
(12) N-(4-{[5-({4-[[[(4-fluorophenyl)amino](imino)methyl](phenyl)amino]-1-piperidinyl}methyl)-2-pyridinyl]oxy}phenyl)methanesulfonamide,
(13) N-(4-{[5-({4-[{[(4-fluorophenyl)amino]carbonothioyl}(phenyl)amino]-1-piperidinyl}methyl)-2-pyridinyl]oxy}phenyl)methanesulfonamide,
(14) 2-fluoro-N-methyl-5-({[{1-[(6-{4-[(methylsulfonyl)amino]phenoxy}-3-pyridinyl)methyl]-3-azetidinyl}(phenyl)amino]carbonyl}amino)benzamide,
(15) N-(4-{[5-({(3R)-3-[{[(4-fluorophenyl)amino]carbonyl}(phenyl)amino]-1-pyrrolidinyl}methyl)-2-pyridinyl]oxy}phenyl)methanesulfonamide,
(16) N-[2-fluoro-5-({[{(3S)-1-[(6-{4-[(methylsulfonyl)amino]phenoxy}-3-pyridinyl)methyl]-3-pyrrolidinyl}(phenyl)amino]carbonyl}amino)phenyl]acetamide,
(17) N-(4-{[5-({(4R)-4-[{[(6-methyl-3-pyridinyl)amino]carbonyl}(phenyl)amino]-1-azepanyl}methyl)-2-pyridinyl]oxy}phenyl)methanesulfonamide,
(18) N-(4-{[5-({(4S)-4-[{[(4-chlorophenyl)amino]carbonyl}(phenyl)amino]-1-azepanyl}methyl)-2-pyridinyl]oxy}phenyl)methanesulfonamide,
(19) 2-fluoro-5-({[(1-{[6-({4-[(methylsulfonyl)amino]phenyl}sulfonyl)-3-pyridinyl]methyl}-4-piperidinyl)(phenyl)amino]carbonyl}amino)benzamide,

(20) N-(4-{[5-({4-[{[(4-fluorophenyl)amino]carbonyl}(phenyl)amino]-1-piperidinyl}methyl)-2-pyridinyl]methyl}phenyl)methanesulfonamide,
(21) 2-{[5-({4-[{[(4-chlorophenyl)amino]carbonyl}(3-fluorophenyl)amino]-1-piperidinyl}methyl)-2-pyridinyl]oxy}-5-[(methylsulfonyl)amino]benzamide,
(22) N-(3-methylphenyl)-N'-(6-methyl-3-pyridinyl)-N-[1-({6-[4-(methylsulfonyl)phenoxy]-3-pyridinyl}methyl)-4-piperidinyl]urea,
(23) N-[1-({6-[4-(ethylsulfonyl)phenoxy]-3-pyridinyl}methyl)-4-piperidinyl]-N-(3-fluorophenyl)-N'-(6-methyl-3-pyridinyl)urea,
(24) N-(3-fluorophenyl)-N-[1-({6-[4-(isopropylsulfonyl)phenoxy]-3-pyridinyl}methyl)-4-piperidinyl]-N'-(6-methyl-3-pyridinyl)urea,
(25) N-(4-{[5-({4-[{[(4-fluorophenyl)amino]carbonyl}(phenyl)amino]-1-piperidinyl}methyl)-2-pyridinyl]methyl}phenyl)ethanesulfonamide,
(26) 2-fluoro-5-{[((3-fluorophenyl){1-[(6-{4-[(methylsulfonyl)amino]phenoxy}-3-pyridinyl)methyl]-3-azetidinyl}amino)carbonyl]amino}benzamide,
(27) N-(4-{[5-({4-[{[(6-ethyl-3-pyridinyl)amino]carbonyl}(phenyl)amino]-1-piperidinyl}methyl)-2-pyridinyl]oxy}phenyl)methanesulfonamide,
(28) N-{4-[(5-{[4-((3-fluorophenyl){[(6-methyl-3-pyridinyl)amino]carbonyl}amino)-1-piperidinyl]methyl}-6-methyl-2-pyridinyl)oxy]phenyl}methanesulfonamide,
(29) N-[2-[(5-{[4-((3-fluorophenyl){[(6-methyl-3-pyridinyl)amino]carbonyl}amino)-1-piperidinyl]methyl}-2-pyridinyl)oxy]-5-(methylsulfonyl)phenyl]acetamide,
(30) N-(4-{[5-({4-[{[(6-ethyl-3-pyridinyl)amino]carbonyl}(3-fluorophenyl)amino]-1-piperidinyl}methyl)-2-pyridinyl]oxy}phenyl)methanesulfonamide,
(31) N-{2-{[5-({4-[{[(4-chlorophenyl)amino]carbonyl}(3-fluorophenyl)amino]-1-piperidinyl}methyl)-2-pyridinyl]oxy}-5-[(methylsulfonyl)amino]phenyl}acetamide,
(32) N-{2-[(5-{[4-((3-fluorophenyl){[(6-methyl-3-pyridinyl)amino]carbonyl}amino)-1-piperidinyl]methyl}-2-pyridinyl)methyl]-5-[(methylsulfonyl)amino]phenyl}acetamide,
(33) N-[4-(5-{[4-((3-fluorophenyl){[(6-methyl-3-pyridinyl)amino]carbonyl}amino)-1-piperidinyl]methyl}-2-pyridinyl)phenyl]methanesulfonamide,
(34) 2-fluoro-5-({[{1-[(2-methyl-6-{4-[(methylsulfonyl)amino]phenoxy}-3-pyridinyl)methyl]-4-piperidinyl}(phenyl)amino]carbonyl}amino)benzamide,
(35) N-{4-[(5-{[4-((3-fluorophenyl){[(6-methyl-3-pyridinyl)amino]carbonyl}amino)-1-piperidinyl]methyl}-2-pyridinyl)sulfonyl]phenyl}methanesulfonamide,
(36) N-(4-{[5-({4-[{[(4-chlorophenyl)amino]carbonyl}(3-methylphenyl)amino]-1-piperidinyl}methyl)-2-pyridinyl]oxy}phenyl)methanesulfonamide,
(37) N-(4-{[5-({4-[{[(4-fluorophenyl)amino]carbonyl}(3-methylphenyl)amino]-1-piperidinyl}methyl)-2-pyridinyl]oxy}phenyl)methanesulfonamide,
(38) 2-fluoro-5-({[{1-[(2-methyl-6-{4-[(methylsulfonyl)amino]phenoxy}-3-pyridinyl)methyl]-4-piperidinyl}(3-methylphenyl)amino]carbonyl}amino)benzamide,
(39) N-ethyl-2-fluoro-5-({[{1-[(6-{4-[(methylsulfonyl)amino]phenoxy}-3-pyridinyl)methyl]-4-piperidinyl}(phenyl)amino]carbonyl}amino)benzamide,
(40) 2-fluoro-N-methyl-5-({[{1-[(6-{4-[(methylsulfonyl)amino]phenoxy}-3-pyridinyl)methyl]-4-piperidinyl}(phenyl)amino]carbonothioyl}amino)benzamide,
(41) 2-fluoro-5-{[((3-fluorophenyl){(3S)-1-[(6-{4-[(methylsulfonyl)amino]phenoxy}-3-pyridinyl)methyl]-3-pyrrolidinyl}amino)carbonyl]amino}-N-methylbenzamide,
(42) N-[5-({[{(4S)-1-[(6-{4-[(ethylsulfonyl)amino]phenoxy}-3-pyridinyl)methyl]-4-azepanyl}(phenyl)amino]carbonyl}amino)-2-fluorophenyl]acetamide,
(43) 2-{[5-({4-[({[3-(acetylamino)-4-fluorophenyl]amino}carbonyl)(3-fluorophenyl)amino]-1-piperidinyl}methyl)-2-pyridinyl]oxy}-N-methyl-5-[(methylsulfonyl)amino]benzamide,
(44) N-[5-({[{1-[(6-{2-chloro-4-[(ethylsulfonyl)amino]phenoxy}-3-pyridinyl)methyl]-4-piperidinyl}(3-fluorophenyl)amino]carbonyl}amino)-2-fluorophenyl]acetamide,
(45) 5-({[{(3R)-1-[(6-{4-[(ethylsulfonyl)amino]phenoxy}-3-pyridinyl)methyl]-3-pyrrolidinyl}(phenyl)amino]carbonyl}amino)-2-fluorobenzamide,
(46) N-(3-chloro-4-{[5-({4-[{[(4-chlorophenyl)amino]carbonyl}(phenyl)amino]-1-piperidinyl}methyl)-2-pyridinyl]oxy}phenyl)methanesulfonamide,
(47) 5-({[{1-[(6-{2-(aminocarbonyl)-4-[(methylsulfonyl)amino]phenoxy}-3-pyridinyl)methyl]-4-piperidinyl}(3-fluorophenyl)amino]carbonyl}amino)-2-fluoro-N-methylbenzamide,
(48) 2-fluoro-N-methyl-5-({[{1-[(6-{2-methyl-4-[(methylsulfonyl)amino]phenoxy}-3-pyridinyl)methyl]-4-piperidinyl}(phenyl)amino]carbonyl}amino)benzamide,
(49) N-(4-{[5-({4-[{[(6-methyl-3-pyridinyl)amino]carbonyl}(phenyl)amino]-1-piperidinyl}methyl)-2-pyridinyl]sulfonyl}phenyl)methanesulfonamide,
(50) 2-fluoro-N-methyl-5-{[((3-methylphenyl){1-[(6-{4-[(methylsulfonyl)amino]phenoxy}-3-pyridinyl)methyl]-4-piperidinyl}amino)carbonyl]amino}benzamide,
(51) 2-fluoro-5-{[((3-methylphenyl){1-[(6-{4-[(methylsulfonyl)amino]phenoxy}-3-pyridinyl)methyl]-4-piperidinyl}amino)carbonyl]amino}benzamide,
(52) 2-fluoro-5-{[((3-fluorophenyl){1-[(6-{4-[(methylsulfonyl)amino]phenoxy}-3-pyridinyl)methyl]-4-piperidinyl}amino)carbonyl]amino}-N-methylbenzamide,
(53) N-(3-methyl-4-{[5-({4-[{[(6-methyl-3-pyridinyl)amino]carbonyl}(phenyl)amino]-1-piperidinyl}methyl)-2-pyridinyl]oxy}phenyl)methanesulfonamide,
(54) N-(3-chloro-4-{[5-({4-[{[(6-methyl-3-pyridinyl)amino]carbonyl}(phenyl)amino]-1-piperidinyl}methyl)-2-pyridinyl]oxy}phenyl)methanesulfonamide,
(55) N-(4-{[5-({4-[{[(6-methyl-3-pyridinyl)amino]carbonyl}(phenyl)amino]-1-piperidinyl}methyl)-2-pyridinyl]oxy}phenyl)ethanesulfonamide,
(56) N-(4-{[5-({4-[{[(6-methyl-3-pyridinyl)amino]carbonyl}(phenyl)amino]-1-piperidinyl}methyl)-2-pyrazinyl]oxy}phenyl)methanesulfonamide,
(57) N-(4-{[5-({(3S)-3-[{[(6-methyl-3-pyridinyl)amino]carbonyl}(phenyl)amino]-1-pyrrolidinyl}methyl)-2-pyridinyl]oxy}phenyl)methanesulfonamide,
(58) N-(4-{[5-({(4S)-4-[{[(6-methyl-3-pyridinyl)amino]carbonyl}(phenyl)amino]-1-azepanyl}methyl)-2-pyridinyl]oxy}phenyl)methanesulfonamide,
(59) N-(4-{[5-({(3R)-3-[{[(6-methyl-3-pyridinyl)amino]carbonyl}(phenyl)amino]-1-pyrrolidinyl}methyl)-2-pyridinyl]oxy}phenyl)methanesulfonamide,
(60) 2-{[5-({4-[{[(6-methyl-3-pyridinyl)amino]carbonyl}(phenyl)amino]-1-piperidinyl}methyl)-2-pyridinyl]oxy}-5-[(methylsulfonyl)amino]benzamide,

(61) 2-{5-({4-[({[3-(acetylamino)-4-fluorophenyl]amino}carbonyl)(3-fluorophenyl)amino]-1-piperidinyl}methyl)-2-pyridinyl]oxy}-5-[(methylsulfonyl)amino]benzamide,
(62) 2-{5-({4-[{[(4-chlorophenyl)amino]carbonyl}(phenyl)amino]-1-piperidinyl}methyl)-2-pyridinyl]oxy}-5-[(methylsulfonyl)amino]benzamide,
(63) N-[4-[(5-{[4-((3-fluorophenyl){[(6-methyl-3-pyridinyl)amino]carbonyl}amino)-1-piperidinyl]methyl}-2-pyridinyl)oxy]-3-(methylsulfonyl)phenyl]methanesulfonamide,
(64) N-(4-{[5-({4-[{[(6-methyl-3-pyridinyl)amino]carbonyl}(phenyl)amino]-1-piperidinyl}methyl)-2-pyridinyl]methyl}phenyl)methanesulfonamide,
(65) N-{4-[5-({4-[{[(6-methyl-3-pyridinyl)amino]carbonyl}(phenyl)amino]-1-piperidinyl}methyl)-2-pyridinyl]phenyl}methanesulfonamide,
(66) N-{4-[(5-{[4-((3-methylphenyl){[(6-methyl-3-pyridinyl)amino]carbonyl}amino)-1-piperidinyl]methyl}-2-pyridinyl)oxy]phenyl}methanesulfonamide,
(67) N-[5-({[{1-[(6-{4-[(ethylsulfonyl)amino]phenoxy}-3-pyridinyl)methyl]-4-piperidinyl}(3-fluorophenyl)amino]carbonyl}amino)-2-fluorophenyl]acetamide,
(68) 2-fluoro-5-({[{1-[(6-{2-methyl-4-[(methylsulfonyl)amino]phenoxy}-3-pyridinyl)methyl]-4-piperidinyl}(phenyl)amino]carbonyl}amino)benzamide,
(69) 5-({[{1-[(6-{4-[(ethylsulfonyl)amino]phenoxy}-3-pyridinyl)methyl]-4-piperidinyl}(phenyl)amino]carbonyl}amino)-2-fluorobenzamide, and
(70) N-{4-[(5-{[4-((3-fluorophenyl){[(6-methyl-3-pyridinyl)amino]carbonyl}amino)-1-piperidinyl]methyl}-2-pyridinyl)oxy]phenyl}ethanesulfonamide, salts thereof, N-oxides thereof, solvates thereof, and prodrugs thereof are also preferable.

Processes for the Preparation of the Compound of the Present Invention:

The compound of the present invention represented by formula (I) can be prepared by methods which properly improved and combined known methods, such as methods described below, methods described in Examples or methods described in *Comprehensive Organic Transformations: A Guide to Functional Group Preparations*, 2nd Edition (Richard C. Larock, John Wiley & Sons Inc, 1999). In each method described below, a starting material can be used as a salt thereof. An example of the salt includes a salt of compound of formula (I) described above.

Among the compounds represented by formula (I), a compound wherein a spacer which is adjacent with ring D is —CH$_2$—, —CO— or —SO$_2$— can be prepared by alkylation, amidation or sulfonamidation by a compound represented by formula (I)x

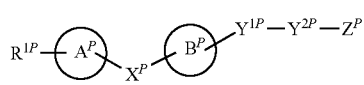

(1)

(wherein Z is hydroxy group or a leaving group (e.g., halogen atom, p-toluenesulfonyloxy group, methanesulfonyloxy group, trifluoro methanesulfonyloxy group etc.), Y$^{1P}$ is a bond or a spacer containing 1 or 2 atoms as a main chain, Y$^{2P}$ is —CH$_2$—, —CO— or —SO$_2$—, and R$^{1P}$, X$^P$, ring A$^P$ or ring B$^P$ have the same meanings as R$^1$, X, ring A and ring B respectively. With proviso that, carboxy group, hydroxy group, amino group or mercapto group in R$^{1P}$, X$^P$, Y$^{1P}$, Y$^{2P}$, ring A$^P$ or ring B$^P$ may be protected, if necessary. Other symbols have the same meaning as described above.) and a compound represented by formula (2)

(2)

(wherein R$^{2P}$ and ring D$^P$ have the same meanings as R$^2$ and D respectively. With proviso that, carboxy group, hydroxy group, amino group or mercapto group in R$^{2P}$ or ring D$^P$ may be protected, if necessary.), if necessary, followed by removal of the protecting group.

The alkylation is well known. For example, it may be carried out in an organic solvent (e.g., dimethylformamide, dimethylsulfoxide), in the presence of alkaline (e.g., potassium carbonate, sodium carbonate, triethylamine, etc.), and in the presence or absence of sodium iodide or potassium iodide at about 0 to 150° C.

The amidation is known. For example, it includes the method (1) via an acyl halide,
(2) via a mixed acid anhydride,
(3) using a condensing agent.

These methods are explained as follows.

(1) The method via an acyl halide may be carried out, for example, by reacting carboxylic acid with an acyl halide (e.g., oxalyl chloride or thionyl chloride) in an organic solvent (e.g., chloroform, dichloromethane, diethyl ether or tetrahydrofuran) or without a solvent at about −20° C. to reflux temperature. And then the obtained acyl halide derivative may be reacted with amine in an organic solvent (e.g., chloroform, dichloromethane, diethyl ether or tetrahydrofuran) in the presence of a base (e.g., pyridine, triethylamine, dimethylaniline, dimethylaminopyridine or diisopropylethylamine etc.) at about 0 to 40° C. As an alternative, the obtained acyl halide derivative may be reacted with amine in an organic solvent (e.g., dioxane, tetrahydrofuran) using an alkaline aqueous solution (e.g., sodium hydrogen carbonate, sodium hydroxide) at about −78 to 40° C.

(2) The method via a mixed acid anhydride may be carried out, for example, by reacting carboxylic acid with an acyl halide (e.g., pivaloyl chloride, p-toluenesulfonyl chloride or methanesulfonyl chloride) or an acid derivative (e.g., ethyl chloroformate or isobutyl chloroformate) in an organic solvent (e.g., chloroform, dichloromethane, diethyl ether, tetrahydrofuran) or without a solvent, in the presence of a base (e.g., pyridine, triethylamine, dimethylaniline, dimethylaminopyridine or diisopropylethylamine) at about 0 to 40° C. And then the obtained mixed acid anhydride derivative may be reacted with amine in an organic solvent (e.g., chloroform, methylene chloride, diethyl ether or tetrahydrofuran), at about 0 to 40° C.

(3) The method using a condensing agent may be carried out, for example, by reacting carboxylic acid with amine in an organic solvent (e.g., chloroform, dichloromethane, dimethylformamide, diethyl ether or tetrahydrofuran) or without a solvent, in the presence or absence of a base (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzothiazole (HOBt), at about 0 to 40° C.

The reaction described in (1), (2) and (3) may be carried out under an inert gas (e.g., argon, nitrogen) to avoid water in order to obtain a preferable result.

The sulfonamidation is well known. For example, it may be carried out by reacting sulfonic acid with acyl halide (e.g., oxalyl chloride or thionyl chloride, phosphorus pentachloride or phosphorus trichloride) in an organic solvent (e.g., chloroform, dichloromethane, dichloroethane, diethyl ether, tetrahydrofuran or tert-butyl methyl ether) or without a solvent at about −20° C. to reflux temperature. And then the obtained sulfonyl halide derivative may be reacted with amine in an organic solvent (e.g., chloroform, dichloromethane, diethyl ether or tetrahydrofuran) in the presence of a base (e.g., diisopropylethylamine, pyridine, triethylamine, dimethylaniline or dimethylaminopyridine etc.) at about 0 to 40° C.

The removal of the protecting group is known and may be carried out by following method.

The carboxyl-protective group includes, for example, methyl, ethyl, allyl, tert-butyl, trichloroethyl, benzyl (Bn) or phenacyl etc.

The protecting group of hydroxy includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), tert-butyldimethylsilyl (TBDMS), tert-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc) etc.

The protecting group of amino includes such as benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl (Fmoc), benzyl (Bn), p-methoxybenzyl, benzyloxymethyl (BOM) or 2-(trimethylsilyl)ethoxymethyl (SEM) etc.

The protective group of mercapto includes, for example, benzyl, methoxybenzyl, methoxymethyl (MOM), 2-tetrahydropyranyl (THP), diphenylmethyl and acetyl (Ac) etc.

With regard to the protective group for carboxyl, hydroxyl, amino and mercapto, there is no particular limitation to the above ones so far as it is a group which is able to be easily and selectively detached. For example, a deprotection reaction may be carried out by a method mentioned in "T. W. Greene, *Protective Groups in Organic Synthesis*, John Wiley & Sons Inc, 1999".

The reaction for removing the protective group for carboxyl, hydroxyl, amino or mercapto is known and its examples are as follows.

(1) a deprotection reaction by hydrolyzing reaction with an alkali;
(2) a deprotection reaction under an acidic condition;
(3) a deprotection reaction by hydrogenolysis;
(4) a deprotection reaction of silyl;
(5) a deprotection reaction using a metal; and
(6) a deprotection reaction using metal complex.

Those methods will be specifically illustrated as follows.
(1) A deprotection reaction using an alkali is carried out, for example, at about 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane etc.).
(2) A deprotection reaction under an acidic condition is carried out, for example, at about 0 to 100° C. in an organic acid (e.g., acetic acid, trifluoroacetic acid, methanesulfonic acid or p-toluenesulfonic acid), an inorganic acid (e.g., hydrochloric acid and sulfuric acid) or a mixture thereof (such as hydrogen bromide/acetic acid) in an organic solvent (such as dichloromethane, chloroform, dioxane, ethyl acetate and anisole etc.).
(3) A deprotection reaction by hydrogenolysis is carried out, for example, at about 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as dimethylformamide), water, ethyl acetate, acetic acid or a mixed solvent comprising two or more thereof].
(4) A deprotection reaction of silyl is carried out, for example, at about 0 to 40° C. using tetrabutylammonium fluoride in an organic solvent miscible with water (such as tetrahydrofuran and acetonitrile etc.).
(5) A deprotection reaction using metal is carried out, for example, at about 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).
(6) A deprotection reaction using a metal complex is carried out, for example, at about 0 to 40° C. using a metal complex [such as tetrakistriphenylphosphine palladium (II), bis(triphenylphosphine) palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-methylhexanoic acid) and/or an organic acid salt (such as sodium 2-ethylhexanoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

Apart from the above, the deprotection may also be effected, for example, according to the methods described in T. W. Greene, *Protective Groups in Organic Synthesis*, Wiley, New York, 1999.

As persons skilled in the art can easily understand that the aimed compound of the present invention is able to be easily produced by using appropriate ones among those deprotection reactions.

Among the compounds of the present invention represented by formula (I), a compound wherein $R^2$ is amino group which may have a substituent(s), i.e., a compound represented by formula (I-a)

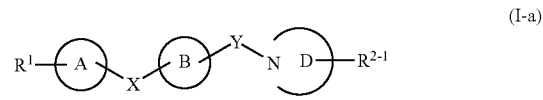

(I-a)

(wherein $R^{2-1}$ is amino group which may have a substituent(s) and other symbols have the same meanings as described above.) can be prepared by reductive amination of a compound represented by formula (3)

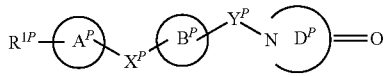

(wherein all symbols have the same meanings as described above.) and a compound represented by formula (4)

(wherein $R^{301}$ and $R^{302}$, which are the same or different, are each a hydrogen atom or have the same meanings as the "substituents" of the above-described "amino group which may have a substituent(s)", and other symbols have the same meanings as described above. With proviso that, carboxy group, hydroxy group, amino group or mercapto group in $R^{301}$ or $R^{302}$ may be protected, if necessary.), if necessary, followed by removal of the protecting group.

The reductive amination is well known. For example, it may be carried out with reducing agent (e.g., sodium triacetoxyborohydride or sodium cyanoborohydride) at about 0 to 40° C. in an organic solvent (e.g., dichloroethane, dichloromethane or dimethylformamide) in the presence or absence of tertiary amine (e.g., triethylamine or diisopropylethylamine), in the presence or absence of acetic acid.

The removal of the protecting group may be carried out by the above described method.

Among the compound of the present invention represented by formula (I), a compound wherein $R^2$ is

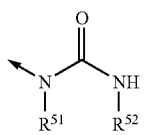

(wherein all symbols have the same meanings as described above.), i.e., a compound represented by formula (I-d)

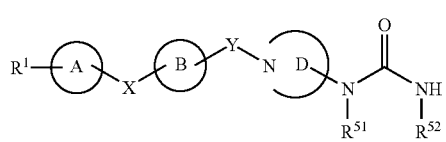

(wherein all symbols have the same meanings as described above.) can be prepared by a below reaction using a compound represented by formula (5)

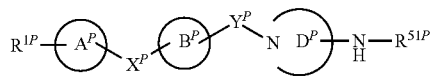

(wherein $R^{51P}$ has the same meaning as $R^{51}$ and other symbols have the same meanings as described above. With proviso that, carboxy group, hydroxy group, amino group or mercapto group in $R^{51P}$ may be protected, if necessary.) and a compound represented by (6)

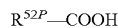

(wherein $R^{52P}$ has the same meaning as $R^{52}$ and other symbols have the same meanings as described above. With proviso that, carboxy group, hydroxy group, amino group or mercapto group in $R^{52P}$ may be protected, if necessary.), if necessary, followed by removal of the protecting group.

The reaction is well known. For example, it may be carried out in an organic solvent (e.g., N,N-dimethylformamide, toluene or tetrahydrofuran) with base (e.g., pyridine, triethylamine, dimethylaniline, dimethylaminopyridine or diisopropylethylamine) at about 20 to 120° C.

The removal of the protecting group may be carried out by the above described method.

Moreover, the compound represented by formula (I-d) can be prepared by a urea-forming reaction using the compound represented by formula (5) and a compound represented by formula (7)

(wherein the symbol has the same meaning as described above.), if necessary, followed by removal of the protecting group.

The reaction is well known. For example, it may be carried out in an organic solvent (e.g., tetrahydrofuran or N,N-dimethylformamiden) in the presence of triphosgene with base (e.g., triethylamine) at about 0 to 40° C. Moreover, it may be carried out in an organic solvent (e.g., dichloromethane or N,N-dimethylformamiden) in the presence of 1,1'-carbonylbis-1H-imidazole (CDI) with base (e.g., triethylamine or N-methylmorpholine) or without base at about 0 to 80° C.

The removal of the protecting group may be carried out by the above described method.

Among a compound of the present invention represented by formula (I), a compound wherein Y is methylene, i.e., a compound represented by formula (I-e)

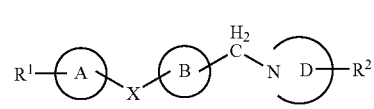

(wherein all symbols have the same meanings as described above) can be prepared by reductive amination of a compound represented by formula (8)

(wherein all symbols have the same meanings as described above.) and the compound represented by formula (2), if necessary, followed by removal of the protecting group.

The reductive amination and the removal of the protecting group may be carried out by the above described method.

Among the compounds represented by formula (I), a compound wherein at least one nitrogen atom is quaternary ammonium salt, i.e., a compounds of formula (I-2)

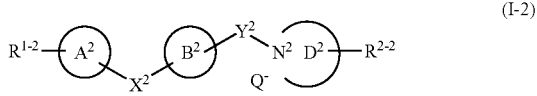

(wherein $R^{1-2}$, $R^{2-2}$, $X^2$, $Y^2$, ring $A^2$, ring $B^2$ and ring $D^2$ have the same meanings as $R^1$, $R^2$, X, Y, ring A, ring B and ring D respectively, and $N^2$ is nitrogen atom. With the proviso that, at least one nitrogen atom is quaternary ammonium salt, and $Q^-$ is a halogen ion.) can be prepared by reacting the compound of formula (I) with the compounds of formula (9)

(wherein $R^o$ is C1-8 alkyl or C1-8 alkyl substituted by phenyl, and Q is halogen.).

The reaction is well known, and it may be carried out, for example, in an organic solvent (acetone, dimethylformamide or methyl ethyl ketone etc.) at about 0 to 40° C.

Among the compounds of formula (I), a compound where at least one nitrogen is N-oxide, i.e., a compound of formula (I-3)

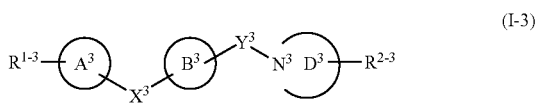

(wherein $R^{1-3}$, $R^{2-3}$, $X^3$, $Y^3$, ring $A^3$, ring $B^3$ and ring $D^3$ have the same meanings as $R^1$, $R^2$, X, Y, ring A, ring B and ring D respectively and $N^3$ is nitrogen atom. With the proviso that, at least one nitrogen atom represents N-oxide.) can be prepared by an oxidation of a compound of formula (I).

The oxidation is well known and it may be carried out, for example, in a suitable organic solvent (e.g., dichloromethane, chloroform, benzene, hexane or tert-butylalcohol) in the presence of an excessive oxidizing reagent (hydrogen peroxide, sodium periodate, acyl nitrite, sodium perborate, peroxidized acid (for example, 3-chloroperbenzoic acid or peracetic acid etc.), OXONE (brand name, OXONE is an abbreviation for potassium peroxymonosulfate.), potassium permanganate or chromic acid etc.) at about 20 to 60° C.

The compound of the present invention can be prepared by these reactions or reactions modified a part of them.

Other starting compounds or compounds used as reagent are known compounds can be prepared easily by combination of known methods, for example the methods described in *Comprehensive Organic Transformations: A Guide to Functional Group Preparations,* 2nd Edition (Richard C. Larock, John Wiley & Sons Inc, 1999) or Elmer J. Rauckman et al., *J. Org. Chem.,* vol. 41, No. 3, 1976, p 564-565 etc.

In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene or polyethyleneglycol etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

In a reaction using polystyrene resin of the specification, the obtained products may be purified by conventional techniques. For example, the purification may be carried out by rinsing them with a solvent (dimethylformamide, dichloromethane, methanol, tetrahydrofuran, toluene, acetic acid/toluene, etc.) more than once.

Toxicity:

The toxicity of the compound represented by formula (I), the salt thereof, the N-oxide thereof or the solvate thereof, or the prodrug thereof (hereinafter referred to as "the compound of the present invention") is very low and therefore it may be considered safe for pharmaceutical use.

Application to Pharmaceuticals:

The compound of the present invention has good solubility and absorbability. And the compound of the present invention has a week inhibitory activity against drug-metabolizing enzyme. These nature are the physical, chemical, and pharmaceutical property required to drugs, and the compound of the present invention have the proper conditions to an excellent drug [Ref. (*The Merck Manual of Diagnosis and Therapy* (17th Ed), Merck & Co.)].

It can be assessed that the compound of the present invention is useful as a drug by various experimental methods described below, methods described in Biological Examples, and their methods which properly improved. It can be also easily assessed that the compound of the present invention has a good pharmacokinetic property such as a length of serum half-life, a stability in the gastrointestinal tract, an absorption of oral preparations, bioavailability, etc. by known methods, for example, a method described in "*Yakubutsu bioavailability* (*Hyouka to kaizen no kagaku*), Jul. 6, 1998, Gendaiiryou-sha", etc.

(I) Evaluation Experiment of an Inhibitory Activity Against Drug-Metabolizing Enzymes of the Compound of the Present Invention (i) Inhibitory Activity Against Human CYP2C9

Inhibitory activity against human CYP2C9 of the compound of the present invention can be evaluated by a method of Sato et al. (*Yakubutsudotai* (*Xenobio. Metabol. and Dispos.*), 16(2), 115-126 (2001)), which is improved in assaying accuracy and/or assaying sensitivity.

(ii) Inhibitory Activity Against Human CYP3A4

Inhibitory activity against human CYP3A4 of the compound of the present invention can be evaluated by an improved method described in *Drug Metabolism and Disposition,* Vol. 28(12), 1440-1448 (2000).

For example, a reaction solution consisted of potassium phosphate buffer (pH7.4) (final concentration: 200 mM), magnesium chloride hexahydrate (final concentration: 5 mM), substrate (7-benzyloxyquinoline (7-BQ), final concentration: 40 μM), and expression system microsome (Daiichikagakuyakuhin, final concentration: 0.25 mg/mL) is prepared. 100 μL of the reaction solution is dispensed in 96-well plate, and added by 50 μL of an aqueous solution containing test a compound and 0.8% acetonitrile, to carry out 10 minutes of preincubation at 37° C. 50 μL of a reduced nicotinamide adenine dinucleotide phosphate (NADPH, 4 mM) is added to initiate a reaction. The fluorescence intensity of each well is measured at the time when NADPH is added and after incubated for 30 minutes. Excitation wavelength at 409 nm and emission wavelength at 530 nm of quinolinol, which is metabolite of substrate, is measured. Inhibition ratio (%) of the test compound is calculated by the following calculation formula to obtain $IC_{50}$ value.

Inhibition ratio(%)=[1-{(measured value when a test compound is added)−(blank value)/(control value−blank value)}]×100

(II) Evaluation Experiment of a Toxicity of the Compound of the Present Invention
(i) Single Acute Toxicity Test in Rat The test compound is administered to six-week Crj:CD (SD) rat by single intravenous dose or single oral administration. Toxicity can be evaluated by contrast with value at no addition of the test compound. Basic evaluation of toxicity can be done by, for example, observation of performance status or locomotor activity, etc.
(ii) Evaluation of the Activity of the Compound of the Present Invention Against hERG $I_{Kr}$ Current According to the report by Zou et al. (*Biophys. J.*, Vol. 74, 230-241 (1998)), using HEK293 cell overexpressed of human ether-a-go-go-related gene (hERG), max tale current of hERG $I_{Kr}$ current induced by depolarization pulse followed by repolarization pulse is measured by patch-clamp recording. Rate of change (inhibition rate) is calculated by comparison max tale current between before addition of the test compound and 10 minutes after. The influence of the test compound against hERG $I_{Kr}$ current can be evaluated by the inhibition rate The compounds of the present invention has the antagonistic activity against chemokine receptor, especially CCR5 in animal included human, especially human, so they are useful in preventing and/or treating CCR5-related diseases, for example, various inflammatory diseases (asthma, nephritis, nephropathy, hepatitis, arthritis, rheumatoid arthritis, rhinitis, conjunctivitis, inflammatory bowel disease such as ulcerative colitis, etc.), immunological diseases (autoimmune diseases, rejection in organ transplantation (rejection of graft of solid organ, rejection of graft of pancreatic islet cells in therapy for diabetes, GVHD (graft-versus-host disease), etc.), immunosuppression, psoriasis, multiple sclerosis, etc.), infectious diseases (infection with human immunodeficiency virus, acquired immunodeficiency syndrome, infection with RSV, etc.), allergic diseases (atopic dermatitis, urticaria, allergic bronchopulmonary aspergillosis, allergic eosinophilic gastroenteritis, etc.), cardiovascular diseases (arteriosclerosis, ischemic reperfusion injury, etc.), acute respiratory distress syndrome, shock accompanying bacterial infection, diabetes, cancer metastasis and so on.

The compounds of the present invention has the inhibitory activity against cell migration in animal included human, especially human, so they are useful in preventing and/or treating various inflammatory diseases (asthma, nephritis, nephropathy, hepatitis, arthritis, rheumatoid arthritis, rhinitis, conjunctivitis, inflammatory bowel disease such as ulcerative colitis, etc.), immunological diseases (autoimmune diseases, rejection in organ transplantation (rejection of graft of solid organ, rejection of graft of pancreatic islet cells in therapy for diabetes, GVHD, etc.), immunosuppression, psoriasis, multiple sclerosis, etc.), infectious diseases (infection with human immunodeficiency virus, acquired immunodeficiency syndrome, infection with RSV, etc.), allergic diseases (atopic dermatitis, urticaria, allergic bronchopulmonary aspergillosis, allergic eosinophilic gastroenteritis, etc.), cardiovascular diseases (arteriosclerosis, ischemic reperfusion injury, etc.), acute respiratory distress syndrome, shock accompanying bacterial infection, diabetes, cancer metastasis and so on.

For the purpose above described, the compounds of the present invention may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered for example, in the form of solid for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol such as ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and vaginal suppositories which comprise one or more of the active compound(s) and may be prepared by methods known per se.

Sprays may comprise additional substances other than diluents, used commonly, stabilizers such as sodium hydrogensulfite and buffers capable of imparting isotonicity, for example, isotonic buffers such as sodium chloride, sodium citrate or citric acid.

The compounds of the present invention may be used together with other drugs, for example, preventive and/or treating agent(s) for HIV infection (particularly agents for prevention and/or treatment for AIDS), or agent(s) for rejection in organ transplantation and/or autoimmune diseases. In that case, the drug as such may be mixed with pharmacologically acceptable excipient, binder, disintegrating agent, lubricant, stabilizer, solubilizer, diluent, etc. either separately or simultaneously to make into a pharmaceutical preparation and that can be administered either orally or parenterally as a pharmaceutical composition for prevention and/or treatment of HIV infection rejection in organ transplantation and/or autoimmune diseases.

The compounds of the present invention have an infection inhibiting activity to HIV which acquired resistance to other agents for preventive and/or treating HIV infection (particularly agents for prevention and/or treatment for AIDS). Therefore, it is also able to be used for HIV-infected patients to whom other agents for preventive and/or treating HIV infection are no longer effective. In that case, although the compound of the present invention may be used solely, it may be also used together with agents for preventive and/or treating HIV infection where infected HIV strain acquired resistance or with other drugs.

The present invention covers the combination of the compounds of the present invention with drugs which do not inhibit the HIV infection whereby preventive and/or treating effect for HIV infection is enhanced as compared with a single preparation.

Examples of other agent for preventive and/or treating HIV infection used for a combination with the compounds of the present invention are reverse transcriptase inhibitor, protease inhibitor, chemokine antagonist (such as CCR2 antagonist, CCR3 antagonist, CCR4 antagonist, CCR5 antagonist CXCR3 antagonist and CXCR4 antagonist), integrase inhibitor, fusion inhibitor, antibody to surface antigen of HIV and vaccine of HIV.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil) or PMPA (brand name: Tenofovir) etc. and (2) nonnucleoside reverse transcriptase inhibitors: nevirapine (brand name: Viramune), delavirdine (brand name: Rescriptor), efavirenz (brand name: Sustiva, Stocklin) or capravirine (AG1549) etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir etc.

As chemokine antagonists, internal ligand of chemokine receptor, its derivatives, its non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC etc.

The derivatives of internal ligand are concretely, AOP-RANTES, Met-SDF-1α, Met-SDF-1β etc.

Antibodies of chemokine receptor are concretely, Pro-140 etc.

CCR2 antagonists are concretely written in specification of WO99/07351, WO99/40913, WO00/46195, WO00/46196, WO00/46197, WO00/46198, WO00/46199, WO00/69432 or WO00/69815 or in Bioorg. Med. Chem. Lett., 10, 1803 (2000) etc.

CCR3 antagonists are written in, for example, specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088 etc.

CCR5 antagonists are, for example, TAK-779, SCH-351125 (SCH-C), SCH-417690 (SCH-D), UK-427857, GW873140 (ONO-4128), TAK-220 etc. Moreover, it includes compounds written in, for example, specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO00/59503, WO00/76933, WO98/25605, WO99/04794, WO99/38514, Bioorg. Med. Chem. Lett., 11, 2663 (2003), Curr. Med. Chem. Anti-Infective Agents, 4, 133 (2005), Current Opinion in Pharmacology, 4, 447 (2004), or Current Opinion in Investigational Drugs, 5, 851 (2004), etc.

CXCR3 antagonists are written in, for example, specification of WO01/16114, WO02/083143, WO02/085862, U.S. Pat. No. 6,469,002, or WO03/101970, etc.

CXCR4 antagonists are, for example, AMD-3100, AMD-070, T-22, KRH-1120, KRH-1636, KRH-2731 or the compounds written in specification of WO00/66112 etc.

Integrase inhibitors are Equisetin, Temacrazine, PL-2500, V-165, NSC-618929, L-870810, L-708906 analog, S-1360, or 1838, etc.

Fusion inhibitors are concretely, T-20 (Pentafuside) and T-1249 etc.

The examples of combination agents written above are intended to illustrate the present invention, but do not limit them.

The typical examples of the usual the dosage level in clinical trials of reverse transcriptase inhibitors or protease inhibitors written below are intended to illustrate the present invention, but do not limit them.

Zidovudine: 100 mg capsule, 200 mg per dose, 3 times per day;
   300 mg tablet, 300 mg per dose, twice per day;
didanosine: 25-200 mg tablet, 125-200 mg per dose, twice per day;
zalcitabine: 0.375-0.75 mg tablet, 0.75 mg per dose, 3 times per day;
stavudine: 15-40 mg capsule, 30-40 mg per dose, twice per day;
lamivudine: 150 mg tablet, 150 mg per dose, twice per day;
abacavir: 300 mg tablet, 300 mg per dose, twice per day;
nevirapine: 200 mg tablet, 200 mg per dose, once per day for 14 days and then twice per day;
delavirdine: 100 mg tablet, 400 mg per dose, 3 times per day;

efavirenz: 50-200 mg capsule, 600 mg per dose, once per day;
indinavir: 200-400 mg capsule, 800 mg per dose, 3 times per day;
ritonavir: 100 mg capsule, 600 mg per dose, twice per day;
nelfinavir: 250 mg tablet, 750 mg per dose, 3 times per day;
saquinavir: 200 mg capsule, 1,200 mg per dose, 3 times per day;
amprenavir: 50-150 mg tablet, 1,200 mg per dose, twice per day.

Examples of other agent for preventive and/or treating rejection in organ transplantation used for a combination with the compounds of the present invention are immunosuppressants.

Examples of the immunosuppressant include tacrolimus (FK506), cyclosporin, sirolimus (rapamycin), corticosteroids, azathioprine, mycophenolate mofetil, FTY-720, cyclophosphamide, or cell-surface ligand antibody, etc.

Examples of the cell-surface ligand antibody include Atgam, Thymoglobulin, Simulect, Zanapax, or Orthoclone, etc.

Examples of other agent for preventive and/or treating autoimmune diseases used for a combination with the compounds of the present invention are nonsteroidal antiinflammatory drug, disease modifying anti-rheumatic drug (DMARDs, slow-acting anti-rheumatic drug), steroids, immunosuppressant agent, antiinflammatory enzyme preparations, chondroprotective agents, T-cell inhibitors, TNFα inhibitor (include protein preparation such as anti-TNFα antibody), prostaglandin synthase inhibitor, IL-1 inhibitor, IL-6 inhibitor (include protein preparation such as anti-IL-6 receptor antibody), interferon gamma agonists, prostaglandins, phosphodiesterase inhibitor, metalloproteinase inhibitor, etc.

Examples of the nonsteroidal antiinflammatory drug include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, napmetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axethyl, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, or antipyrine system antipyretics, etc.

Examples of the disease modifying anti-rheumatic drug (DMARDs, slow-acting anti-rheumatic drug) include, for example, gold thioglucose, aurothiomalate sodium, auranofin, actarit, D-penicillamine preparations, lobenzarit disodium, bucillamine, hydroxychloroquine, salazosulfapyridine, methotrexate, or leflunomide, etc.

Examples of the steroids for external application include clobetasol propionate, diflorasone acetate, fluocinonide, monometasone furancarboxylate, betamesone dipropionate, betamesone butyropropionate, betamesone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone acetopropionate, deprodone propionate, prednisolone valeroacetate, fluocinolone acetonide, beclometasone dipropionate, triamcinonide acetonide, flumethasone pivalate, prednisolone, beclometasone propionate, and fludroxycortide, etc.

Examples of the steroids for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredon acetate, methyl prednisolone, methyl prednisolone acetate, methyl prednisolone sodium succinate, triamcinolon, triamcinolon acetate, triamcinonolon acetonide, dexamethasone, dexamethasone acetate, dexamethasone sodium phosphate, dexamethasone palmitate, paramethasone acetate, and betamethasone, etc.

Examples of the steroids as an inhalant include beclomethasonepropionate, fluticasone propionate, budesonide, flunisolide, triamcinolon, ST-126P, ciclesonide, dexamethasone palomitionate, monometasone furancarboxylate, prasterone sulfonate, deflazacort, methylprednisolone suleptanate, and methylprednisolone sodium succinate, etc.

Examples of the antiinflammatory enzyme preparations include, for example, lysozyme chloride, bromelain, pronase, serrapeptase, or streptokinase-streptodornase, etc.

Examples of the chondroprotective agents include, for example, hyaluronate sodium, glucosamine, chondroitin sulfate, and glucosaminoglycan polysulfate, etc.

Examples of TNFα inhibitor (include protein preparation such as anti-TNFα antibody) include, for example, infliximab, adalimumab, or etanercept, etc.

Examples of the prostaglandin synthase inhibitor include, for example, salazosulfapyridine, mesalazine, olsalazine, 4-aminosalicylic acid, JTE-522, auranofin, carprofen, diphenpyramid, flunoxaprofen, flurbiprofen, indomethacin, ketoprofen, lornoxicam, loxoprofen, Meloxicam, oxaprozin, parsalmide, piproxen, piroxicam, piroxicam betadex, piroxicam cinnamate, tropine indomethacinate, zaltoprofen, and pranoprofen, etc.

Examples of IL-1 inhibitor (include protein preparation such as human IL-1 receptor antagonist) include, for example, anakinra, etc.

Examples of IL-6 inhibitor (include protein preparation such as anti-IL-6 receptor antibody) include, for example, MRA, etc.

Examples of the prostaglandins (hereinafter abbreviated as "PG") include PG receptor agonist, and PG receptor antagonist, etc. Examples of the PG receptor include PGE receptor (EP1, EP2, EP3, and EP4), PGD receptor (DP, CRTH2), PGF receptor (FP), PGI receptor (IP), or TX receptor (TP), etc.

Examples of the phosphodiesterase inhibitor include, for example, rolipram, cilomilast (trade name: Ariflo), Bay 19-8004, NIK-616, roflumilast (BY-217), cipamfylline (BGL-61063), atizolam (CP-80633), SCH-351591, YM-976, V-11294A, PD-168787, D-4396, IC-485, or ONO-6126 as PDE-4 inhibitor, etc.

Examples of other agent for preventive and/or treating other allergic diseases, for example, asthma used for a combination with the compounds of the present invention are steroids, $\beta_2$ adrenoreceptor stimulant, leukotriene receptor antagonist, thromboxane synthetase inhibitor, thromboxane $A_2$ receptor antagonist, mediator releasing inhibitor, antihistamines, xanthine derivatives, anticholinergic agent, cytokine inhibitor, prostaglandins, forskolin, phosphodiesterase inhibitor, elastase inhibitor, metalloproteinase inhibitor, expectorant, and antibiotic.

Examples of the $\beta_2$ adrenoreceptor stimulant include fenoterol hydrobromide, salbutamol sulfate, terbutaline sulfate, formoterol fumarate, salmeterol xinafoate, isoprotenol sulfate, orciprenalin sulfate, chloroprenalin sulfate, epinephrine, trimetoquinol hydrochloride, hexoprenalinmesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meradrin tartrate, AR-C68397, levosalbutamol, R,R-formoterol, KUR-1246, KUL-7211, AR-C89855, and S-1319, etc.

Examples of the leukotriene receptor antagonist include pranlukast hydrate, montelukast, zafirlukast, seratrodast, MCC-847, KCA-757, CS-615, YM-158, L-740515, CP-195494, LM-1484, RS-635, A-93178, S-36496, BIIL-284, and ONO-4057, etc.

Examples of the thromboxane synthetase inhibitor include ozagrel hydrochloride, and imitrodast sodium, etc.

Examples of the thromboxane $A_2$ receptor antagonist include seratrodast, ramatroban, domitroban calcium dihydrate, and KT-2-962, etc.

Examples of the mediator releasing inhibitor include tranilast, sodium cromoglicate, anlexanox, repirinast, ibudilast, tazanolast, and pemilolast potassium, etc.

Examples of the antihistamines include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acribastin, etc.

Examples of the xanthine derivatives include aminophylline, thoeophyline, doxophylline, cipamfylline, and diprophilline, etc.

Examples of the anticholinergic agent include ipratropium bromide, oxitropium bromide, flutropium bromide, temiverine, tiotropium bromide, and revatropate (UK-112166), etc.

Examples of the cytokine inhibitor include suplatast tosilate (trade name: IPD), etc.

Examples of the elastase inhibitors include ONO-5046, ONO-6818, MR-889, PBI-1101, EPI-HNE-4, R-665, ZD-0892, ZD-8321, GW-311616, and AE-3763 etc.

Examples of the expectorant include foeniculated ammonia spirit, sodium hydrogencarbonate, bromhexine hydrochloride, carbocisteine, ambroxol hydrochloride, sustained release ambroxol hydrochloride, methylcysteine hydrochloride, acetyl cysteine, L-ethylcysteine hydrochloride, and tyloxapol, etc.

Examples of antibiotics include cefuroxime sodium, meropenem trihydrate, netilmicin sulfate, sisomicin sulfate, ceftibuten, PA-1806, IB-367, tobramycin, PA-1420, doxorubicin, astromicin sulfate, or cefetamet pivoxil hydrochloride, etc.

Examples of antibiotics as an inhalant include PA-1806, IB-367, tobramycin, PA-1420, doxorubicin, astromicin sulfate, or cefetamet pivoxil hydrochloride, etc.

The other pharmaceutical which supplement and/or enhance the prevention and/or treatment effect of the compound of the present invention is not limited to examples as described above. With regard to other pharmaceuticals which supplement and/or enhance the prevention and/or treatment effect of the compound of the present invention, not only that which has been found up to now but also that which will be found in future on the basis of the above-mentioned mechanism are included.

The nomenclature of compounds of the present invention is described below.

All the compounds described in the present specification were named using ACD/Name (registered trademark, Advanced Chemistry Development Inc.) or ACD/Name Batch (registered trademark, Advanced Chemistry Development Inc.), or named according to IUPAC nomenclature system. For example, a compound represented by

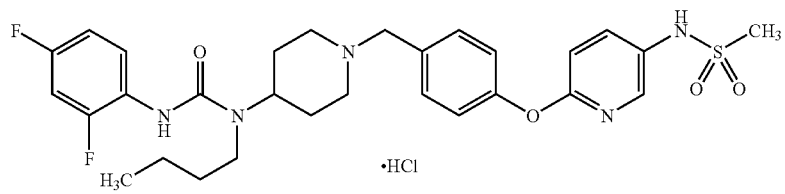

was named N-[6-(4-{[4-(butyl{[(2,4-difluorophenyl)amino]carbonyl}amino)-1-piperidinyl]methyl}phenoxy)-3-pyridinyl]methanesulfonamide hydrochloride.

In the present specification, "hydrochloride (or dihydrochloride)" means either hydrochloride or dihydrochloride, so it does not represent a mixture of hydrochloride and dihydrochloride. In the present specification, "dihydrochloride (or trihydrochloride)" means either dihydrochloride or trihydrochloride, so it does not represent a mixture of dihydrochloride and trihydrochloride. ".HCl or 2HCl" in the structure described in the present specification means either HCl or 2HCl, so it does not represent a mixture of HCl and 2HCl. ".2HCl or 3HCl" in the structure described in the present specification means either 2HCl or 3HCl, so it does not represent a mixture of 2HCl and 3HCl.

EFFECT OF THE INVENTION

The compounds of the present invention represented by formula (I) has the antagonistic activity against chemokine receptor, especially CCR5, so they are useful in preventing and/or treating CCR5-related diseases.

The fact that the compound of the present invention has CCR5 antagonism is demonstrated, for example, by the following experiment. The total operation is based on the basic genetic engineering to prepare gene highly expressing cells, and the ordinary methods are utilized. Also, in the assaying method of the present invention, in order to evaluate the compound of the present invention, accuracy of measurement and/or sensitivity of measurement is improved as described below. The detailed experimental methods are shown below.

(I) Inhibition test on the binding of RANTES to CCR5
(1) Isolation of human CCR5 gene Human placental cDNA is prepared using Marathon cDNA amplification kit (Clontech). PCR primers hCCR5Xbal-F1: 5'-AGCTAGTCTAGATCCGTTCCCCTACAA-GAAACTCTCC-3' (SEQ ID NO:1) and hCCR5Xbal-R1: 5'-AGCTAGTCTAGAGTGCACAACTCT-GACTGGGTCACCA-3' (SEQ ID NO:2) are designed based on the sequence of GenBank U54994 (SEQ ID NO:3).

Using the human placental cDNA as the template and using Ex Taq (Takara), PCR reaction (2 minutes at 95° C.→(30 seconds at 95° C., 45 seconds at 60° C., 1 minute at 72° C.)×35 times) is carried out. The thus amplified PCR product is subjected to a 1% agarose gel electrophoresis, purified using QIAquick Gel Extraction Kit (QUTAGEN) and then digests with a restriction enzyme XbaI. The digested fragments are ligated to an expression vector pEF-BOS-bsr using DNA Ligation Kit Ver. 2 (Takara) and transformed into *Escherichia coli* DHSα. By preparing the resulting plasmid pEF-BOS-bsr/hCCR5, its DNA sequence is verified.

(2) Culturing of CHO Cell

CHO-dhfr(−) is cultured using Ham's F-12 (containing fetal bovine serum (10%), penicillin (50 U/ml) and streptomycin (50 mg/ml)). Also, the transduced cell is cultured by adding blasticidin (5 mg/ml) to the above medium.

(3) Transduction into CHO Cell

The plasmid pEF-BOS-bsr/hCCR5 is transduced into the CHO-dhfr(−) cell using DMRIE-C reagent (Gibco BRL). After 48 hours, the medium is replaced with a medium containing 5 mg/ml of blasticidin to carry out the selection, thereby establishing a stably over-expressing cell.

(4) Inhibition Test on the Binding of Chemokine (RANTES, MIP-1α and MIP-1β) to CCR5 (activity of chemokine to induce transient increase of Ca Ion).

The thus established stable CHO cell overexpressing human CCR5 (CCR5/CHO cell) is suspended in Ham's F-12 medium containing FBS (10%) and seeded at a density of $3.0 \times 10^6$ cells/well into a 96-well plate. One day after culturing at 37° C., the culture supernatant is discarded, and Ham's F-12 medium (containing Fura-2AM (5 µM), Probenecid (2.5 mM) and HEPES (20 mM; pH 7.4)) is dispensed in 80 µl/well portions to carry out 1 hour of incubation at 37° C. under shaded condition. After washing twice with 1× Hanks/HEPES (20 mM; pH 7.4) solution, the same solution is dispensed in 100 µl/well portions. Each of the test compounds is added to the thus Fura-2AM-incorporated CCR5/CHO cell, and 3 minutes thereafter, a recombinant human CCR5 ligand (RANTES, MIP-1α or MIP-1β) (PeproTach) diluted with 1× Hanks/HEPES (20 mM; pH 7.4) solution is added thereto to a final concentration (Rantes: 10 nM; MIP-1α: 30 nM; MIP-1β: 30 nM). Transient increase in the intracellular $Ca^{2+}$ concentration induced by the human CCR5 ligand is measured using a $Ca^{2+}$ detector for 96 well use (Hamamatsu Photonics), and inhibition ratio (%) of the test compound is calculated by the following calculation formula.

Inhibition ratio=$(Ec-Ea)/Ec \times 100$

Ec: measured value of $Ca^{2+}$ transient increase by CCR5 ligand

Ea: measured value of $Ca^{2+}$ transient increase by CCR5 ligand when a test compound is added.

(II) Migration Test of Human CCR5 Expressing Cell (hCCR5-Ba/F3 Cell):

(1) Establishment of Human CCR5 Expressing Cell (1-A) Isolation of Human CCR5 Gene The isolation is carried out according to the method of the isolation of human CCR5 gene as described in the above method (I)-(1).

(1-B) Culturing of Ba/F3 Cell

Ba/F3 cells are statically cultured by using RMMI-1640 medium (Gibco BRL) containing antibiotics (Antibiotic-Antimycotic) (final concentration: penicillin G sodium (100 U/ml), streptomycin sulfate (100 µg/ml), amphotericin B (0.25 µg/ml) (Gibco BRL), fetal bovine serum (FBS) (10%), 2-mercaptoethanol (55 µM), mouse interlekin-3 (IL-3) (5 ng/ml) (Pepro Tech, Inc) in a carbon dioxide incubator (temperature: 37° C., $CO_2$ concentration: 5%, humidity: 95%). Exogenous gene stable hyperexpression cells are cultured in the above medium to which blasticidin (Kaken Pharmaceutical) is added to give a final concentration of 10 µg/ml.

(1-C) Transformation to Ba/F3 Cell

A plasmid for human CCR5 expression (pEF-BOS-bsr/hCCR5) is digested with AatII for linearization. The linearized plasmid is purified by QIA quick PCR Purification Kit (QIAGEN), and introduces into Ba/F3 cells by electroporation (Gene Pulser (BIO RAD), 960 µF/250V). The cells are seeded into a 96-well culture plate at a density of 1,000, 100, 10 cells/100 µl/well, and cultured for 48 hours. Then, blasticidin is added thereto to give a final concentration of 10 µg/ml, followed by cloning of a blasticidin-resistant cell line to thereby establish a stable clone overexpressing the transfected exogenous gene (hCCR5-Ba/F3 cell).

(1-D) Analysis of CCR5 Expression

The human CCR5 expression level in the clone obtained by the method described in the above (1-C) is detected with FAC Sort (trade name, Becton, Dickinson) by detecting the cells with a fluorescence isothiocyanate (FITC)-labeled anti-human CCR5 antibody (BD Pharmingen) and analyzed. In this connection, FITC-labeled mouse IgG2aκ (BD Pharmingen) is used as an isotype control antibody.

(2) Cell Migration Test

Influence of a test compound on the migration ability of the human CCR5 expressing Ba/F3 cell against RANTES, MIP-1α or MIP-1β is examined. First, 0.3 ml of 0 or 3 nM chemokine (RANTES, MIP-1α or MIP-1β)-containing medium is respectively added to the low room of Chemo T×96 well plate (Neuro Probe). Next, a filter (pore size: 5 µm) is set and a mixture solution ($1 \times 10^5$ cells/well) of the test compound and the CCR5-Ba/F3 cell prepared in advance is added at 65 µl. The test compound to be added is prepared by diluting it with 0.1% DMSO-containing medium to give a final concentration on the filter of 0, 0.01, 0.03, 0.1 or 0.3 µM. These cells are cultured in a $CO_2$ incubator (37° C., 5% $CO_2$, relative humidity: 95%) for 3 hours, and then the medium and unmigrated cells on the filter are eliminated. Furthermore, the filter is removed, the microplate is centrifuged (1,500 rpm, 10 min, RT) and the supernatant is removed by decantation. The cells on the microplate are suspended in 100 µl of a phosphate buffer (PBS), and 1/10 portion thereof is further diluted with 90 µl of PBS, moves on a white plate for fluorescence assay, and uses as an assay sample for migrated cell numbers (final: 100 µl/well).

Next, Cell Titer-Glo Reagent (trade name, Promega) which is previously prepared at room temperature is added to the above assay sample for migrated cell numbers (100 µl/well), followed by gently mixing (300 rpm, 2 min with KA-SCHUTTLER MTS4) for lysating the cells, the mixture is incubated at room temperature for 10 minutes, and the fluorescence is measured with wallac ARVO SX 1420 MULTILABEL COUNTER (trade name, Perkin Elmer) (detection by count/second).

The migrated cell numbers (naturally falling cell numbers) at a chemokine concentration of 0 nmol/l is used as the background, and the inhibition ratio of the test compound against the 0.1% DMSO control group is calculated.

The inhibition migration ratio (%) of the test compound is calculated by the following equation:

$$\text{Inhibition ratio} = \frac{(Ec - Ea)}{Ec} \times 100$$

Ec: (fluorescence measured value at the addition of 0.1% DMSO)−(fluorescence measured value of the naturally falling cells)

Ea: (fluorescence measured value at the addition of the test compound)−(fluorescence measured value of the naturally falling cells)

BEST MODE FOR CARRYING OUT THE INVENTION

The following Preparation Examples, Biological Examples and Formulation Examples are intended to illustrate the present invention, but do not limit them.

In chromatographic separations and TLC, the solvents in parenthesis show the eluting and developing solvents and the ratios of the solvents used are by volume.

NMR is a measured value of $^1$H NMR. The solvents in parenthesis in NMR show the solvents used for measurement.

PREPARATION EXAMPLE

Example 1

N-[6-(4-formylphenoxy)pyridin-3-yl]methanesulfonamide

{4-[(5-nitropyridin-2-yl)oxy]phenyl}methanol was subjected to reduction of nitro group by using zinc and acetic acid, the obtained compound reacted with methanesulfonyl chloride in pyridine, and the obtained compound was subjected to oxidation by using manganese dioxide to give the title compound having the following physical data.

TLC: Rf 0.67 (dichloromethane:methanol=9:1);

NMR (CDCl$_3$): δ 3.04, 6.56, 7.05, 7.29, 7.80, 7.94, 8.08, 9.99.

Example 2

N-butyl-N'-(2,4-difluorophenyl)-N-piperidin-4-ylurea hydrochloride

To a solution of tert-butyl 4-(butylamino)piperidin-1-carboxylate (1 g) in dimethylacetamide (13 ml) was added triethylamine (1.6 ml) and 2,4-difluorophenyl isocyanate (907 mg). The reaction mixture was stirred for 5 minutes at room temperature. To reaction mixture was added a saturated aqueous solution of sodium hydrogen carbonate, and extracted with ethyl acetate. The extract was washed with water and brine, dried over anhydrous sodium sulfate, and concentrated. To the solution of the obtained compound (1.28 g) in ethyl acetate (2 ml) was added 4N hydrogen chloride in ethyl acetate solution (10 ml). The reaction mixture was stirred for 20 minutes at room temperature, and concentrated. The obtained residue was washed with tert-butyl methyl ether, dried to give the title compound having the following physical data.

TLC: Rf 0.52 (dichloromethane:methanol:acetic acid=5:1:0.1);

NMR (CD$_3$OD): δ 0.99, 1.34-1.47, 1.60-1.71, 1.95-2.01, 2.08-2.22, 3.03-3.13, 3.27-3.34, 3.44-3.50, 4.13, 7.00, 7.37, 8.01.

Example 3

N-[6-(4-{[4-(butyl{[(2,4-difluorophenyl)amino]carbonyl}amino)-1-piperidinyl]methyl}phenoxy)-3-pyridinyl]methanesulfonamide hydrochloride (or dihydrochloride)

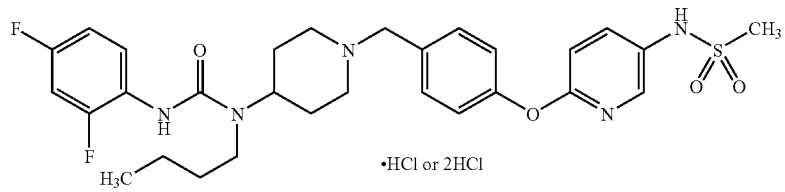

To a solution of the compound prepared in Example 1 (95 mg) and the compound prepared in Example 2 (80 mg) in dimethylformamide (1.5 ml) was added acetic acid (0.15 ml) and sodium triacetoxyborohydride (116 mg). The reaction mixture was stirred for 18 hours at room temperature. The reaction mixture was added a saturated aqueous solution of sodium hydrogen carbonate, and extracted with ethyl acetate. The extract was dried over anhydrous sodium sulfate, and concentrated. The obtained residue was purified by column chromatography on silica gel (ethyl acetate:methanol=10:1). To a solution of the obtained compound was added 4N hydrogen chloride in ethyl acetate solution. The reaction mixture was concentrated to give the title compound (115 mg) having the following physical data.

TLC: Rf 0.44 (dichloromethane:methanol=9:1);

NMR (CD$_3$OD): δ 0.98, 1.35-1.48, 1.58-1.70, 1.95-2.08, 2.18-2.34, 3.00, 3.08-3.20, 3.25-3.34, 3.57-3.65, 4.19, 4.34, 6.89-7.03, 7.09, 7.25, 7.38, 7.60, 7.85, 8.06.

Examples 3(1)-3(107)

By the same procedure as described in Example 3 using the corresponding amine compounds and the corresponding aldehyde compounds, the following compounds of the present invention were obtained.

Example 3(1)

N-{4-[(6-{[4-(butyl{[(2,4-difluorophenyl)amino]carbonyl}amino)-1-piperidinyl]methyl}-3-pyridinyl)oxy]phenyl}methanesulfonamide hydrochloride (or dihydrochloride)

TLC: Rf 0.30 (chloroform:methanol=10:1);

NMR (CD$_3$OD): δ 0.99, 1.30-1.50, 1.60-1.80, 1.90-2.10, 2.20-2.40, 2.97, 3.20-3.40, 3.60-3.70, 4.20, 4.47, 6.92-7.02, 7.09-7.12, 7.31-7.40, 7.47-7.58, 8.45.

Example 3(2)

N-{4-[4-({4-[{[(2-hydroxybutyl)amino]carbonyl}(phenyl)amino]-1-piperidinyl}methyl)phenoxy]phenyl}methanesulfonamide hydrochloride TLC: Rf 0.41 (dichloromethane:methanol=9:1);
NMR (CD$_3$OD): δ 0.89, 1.20-1.42, 1.55-1.70, 2.05-2.17, 2.95, 3.08-3.28, 3.37-3.50, 4.21, 4.51, 7.00, 7.02, 7.21-7.30, 7.41, 7.44-7.55.

Example 3(3)

N-{4-[4-({4-[butyl({[1-(2-hydroxyethyl)-1H-pyrazol-4-yl]amino}carbonyl)amino]-1-piperidinyl}methyl)phenoxy]phenyl}methanesulfonamide dihydrochloride TLC: Rf 0.40 (dichloromethane:methanol=9:1);
NMR (CD$_3$OD): δ 0.97, 1.31-1.42, 1.50-1.72, 1.91-2.01, 2.15-2.31, 2.95, 3.10-3.32, 3.51-3.60, 3.87, 4.23, 4.30, 4.35, 7.03, 7.06, 7.29, 7.53, 7.98, 8.12.

Example 3(4)

5-[({butyl[1-(4-{4-[(methylsulfonyl)amino]phenoxy}benzyl)-4-piperidinyl]amino}carbonyl)amino]-2,4-difluoro-N-methylbenzamide hydrochloride

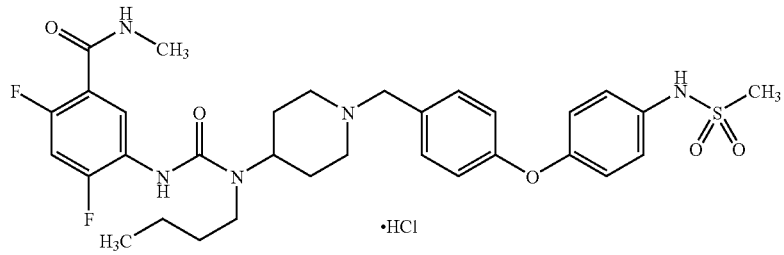

TLC: Rf 0.90 (chloroform:methanol=4:1);
NMR (CD$_3$OD): δ 0.97, 1.30-1.50, 1.60-1.70, 1.90-2.10, 2.10-2.30, 2.91, 2.95, 3.00-3.20, 3.20-3.40, 3.50-3.60, 4.15, 4.29, 7.02-7.09, 7.12, 7.29, 7.50, 7.78.

Example 3(5)

N-{4-[4-({4-[{[(trans-4-hydroxycyclohexyl)amino]carbonyl}(phenyl)amino]-1-piperidinyl}methyl)phenoxy]phenyl}methane sulfonamide hydrochloride TLC: Rf 0.46 (dichloromethane:methanol=9:1);
NMR (CD$_3$OD): δ 1.00-1.18, 1.21-1.37, 1.55-1.68, 1.71-1.89, 2.04-2.15, 2.95, 3.04-3.18, 3.38-3.54, 4.21, 4.60, 6.98-7.07, 7.18-7.23, 7.28, 7.41, 7.45-7.53.

Example 3(6)

N-[4-(4-{[4-(3-butenyl{[(2-hydroxybutyl)amino]carbonyl}amino)-1-piperidinyl]methyl}phenoxy)phenyl]methanesulfonamide hydrochloride TLC: Rf 0.51 (dichloromethane:methanol=9:1);
NMR (CD$_3$OD): δ 0.95, 1.30-1.58, 1.90-2.00, 2.07-2.24, 2.28-2.38, 2.95, 3.02-3.35, 3.50-3.60, 4.12, 4.28, 5.05, 5.11, 5.81, 7.03, 7.06, 7.29, 7.50.

Example 3(7)

N-butyl-N'-(2,4-difluorophenyl)-N-(1-{4-[4-(4-morpholinylsulfonyl)phenoxy]benzyl}-4-piperidinyl)urea hydrochloride TLC: Rf 0.60 (dichloromethane:methanol=20:1);
NMR (CD$_3$OD): δ 0.99, 1.39-1.43, 1.60-1.70, 2.00-2.05, 2.16-2.30, 2.94-2.97, 3.06-3.28, 3.29-3.36, 3.52-3.61, 3.69-3.72, 4.13, 4.23, 6.90-7.03, 7.20, 7.23, 7.37, 7.58, 7.78.

Example 3(8)

N-butyl-2-(2,4-difluorophenyl)-N-[1-(4-{4-[(methylsulfonyl)amino]phenoxy}benzyl)-4-piperidinyl]acetamide hydrochloride TLC: Rf 0.41 (chloroform:methanol=10:1);
NMR (d$_6$-DMSO): δ 0.92, 1.20-1.40, 1.40-1.60, 1.70-1.90, 2.20-2.40, 2.90-3.10, 2.97, 3.15-3.30, 3.30-3.50, 3.71, 4.05-4.30, 6.94-7.09, 7.12-7.25, 7.57, 9.34, 10.50.

Example 3(9)

N-{4-[(5-{[4-(butyl{[(1-methyl-1H-pyrazol-4-yl)amino]carbonyl}amino)-1-piperidinyl]methyl}-2-pyridinyl)oxy]phenyl}methanesulfonamide dihydrochloride (or trihydrochloride)

TLC: Rf 0.16 (chloroform:methanol=10:1);
NMR (CD$_3$OD): δ 0.96, 1.30-1.45, 1.50-1.65, 1.90-2.05, 2.20-2.35, 2.98, 3.10-3.40, 3.50-3.70, 4.00, 4.20, 4.36, 7.09-7.16, 7.32, 7.95, 8.06, 8.08, 8.31.

Example 3(10)

N-(4-{4-[(4-{{[(4-fluorophenyl)amino]carbonyl}[4-(methylsulfanyl)phenyl]amino}-1-piperidinyl)methyl]phenoxy}phenyl)methanesulfonamide hydrochloride TLC: Rf 0.67 (dichloromethane:methanol=9:1);
NMR (CD$_3$OD): δ 1.60-1.79, 2.10-2.20, 2.51, 2.95, 3.08-3.20, 3.42-3.55, 4.22, 4.64, 6.95, 7.02, 7.03, 7.15-7.31, 7.39, 7.42.

Example 3(11)

N-(4-{4-[(4-{{[(4-fluorophenyl)amino]carbonyl}[3-(methylsulfanyl)phenyl]amino}-1-piperidinyl)methyl]phenoxy}phenyl)methanesulfonamide hydrochloride TLC: Rf 0.67 (dichloromethane:methanol=9:1);
NMR (CD$_3$OD): δ 1.62-1.80, 2.12-2.20, 2.51, 2.95, 3.04-3.22, 3.42-3.57, 4.22, 4.64, 6.89-7.10, 7.17-7.32, 7.34-7.49.

Example 3(12)

N-butyl-2,4-difluoro-N-[1-(4-{4-[(methylsulfonyl)amino]phenoxy}benzyl)-4-piperidinyl]benzamide hydrochloride TLC: Rf 0.41 (chloroform:methanol=10:1);
NMR (d$_6$-DMSO): δ 0.70-0.90, 1.10-1.30, 1.40-1.60, 1.75-1.90, 2.30-2.55, 2.80-3.05, 2.96, 3.10-3.45, 4.00, 4.17, 7.00, 7.01-7.04, 7.12, 7.19-7.30, 7.42, 7.57, 9.35.

Example 3(13)

N-(4-{4-[(4-{{[(4-fluorophenyl)amino]carbonyl}[4-(methylsulfinyl)phenyl]amino}-1-piperidinyl)methyl]phenoxy}phenyl)methanesulfonamide hydrochloride TLC: Rf 0.47 (dichloromethane:methanol=9:1);
NMR (CD$_3$OD): δ 1.67-1.83, 2.14-2.23, 2.84, 2.95, 3.10-3.21, 3.46-3.55, 4.23, 4.67, 6.96, 7.00, 7.02, 7.23, 7.28, 7.43, 7.54, 7.84.

Example 3(14)

N-(4-{4-[(4-{{[(4-fluorophenyl)amino]carbonyl}[3-(methylsulfinyl)phenyl]amino}-1-piperidinyl)methyl]phenoxy}phenyl)methanesulfonamide hydrochloride TLC: Rf 0.47 (dichloromethane:methanol=9:1);
NMR (CD$_3$OD): δ 1.62-1.80, 2.14-2.25, 2.86, 2.95, 3.08-3.21, 3.47-3.55, 4.23, 4.66, 6.96, 7.01, 7.02, 7.20-7.30, 7.42, 7.51, 7.66, 7.70-7.80.

Example 3(15)

N-(4-{4-[(4-{{[(4-fluorophenyl)amino]carbonyl}[4-(methylsulfonyl)phenyl]amino}-1-piperidinyl)methyl]phenoxy}phenyl)methanesulfonamide hydrochloride TLC: Rf 0.54 (dichloromethane:methanol=9:1);
NMR (CD$_3$OD): δ 1.70-1.88, 2.14-2.23, 2.95, 3.10-3.20, 3.16, 3.46-3.55, 4.23, 4.64, 6.96, 7.01, 7.02, 7.24, 7.28, 7.43, 7.57, 8.08.

Example 3(16)

N-(4-{4-[(4-{{[(4-fluorophenyl)amino]carbonyl}[3-(methylsulfonyl)phenyl]amino}-1-piperidinyl)methyl]phenoxy}phenyl)methanesulfonamide hydrochloride TLC: Rf 0.54 (dichloromethane:methanol=9:1);
NMR (CD$_3$OD): δ 1.64-1.80, 2.17-2.28, 2.95, 3.10-3.21, 3.19, 3.45-3.55, 4.23, 4.67, 6.96, 7.01, 7.02, 7.24, 7.28, 7.42, 7.66, 7.78, 7.89, 8.05.

Example 3(17)

N-[4-(4-{[4-(butyl{[(2,4-difluorophenyl)amino]carbonyl}amino)-1-piperidinyl]methyl}phenoxy)-3-methoxyphenyl]methanesulfonamide hydrochloride TLC: Rf 0.50 (chloroform:methanol=10:1);
NMR (CD$_3$OD): δ 0.97, 1.30-1.50, 1.60-1.70, 1.90-2.10, 2.15-2.30, 2.99, 3.05-3.20, 3.20-3.40, 3.50-3.60, 3.74, 4.15, 4.25, 6.85-6.95, 6.99, 7.03, 7.38, 7.43.

Example 3(18)

5-{[(butyl{1-[(6-{4-[(methylsulfonyl)amino]phenoxy}-3-pyridinyl)methyl]-4-piperidinyl}amino)carbonyl]amino}-2,4-difluorobenzamide hydrochloride (or dihydrochloride)

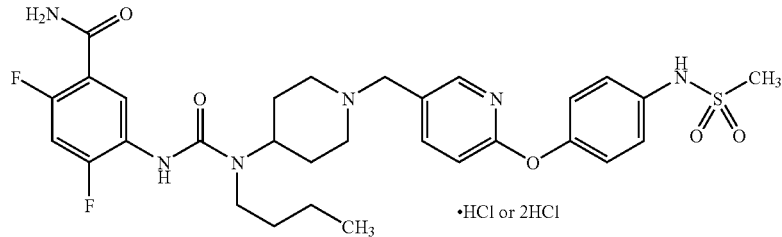

TLC: Rf 0.41 (chloroform:methanol 10:1);
NMR (CD$_3$OD): δ 0.98, 1.30-1.45, 1.55-1.70, 1.95-2.10, 2.15-2.35, 2.98, 3.05-3.20, 3.25-3.35, 3.50-3.65, 4.15, 4.34, 7.09-7.18, 7.33, 7.86, 8.03, 8.28.

Example 3(19)

5-{[(butyl{1-[(5-{4-[(methylsulfonyl)amino]phenoxy}-2-pyridinyl)methyl]-4-piperidinyl}amino)carbonyl]amino}-2,4-difluorobenzamide dihydrochloride TLC: Rf 0.36 (chloroform:methanol=10:1);
NMR (CD$_3$OD): δ 0.99, 1.30-1.50, 1.60-1.70, 1.90-2.10, 2.20-2.40, 2.96, 3.20-3.40, 3.60-3.70, 4.20, 4.45, 7.10, 7.15, 7.33, 7.44-7.50, 7.87, 8.44.

Example 3(20)

5-[({butyl[1-(4-{2-methoxy-4-[(methylsulfonyl)amino]phenoxy}benzyl)-4-piperidinyl]amino}carbonyl)amino]-2,4-difluorobenzamide hydrochloride TLC: Rf 0.34 (chloroform:methanol=10:1);
NMR (CD$_3$OD): δ 0.97, 1.30-1.50, 1.55-1.70, 1.90-2.10, 2.10-2.30, 2.99, 3.05-3.20, 3.20-3.40, 3.50-3.60, 3.74, 4.15, 4.25, 6.87, 6.92, 7.03, 7.14, 7.42, 7.85.

Example 3(21)

5-[({butyl[1-(4-{2-chloro-4-[(methylsulfonyl)amino]phenoxy}benzyl)-4-piperidinyl]amino}carbonyl)amino]-2,4-difluorobenzamide hydrochloride TLC: Rf 0.33 (chloroform:methanol=10:1);
NMR (CD$_3$OD): δ 0.97, 1.30-1.50, 1.55-1.70, 1.90-2.10, 2.10-2.30, 3.01, 3.10-3.20, 3.25-3.35, 3.50-3.60, 4.15, 4.28, 6.99, 7.13, 7.14, 7.24, 7.43, 7.50, 7.85.

Example 3(22)

4-(4-{[4-(butyl{[(2,4-difluorophenyl)amino]carbonyl}amino)-1-piperidinyl]methyl}phenoxy)-N-(2-hydroxyethyl)benzenesulfonamide hydrochloride TLC: Rf 0.69 (dichloromethane:methanol=10:1);
NMR (CD$_3$OD): δ 0.98, 1.36-1.43, 1.59-1.70, 1.98-2.03, 2.18-2.30, 2.96, 3.09-3.30, 3.54, 3.54-3.61, 4.16, 4.33, 6.90-7.03, 7.16, 7.20, 7.37, 7.59, 7.86.

Example 3(23)

4-(4-{[4-(butyl{[(2,4-difluorophenyl)amino]carbonyl}amino)-1-piperidinyl]methyl}phenoxy)-N-[2-(dimethylamino)ethyl]benzenesulfonamide dihydrochloride TLC: Rf 0.56 (dichloromethane:methanol=2:1);
NMR (CD$_3$OD): δ 0.98, 1.33-1.46, 1.59-1.70, 1.96-2.00, 2.20-2.35, 2.93, 3.05-3.12, 3.17-3.30, 3.52-3.56, 4.18, 4.30, 6.89-7.03, 7.19, 7.37, 7.61, 7.90.

Example 3(24)

N-{4-[4-({4-[{[(2,4-difluorophenyl)amino]carbonyl}(phenyl)amino]-1-piperidinyl}methyl)phenoxy]phenyl}methanesulfonamide hydrochloride TLC: Rf 0.76 (ethyl acetate:methanol=10:1);
NMR (CD$_3$OD): δ 1.60-1.80, 2.10-2.30, 2.95, 3.05-3.20, 3.40-3.55, 4.21, 4.65, 6.85-6.96, 6.99-7.04, 7.28, 7.35-7.40, 7.41, 7.51-7.58.

Example 3(25)

4-(4-{[4-(butyl{[(2,4-difluorophenyl)amino]carbonyl}amino)-1-piperidinyl]methyl}phenoxy)-N-methylbenzenesulfonamide hydrochloride TLC: Rf 0.63 (ethyl acetate:methanol=10:1);
NMR (CD$_3$OD): δ 0.98, 1.36-1.46, 1.59-1.70, 1.99-2.04, 2.17-2.30, 2.53, 3.07-3.17, 3.24-3.35, 3.57-3.61, 4.15, 4.33, 6.89-7.03, 7.16, 7.20, 7.36, 7.57, 7.83.

Example 3(26)

4-(4-{[4-(butyl{[(2,4-difluorophenyl)amino]carbonyl}amino)-1-piperidinyl]methyl}phenoxy)-N,N-dimethylbenzenesulfonamide hydrochloride TLC: Rf 0.67 (ethyl acetate:methanol=10:1);
NMR (CD$_3$OD): δ 0.98, 1.34-1.46, 1.60-1.70, 1.99-2.03, 2.19-2.30, 2.68, 3.09-3.17, 3.25-3.36, 3.57-3.61, 4.16, 4.33, 6.89-7.03, 7.18, 7.21, 7.36, 7.59, 7.78.

Example 3(27)

4-(4-{[4-(butyl{[(2,4-difluorophenyl)amino]carbonyl}amino)-1-piperidinyl]methyl}phenoxy)-N-(2-methoxyethyl)benzenesulfonamide hydrochloride TLC: Rf 0.60 (ethyl acetate:methanol=10:1);
NMR (CD$_3$OD): δ 0.98, 1.34-1.46, 1.60-1.70, 1.99-2.03, 2.19-2.30, 3.03, 3.09-3.17, 3.26, 3.26-3.30, 3.36, 3.56-3.61, 4.16, 4.33, 6.89-7.03, 7.14, 7.19, 7.37, 7.57, 7.85.

Example 3(28)

4-(4-{[4-(butyl{[(2,4-difluorophenyl)amino]carbonyl}amino)-1-piperidinyl]methyl}phenoxy)-N-tetrahydro-2H-pyran-4-ylbenzenesulfonamide hydrochloride TLC: Rf 0.57 (ethyl acetate:methanol=10:1);
NMR (CD$_3$OD): δ 0.98, 1.36-1.53, 1.63-1.68, 2.01-2.04, 2.21-2.25, 3.07-3.37, 3.57-3.61, 3.81-3.85, 4.14, 4.33, 4.80, 6.89-7.03, 7.14, 7.19, 7.36, 7.57, 7.87.

Example 3(29)

N-(4-{[5-({4-[{[(4-fluorophenyl)amino]carbonyl}(phenyl)amino]-1-piperidinyl}methyl)-2-pyridinyl]oxy}phenyl)methanesulfonamide hydrochloride (or dihydrochloride)

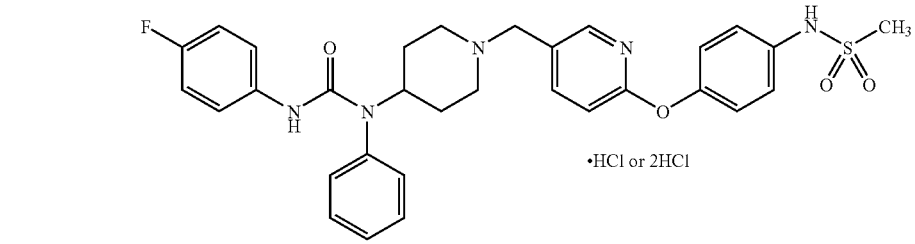

•HCl or 2HCl

TLC: Rf 0.53 (dichloromethane:methanol=9:1);
NMR (CD$_3$OD): δ 1.60-1.80, 2.12-2.23, 2.97, 3.11-3.24, 3.48-3.58, 4.27, 4.67, 6.95, 7.06, 7.11, 7.21, 7.28-7.35, 7.48-7.60, 7.90, 8.18.

Example 3(30)

N-[5-(4-{[4-(butyl{[(2,4-difluorophenyl)amino]carbonyl}amino)-1-piperidinyl]methyl}phenoxy)-2-pyridinyl]methanesulfonamide hydrochloride TLC: Rf 0.53 (dichloromethane:methanol=9:1);
NMR (CD$_3$OD): δ 0.97, 1.34-1.44, 1.58-1.68, 1.96-2.05, 2.15-2.31, 3.03-3.18, 3.28, 3.25-3.33, 3.52-3.60, 4.17, 4.30, 6.88-7.04, 7.12, 7.14, 7.37, 7.51-7.60, 8.10.

Example 3(31)

5-({[[butyl(1-{4-[4-(4-morpholinylsulfonyl)phenoxy]benzyl}-4-piperidinyl)amino]carbonyl}amino)-2,4-difluorobenzamide hydrochloride TLC: Rf 0.48 (chloroform:methanol=10:1);
NMR (CD$_3$OD): δ 0.98, 1.30-1.50, 1.60-1.70, 1.90-2.10, 2.20-2.35, 2.96, 3.00-3.20, 3.20-3.40, 3.50-3.60, 3.71, 4.10, 4.33, 7.11-7.24, 7.59, 7.78, 7.87.

Example 3(32)

5-[({butyl[1-(4-{4-[(tetrahydro-2H-pyran-4-ylamino)sulfonyl]phenoxy}benzyl)-4-piperidinyl]amino}carbonyl)amino]-2,4-difluorobenzamide hydrochloride TLC: Rf 0.40 (chloroform:methanol=10:1);
NMR (CD$_3$OD): δ 0.98, 1.30-1.50, 1.60-1.70, 1.90-2.10, 2.20-2.30, 3.10-3.20, 3.20-3.40, 3.50-3.70, 3.80-3.90, 4.15, 4.33, 7.11-7.21, 7.60, 7.87, 7.88.

Example 3(33)

5-[({butyl[1-(4-{2,6-dimethyl-4-[(methylsulfonyl)amino]phenoxy}benzyl)-4-piperidinyl]amino}carbonyl)amino]-2,4-difluorobenzamide hydrochloride TLC: Rf 0.34 (chloroform:methanol=10:1);
NMR (CD$_3$OD): δ 0.97, 1.30-1.50, 1.60-1.70, 1.90-2.10, 2.08, 2.20-2.30, 2.99, 3.00-3.20, 3.20-3.40, 3.50-3.60, 4.15, 4.26, 6.86, 7.04, 7.14, 7.45, 7.85.

Example 3(34)

5-[({butyl[1-(4-{4-[methyl(methylsulfonyl)amino]phenoxy}benzyl)-4-piperidinyl]amino}carbonyl)amino]-2,4-difluorobenzamide hydrochloride TLC: Rf 0.40 (chloroform:methanol=10:1);
NMR (CD$_3$OD): δ 0.98, 1.30-1.50, 1.60-1.70, 1.90-2.10, 2.15-2.30, 2.99, 3.00-3.20, 3.20-3.40, 3.30, 3.50-3.60, 4.15, 4.30, 7.05-7.18, 7.45, 7.52, 7.86.

Example 3(35)

5-[({butyl[1-(4-{4-[(methylsulfonyl)amino]benzyl}benzyl)-4-piperidinyl]amino}carbonyl)amino]-2,4-difluorobenzamide hydrochloride TLC: Rf 0.33 (chloroform:methanol=10:1);
NMR (CD$_3$OD): δ 0.97, 1.30-1.50, 1.60-1.70, 1.90-2.10, 2.15-2.30, 2.91, 3.00-3.20, 3.20-3.40, 3.50-3.60, 3.98, 4.15, 4.27, 7.10-7.20, 7.34, 7.44, 7.85.

Example 3(36)

5-{[(butyl{1-[(3,5-dimethyl-1-{4-[(methylsulfonyl)amino]phenyl}-1H-pyrazol-4-yl)methyl]-4-piperidinyl}amino)carbonyl]amino}-2,4-difluorobenzamide dihydrochloride TLC: Rf 0.20 (dichloromethane:methanol=9:1);
NMR (CD$_3$OD): δ 0.98, 1.34-1.47, 1.60-1.72, 1.98-2.10, 2.27-2.50, 2.39, 2.43, 3.04, 3.12-3.40, 3.65-3.75, 4.24, 4.29, 7.15, 7.43, 7.49, 7.87.

Example 3(37)

5-({[(1-{4-[4-(aminosulfonyl)phenoxy]benzyl}-4-piperidinyl)(butyl)amino]carbonyl}amino)-2,4-difluorobenzamide hydrochloride TLC: Rf 0.33 (dichloromethane:methanol=9:1);
NMR (CD$_3$OD): δ 0.98, 1.35-1.47, 1.58-1.70, 1.97-2.08, 2.18-2.32, 3.08-3.20, 3.23-3.35, 3.52-3.63, 4.16, 4.33, 7.10-7.24, 7.58, 7.64, 7.90.

Example 3(38)

5-[({butyl[1-(4-{4-[(methylamino)sulfonyl]phenoxy}benzyl)-4-piperidinyl]amino}carbonyl)amino]-2,4-difluorobenzamide hydrochloride

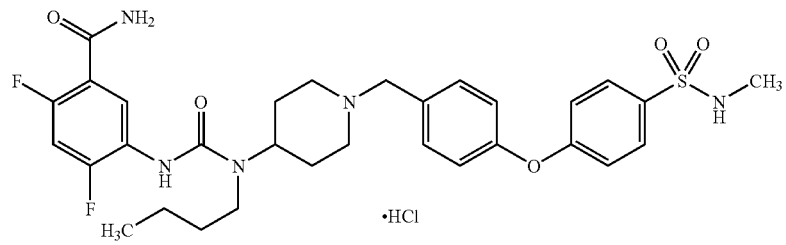

TLC: Rf 0.47 (dichloromethane:methanol=9:1);
NMR (CD$_3$OD): δ 0.98, 1.32-1.47, 1.60-1.71, 1.98-2.10, 2.20-2.36, 2.53, 3.08-3.20, 3.26-3.35, 3.52-3.64, 4.18, 4.33, 7.14, 7.16, 7.19, 7.60, 7.83, 7.86.

Example 3(39)

5-[({butyl[1-(4-{4-[(dimethylamino)sulfonyl]phenoxy}benzyl)-4-piperidinyl]amino}carbonyl)amino]-2,4-difluorobenzamide hydrochloride TLC: Rf 0.55 (dichloromethane:methanol=9:1);
NMR (CD$_3$OD): δ 0.98, 1.32-1.49, 1.59-1.72, 1.97-2.09, 2.19-2.38, 2.68, 3.08-3.21, 3.23-3.35, 3.58-3.64, 4.16, 4.34, 7.14, 7.19, 7.21, 7.60, 7.79, 7.86.

Example 3(40)

N-[4-(4-{[4-(butyl{[(2,4-difluorophenyl)amino]carbonyl}amino)-1-piperidinyl]methyl}phenoxy)-3-methylphenyl]methanesulfonamide hydrochloride TLC: Rf 0.39 (chloroform:methanol=10:1);
NMR (CD$_3$OD): δ 0.97, 1.30-1.50, 1.55-1.70, 1.90-2.10, 2.10-2.30, 2.16, 2.96, 3.00-3.20, 3.20-3.40, 3.50-3.60, 4.15, 4.27, 6.91-6.99, 7.13, 7.20, 7.36, 7.46.

Example 3(41)

5-[({butyl[1-(4-{2-methyl-4-[(methylsulfonyl)amino]phenoxy}benzyl)-4-piperidinyl]amino}carbonyl)amino]-2,4-difluorobenzamide hydrochloride White amorphous powder;
TLC: Rf 0.28 (chloroform:methanol=10:1);
NMR (CD$_3$OD): δ 0.98, 1.30-1.50, 1.55-1.70, 1.90-2.10, 2.10-2.30, 2.16, 2.96, 3.00-3.20, 3.20-3.40, 3.50-3.60, 4.10, 4.26, 6.91-6.97, 7.11-7.20, 7.46, 7.86.

Example 3(42)

4-[4-({4-[({[5-(aminocarbonyl)-2,4-difluorophenyl]amino}carbonyl)(butyl)amino]-1-piperidinyl}methyl)phenoxy]benzoic acid hydrochloride TLC: Rf 0.49 (dichloromethane:methanol=5:1);
NMR (CD$_3$OD): δ 0.98, 1.35-1.45, 1.60-1.70, 1.98-2.03, 2.20-2.30, 3.10-3.34, 3.56-3.60, 4.16, 4.33, 7.07, 7.14, 7.18, 7.57, 7.86, 8.04.

Example 3(43)

5-{[(butyl{1-[(6-{2-chloro-4-[(methylsulfonyl)amino]phenoxy}-3-pyridinyl)methyl]-4-piperidinyl}amino)carbonyl]amino}-2,4-difluorobenzamide hydrochloride (or dihydrochloride)

TLC: Rf 0.33 (chloroform:methanol=10:1);
NMR (CD$_3$OD): δ 0.97, 1.30-1.50, 1.55-1.70, 1.90-2.10, 2.20-2.40, 3.02, 3.10-3.25, 3.25-3.40, 3.50-3.60, 4.20, 4.35, 7.10-7.26, 7.43, 7.86, 8.09, 8.26.

Example 3(44)

5-{[(butyl{1-[(6-{2-methoxy-4-[(methylsulfonyl)amino]phenoxy}-3-pyridinyl)methyl]-4-piperidinyl}amino)carbonyl]amino}-2,4-difluorobenzamide hydrochloride (or dihydrochloride)

TLC: Rf 0.49 (dichloromethane:methanol=9:1);
NMR (CD$_3$OD): δ 0.97, 1.33-1.47, 1.58-1.71, 1.97-2.08, 2.20-2.38, 3.01, 3.07-3.21, 3.25-3.35, 3.55-3.65, 3.72, 4.18, 4.35, 6.90, 7.04-7.19, 7.86, 8.08, 8.29.

Example 3(45)

5-({[butyl(1-{4-[4-(methylsulfonyl)phenoxy]benzyl}-4-piperidinyl)amino]carbonyl}amino)-2,4-difluorobenzamide hydrochloride

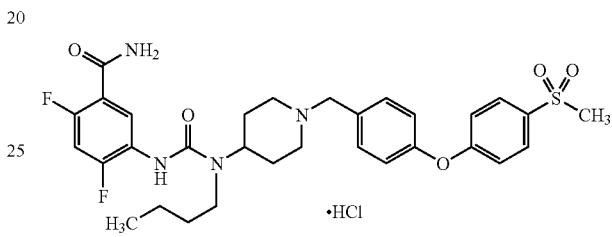

TLC: Rf 0.50 (dichloromethane:methanol=9:1);
NMR (CD$_3$OD): δ 0.98, 1.35-1.48, 1.59-1.70, 1.98-2.08, 2.19-2.34, 3.12, 3.08-3.21, 3.25-3.35, 3.55-3.64, 4.16, 4.34, 7.14, 7.21, 7.22, 7.61, 7.86, 7.95.

Example 3(46)

4-[4-({4-[{[(4-fluorophenyl)amino]carbonyl}(phenyl)amino]-1-piperidinyl}methyl)phenoxy]benzoic acid hydrochloride TLC: Rf 0.49 (dichloromethane:methanol=9:1);
NMR (CD$_3$OD): δ 1.67-1.80, 2.12-2.22, 3.12-3.24, 3.48-3.55, 4.26, 4.68, 6.95, 7.05, 7.14, 7.22, 7.33, 7.47-7.60, 8.03.

Example 3(47)

4-[4-({4-[({[5-(aminocarbonyl)-2,4-difluorophenyl]amino}carbonyl)(butyl)amino]-1-piperidinyl}methyl)phenoxy]-3-methoxybenzoic acid hydrochloride TLC: Rf 0.66 (chloroform:methanol=3:1);
NMR (CD$_3$OD): δ 0.98, 1.30-1.50, 1.60-1.70, 1.90-2.10, 2.10-2.35, 3.05-3.20, 3.25-3.35, 3.50-3.60, 3.82, 4.10, 4.28, 6.98, 7.09, 7.15, 7.47, 7.77, 7.75, 7.86.

Example 3(48)

4-[4-({4-[({[5-(aminocarbonyl)-2,4-difluorophenyl]amino}carbonyl)(butyl)amino]-1-piperidinyl}methyl)phenoxy]-3-chlorobenzoic acid hydrochloride TLC: Rf 0.65 (chloroform:methanol=3:1);
NMR (CD$_3$OD): δ 0.98, 1.30-1.50, 1.60-1.70, 1.90-2.10, 2.20-2.35, 3.05-3.20, 3.25-3.35, 3.50-3.60, 4.10, 4.33, 7.10-7.17, 7.57, 7.86, 7.95, 8.14.

Example 3(49)

4-[4-({4-[({[5-(aminocarbonyl)-2,4-difluorophenyl]amino}carbonyl)(butyl)amino]-1-piperidinyl}methyl)phenoxy]-3-nitrobenzoic acid hydrochloride TLC: Rf 0.51 (chloroform:methanol=3:1);
NMR (CD$_3$OD): δ 0.97, 1.30-1.50, 1.60-1.70, 1.90-2.10, 2.20-2.35, 3.00-3.15, 3.20-3.35, 3.50-3.60, 4.15, 4.29, 7.10-7.20, 7.58, 7.86, 8.20, 8.56.

Example 3(50)

5-[({butyl[1-(4-{3-methoxy-4-[(methylsulfonyl)amino]phenoxy}benzyl)-4-piperidinyl]amino}carbonyl)amino]-2,4-difluorobenzamide hydrochloride TLC: Rf 0.42 (dichloromethane:methanol=9:1);
NMR (CD$_3$OD): δ 0.98, 1.32-1.47, 1.58-1.70, 1.97-2.08, 2.17-2.31, 2.91, 3.06-3.20, 3.24-3.35, 3.51-3.63, 3.86, 4.13, 4.29, 6.57, 6.81, 7.10, 7.14, 7.36, 7.51, 7.86.

Example 3(51)

5-[({butyl[1-(4-{3-chloro-4-[(methylsulfonyl)amino]phenoxy}benzyl)-4-piperidinyl]amino}carbonyl)amino]-2,4-difluorobenzamide hydrochloride TLC: Rf 0.44 (dichloromethane:methanol=9:1);
NMR (CD$_3$OD): δ 0.98, 1.32-1.48, 1.60-1.72, 1.98-2.08, 2.12-2.31, 3.00, 3.08-3.20, 3.24-3.35, 3.52-3.62, 4.15, 4.31, 7.00, 7.10-7.20, 7.51-7.59, 7.86.

Example 3(52)

5-({[butyl(1-{[6-(4-methoxyphenoxy)-3-pyridinyl]methyl}-4-piperidinyl)amino]carbonyl}amino)-2,4-difluorobenzamide hydrochloride (or dihydrochloride)

TLC: Rf 0.39 (chloroform:methanol=10:1);
NMR (CD$_3$OD): δ 0.97, 1.30-1.50, 1.60-1.70, 1.90-2.10, 2.20-2.35, 3.05-3.20, 3.20-3.35, 3.50-3.65, 3.81, 4.20, 4.34, 6.97-7.20, 7.86, 8.05, 8.31.

Example 3(53)

4-{[5-({4-[({[5-(aminocarbonyl)-2,4-difluorophenyl]amino}carbonyl)(butyl)amino]-1-piperidinyl}methyl)-2-pyridinyl]oxy}benzoic acid hydrochloride (or dihydrochloride)

TLC: Rf 0.63 (chloroform:methanol=3:1);
NMR (CD$_3$OD): δ 0.97, 1.30-1.45, 1.55-1.70, 1.85-2.00, 2.05-2.20, 2.65-2.85, 3.20-3.40, 4.05, 4.10, 7.09-7.21, 7.89, 7.97, 8.07, 8.23.

Example 3(54)

N-(4-{4-[(4-{phenyl[(tetrahydro-2H-pyran-4-yl)amino]carbonyl]amino}-1-piperidinyl)methyl]phenoxy}phenyl)methanesulfonamide hydrochloride TLC: Rf 0.46 (dichloromethane:methanol=9:1);
NMR (CD$_3$OD): δ 1.24-1.40, 1.55-1.75, 2.05-2.15, 2.95, 3.04-3.18, 3.34-3.50, 3.68-3.84, 4.21, 4.60, 6.98-7.04, 7.22, 7.28, 7.41, 7.45-7.56.

Example 3(55)

5-{[(butyl{1-[(5-{4-[(methylsulfonyl)amino]phenoxy}-2-pyrazinyl)methyl]-4-piperidinyl}amino)carbonyl]amino}-2,4-difluorobenzamide dihydrochloride TLC: Rf 0.40 (dichloromethane:methanol=9:1);
NMR (CD$_3$OD): δ 0.99, 1.34-1.48, 1.59-1.72, 1.98-2.08, 2.21-2.38, 2.97, 3.17-3.38, 3.62-3.71, 4.18, 4.46, 7.14, 7.18, 7.33, 7.67, 8.24, 8.54.

Example 3(56)

5-[4-({4-[({[5-(aminocarbonyl)-2,4-difluorophenyl]amino}carbonyl)(butyl)amino]-1-piperidinyl}methyl)phenoxy]-2-[(methylsulfonyl)amino]benzoic acid hydrochloride TLC: Rf 0.48 (dichloromethane:methanol=5:1);
NMR (CD$_3$OD): δ 0.96, 1.28-1.47, 1.59-1.71, 1.95-2.06, 2.18-2.37, 3.02, 3.00-3.20, 3.24-3.35, 3.50-3.61, 4.15, 4.30, 7.08, 7.14, 7.25, 7.51, 7.67-7.72, 7.86.

Example 3(57)

2-[4-({4-[({[5-(aminocarbonyl)-2,4-difluorophenyl]amino}carbonyl)(butyl)amino]-1-piperidinyl}methyl)phenoxy]-5-[(methylsulfonyl)amino]benzoic acid hydrochloride TLC: Rf 0.35 (dichloromethane:methanol=5:1);
NMR (CD$_3$OD): δ 0.98, 1.31-1.48, 1.54-1.71, 1.94-2.04, 2.12-2.36, 3.00, 3.00-3.18, 3.20-3.35, 3.51-3.61, 4.15, 4.27, 6.98, 7.08, 7.14, 7.41-7.52, 7.82, 7.84.

Example 3(58)

N-[4-(4-{[4-(butyl{[(3,4-dicyanophenyl)amino]carbonyl}amino)-1-piperidinyl]methyl}phenoxy)phenyl]methanesulfonamide hydrochloride TLC: Rf 0.41 (dichloromethane:methanol=9:1);
NMR (CD$_3$OD): δ 0.96, 1.31-1.42, 1.52-1.64, 1.98-2.07, 2.21-2.39, 2.95, 3.04-3.21, 3.28-3.35, 3.52-3.61, 4.19, 4.30, 7.03, 7.06, 7.29, 7.52, 7.79-7.89, 8.11.

Example 3(59)

N-[4-(4-{[4-(butyl{[(4-cyano-2,5-difluorophenyl)amino]carbonyl}amino)-1-piperidinyl]methyl}phenoxy)phenyl]methanesulfonamide hydrochloride TLC: Rf 0.50 (dichloromethane:methanol=9:1);
NMR (CD$_3$OD): δ 0.97, 1.35-1.46, 1.55-1.68, 1.95-2.06, 2.19-2.37, 2.95, 3.08-3.21, 3.24-3.38, 3.52-3.61, 4.18, 4.29, 7.03, 7.06, 7.29, 7.50, 7.60, 7.87.

Example 3(60)

5-({[butyl(1-{[6-(4-cyanophenoxy)-3-pyridinyl]methyl}-4-piperidinyl)amino]carbonyl}amino)-2,4-difluorobenzamide hydrochloride (or dihydrochloride)

TLC: Rf 0.54 (dichloromethane:methanol=10:1);
NMR (CD$_3$OD): δ 0.98, 1.36-1.43, 1.59-1.67, 2.00-2.04, 2.21-2.32, 2.99-3.18, 3.26-3.30, 3.56-3.63, 4.14, 4.36, 7.14, 7.21, 7.33, 7.80, 7.86, 8.06, 8.29.

Example 3(61)

3-({[[1-(4-{4-[(methylsulfonyl)amino]phenoxy}benzyl)-4-piperidinyl](phenyl)amino]carbonyl}amino)benzamide hydrochloride TLC: Rf 0.33 (dichloromethane:methanol=9:1);
NMR (CD$_3$OD): δ 1.63-1.80, 2.14-2.23, 2.95, 3.10-3.22, 3.47-3.55, 4.23, 4.69, 7.01, 7.03, 7.25-7.37, 7.40-7.60, 7.72.

Example 3(62)

4-[({butyl[1-(4-{4-[(methylsulfonyl)amino]phenoxy}benzyl)-4-piperidinyl]amino}carbonyl)amino]benzamide hydrochloride TLC: Rf 0.33 (chloroform:methanol=7:1);
NMR (CD$_3$OD): δ 0.97, 1.30-1.50, 1.50-1.70, 1.95-2.10, 2.10-2.30, 2.95, 3.00-3.20, 3.20-3.40, 3.50-3.60, 4.20, 4.30, 7.02-7.08, 7.29, 7.47-7.52, 7.80.

Example 3(63)

N-{4-[4-({4-[butyl({[2,4-difluoro-5-(4-morpholinylcarbonyl)phenyl]amino}carbonyl)amino]-1-piperidinyl}methyl)phenoxy]phenyl}methane sulfonamide hydrochloride TLC: Rf 0.38 (chloroform:methanol=10:1);
NMR (CD$_3$OD): δ 0.98, 1.30-1.50, 1.60-1.70, 1.95-2.05, 2.10-2.30, 2.95, 3.00-3.20, 3.20-3.50, 3.50-3.70, 3.70-3.80, 4.10, 4.29, 7.02-7.08, 7.15, 7.29, 7.46, 7.49.

Example 3(64)

5-[({butyl[1-(4-{4-[(methylsulfonyl)amino]phenoxy}benzyl)-4-piperidinyl]amino}carbonyl)amino]-2,4-difluoro-N-(2-methoxyethyl)benzamide hydrochloride TLC: Rf 0.44 (chloroform:methanol=10:1);
NMR (CD$_3$OD): δ 0.98, 1.30-1.50, 1.60-1.75, 1.90-2.10, 2.15-2.35, 2.95, 3.00-3.20, 3.20-3.40, 3.50-3.60, 3.55, 4.13, 4.28, 7.02-7.08, 7.13, 7.29, 7.49, 7.78.

Example 3(65)

5-[({butyl[1-(4-{4-[(methylsulfonyl)amino]phenoxy}benzyl)-4-piperidinyl]amino}carbonyl)amino]-2,4-difluoro-N,N-dimethylbenzamide hydrochloride TLC: Rf 0.46 (chloroform:methanol=10:1);
NMR (CD$_3$OD): δ 0.98, 1.30-1.50, 1.60-1.80, 1.90-2.10, 2.20-2.30, 2.95, 2.97, 3.05-3.20, 3.10, 3.25-3.35, 3.50-3.60, 4.15, 4.29, 7.02-7.08, 7.14, 7.29, 7.43, 7.50.

Example 3(66)

5-[({butyl[1-(4-{4-[(methylsulfonyl)amino]phenoxy}benzyl)-4-piperidinyl]amino}carbonyl)amino]-2,4-difluoro-N-(2-hydroxyethyl)benzamide hydrochloride TLC: Rf 0.38 (chloroform:methanol 10:1);
NMR (CD$_3$OD): δ 0.98, 1.30-1.50, 1.60-1.70, 1.90-2.10, 2.10-2.30, 2.95, 3.05-3.20, 3.20-3.40, 3.50, 3.50-3.60, 3.67, 4.15, 4.27, 7.02-7.07, 7.13, 7.29, 7.50, 7.81.

Example 3(67)

N-{4-[(5-{[4-(butyl{[(1-methyl-1H-pyrazol-4-yl)amino]carbonyl}amino)-1-piperidinyl]methyl}-2-pyridinyl)oxy]-3-chlorophenyl}methanesulfonamide dihydrochloride (or trihydrochloride)

TLC: Rf 0.57 (chloroform:methanol=7:1);
NMR (CD$_3$OD): δ 0.96, 1.30-1.45, 1.50-1.65, 1.90-2.10, 2.20-2.40, 3.02, 3.10-3.50, 3.50-3.65, 4.08, 4.25, 4.37, 7.16, 7.24-7.26, 7.43, 8.12, 8.16, 8.23, 8.28.

Example 3(68)

N-{4-[(5-{[4-(butyl{[(1-methyl-1H-pyrazol-4-yl)amino]carbonyl}amino)-1-piperidinyl]methyl}-2-pyridinyl)oxy]-3,5-dimethylphenyl}methanesulfonamide dihydrochloride (or trihydrochloride)

TLC: Rf 0.56 (chloroform:methanol=7:1);
NMR (CD$_3$OD): δ 0.96, 1.30-1.50, 1.50-1.65, 1.90-2.05, 2.08, 2.20-2.40, 2.98, 3.10-3.40, 3.55-3.65, 4.06, 4.25, 4.37, 7.05, 7.08, 8.13, 8.16, 8.20, 8.33.

Example 3(69)

5-{[(butyl{1-[(6-{2-methyl-4-[(methylsulfonyl)amino]phenoxy}-3-pyridinyl)methyl]-4-piperidinyl}amino)carbonyl]amino}-2,4-difluorobenzamide hydrochloride (or dihydrochloride)

TLC: Rf 0.43 (dichloromethane:methanol=9:1);
NMR (CD$_3$OD): δ 0.97, 1.32-1.45, 1.58-1.70, 1.95-2.07, 2.14, 2.20-2.40, 2.98, 3.08-3.21, 3.24-3.37, 3.55-3.64, 4.20, 4.36, 7.02-7.25, 7.86, 8.14, 8.34.

Example 3(70)

5-{[(butyl{1-[(6-{2,6-dimethyl-4-[(methylsulfonyl)amino]phenoxy}-3-pyridinyl)methyl]-4-piperidinyl}amino)carbonyl]amino}-2,4-difluorobenzamide hydrochloride (or dihydrochloride)

TLC: Rf 0.44 (dichloromethane:methanol=9:1);
NMR (CD$_3$OD): δ 0.97, 1.32-1.45, 1.58-1.70, 1.95-2.08, 2.08, 2.21-2.39, 2.98, 3.08-3.21, 3.24-3.35, 3.55-3.65, 4.20, 4.36, 7.05, 7.08, 7.14, 7.86, 8.14, 8.33.

Example 3(71)

5-[({2-butynyl[1-(4-{4-[(methylsulfonyl)amino]phenoxy}benzyl)-4-piperidinyl]amino}carbonyl)amino]-2,4-difluorobenzamide hydrochloride TLC: Rf 0.52 (dichloromethane:methanol=9:1);
NMR (CD$_3$OD): δ 1.82, 2.01-2.12, 2.12-2.31, 2.95, 3.08-3.19, 3.52-3.61, 4.10, 4.29, 4.32, 7.03, 7.06, 7.15, 7.29, 7.51, 7.96.

Example 3(72)

2,4-difluoro-5-({[[1-(4-{4-[(methylsulfonyl)amino]phenoxy}benzyl)-4-piperidinyl](propyl)amino]carbonyl}amino)benzamide hydrochloride TLC: Rf 0.51 (dichloromethane:methanol=9:1);
NMR (CD$_3$OD): δ 0.97, 1.62-1.75, 1.98-2.08, 2.18-2.30, 2.95, 3.02-3.18, 3.21-3.33, 3.52-3.60, 4.14, 4.28, 7.03, 7.06, 7.14, 7.29, 7.50, 7.85.

Example 3(73)

N-{4-[4-({4-[butyl({[2,4-difluoro-5-(hydroxymethyl)phenyl]amino}carbonyl)amino]-1-piperidinyl}methyl)phenoxy]phenyl}methanesulfonamide hydrochloride TLC: Rf 0.80 (chloroform:methanol=7:1);
NMR (CD$_3$OD): δ 0.98, 1.30-1.50, 1.60-1.75, 1.90-2.10, 2.20-2.35, 2.96, 3.05-3.20, 3.20-3.40, 3.50-3.65, 4.20, 4.29, 4.60, 6.97, 7.03, 7.06, 7.29, 7.46, 7.52.

Example 3(74)

2,4-difluoro-5-({[{1-[(6-{4-[(methylsulfonyl)amino]phenoxy}-3-pyridinyl)methyl]-4-piperidinyl}(pentyl)amino]carbonyl}amino)benzamide hydrochloride (or dihydrochloride)

TLC: Rf 0.52 (dichloromethane:methanol=9:1);
NMR (CD$_3$OD): δ 0.93, 1.28-1.45, 1.60-1.71, 1.97-2.08, 2.20-2.38, 2.98, 3.08-3.22, 3.25-3.35, 3.55-3.64, 4.18, 4.35, 7.09-7.20, 7.33, 7.86, 8.08, 8.31.

Example 3(75)

5-{[(butyl{1-[(6-{4-[(ethylsulfonyl)amino]phenoxy}-3-pyridinyl)methyl]-4-piperidinyl}amino)carbonyl]amino}-2,4-difluorobenzamide hydrochloride (or dihydrochloride)

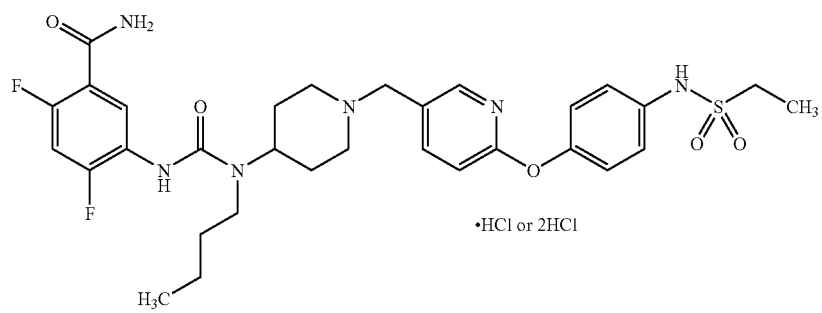

TLC: Rf 0.48 (dichloromethane:methanol=9:1);
NMR (CD$_3$OD): δ 0.97, 1.32, 1.28-1.45, 1.57-1.70, 1.95-2.08, 2.21-2.38, 3.11, 3.08-3.21, 3.25-3.35, 3.52-3.64, 4.18, 4.35, 7.07-7.17, 7.33, 7.86, 8.08, 8.31.

Example 3(76)

N-(4-{[5-({4-[{[(1-methyl-1H-pyrazol-4-yl)amino]carbonyl}(pentyl)amino]-1-piperidinyl}methyl)-2-pyridinyl]oxy}phenyl)methanesulfonamide dihydrochloride (or trihydrochloride)

TLC: Rf 0.50 (dichloromethane:methanol=9:1);
NMR (CD$_3$OD): δ 0.92, 1.28-1.42, 1.52-1.64, 1.92-2.04, 2.20-2.38, 2.98, 3.10-3.29, 3.52-3.64, 4.04, 4.24, 4.37, 7.11, 7.16, 7.34, 8.05, 8.12, 8.14, 8.34.

Example 3(77)

N-{4-[(5-{[4-(butyl{[(1-ethyl-1H-pyrazol-4-yl)amino]carbonyl}amino)-1-piperidinyl]methyl}-2-pyridinyl)oxy]phenyl}methanesulfonamide dihydrochloride (or trihydrochloride)

TLC: Rf 0.50 (dichloromethane:methanol=9:1);
NMR (CD$_3$OD): δ 0.97, 1.28-1.42, 1.52, 1.50-1.64, 1.90-2.02, 2.20-2.38, 2.98, 3.04-3.29, 3.51-3.64, 4.24, 4.30-4.44, 7.13, 7.16, 7.34, 8.05-8.16, 8.21, 8.34.

Example 3(78)

5-[({butyl[1-({6-[4-(methylsulfonyl)phenoxy]-3-pyridinyl}methyl)-4-piperidinyl]amino}carbonyl)amino]-2,4-difluorobenzamide hydrochloride (or dihydrochloride)

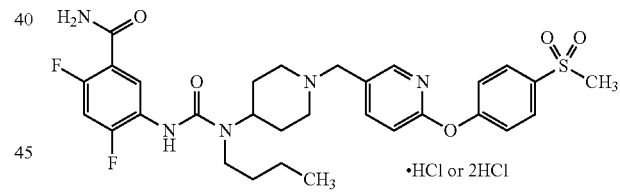

TLC: Rf 0.48 (chloroform:methanol=7:1);
NMR (CD$_3$OD): δ 0.98, 1.30-1.50, 1.55-1.70, 2.00-2.10, 2.20-2.40, 3.05-3.20, 3.15, 3.25-3.40, 3.50-3.70, 4.20, 4.36, 7.14, 7.22, 7.40, 7.86, 8.01, 8.07, 8.29.

Example 3(79)

2,4-difluoro-5-({[[1-({6-[4-(methylsulfonyl)phenoxy]-3-pyridinyl}methyl)-4-piperidinyl](pentyl)amino]carbonyl}amino)benzamide hydrochloride (or dihydrochloride)

TLC: Rf 0.44 (chloroform:methanol=7:1);
NMR (CD$_3$OD): δ 0.94, 1.30-1.45, 1.60-1.75, 2.00-2.10, 2.15-2.40, 3.00-3.20, 3.15, 3.20-3.40, 3.50-3.70, 4.15, 4.35, 7.14, 7.22, 7.39, 7.86, 8.01, 8.05, 8.29.

Example 3(80)

2,4-difluoro-5-({[{1-[(6-{2-methyl-4-[(methylsulfonyl)amino]phenoxy}-3-pyridinyl)methyl]-4-piperidinyl}(pentyl)amino]carbonyl}amino)benzamide hydrochloride (or dihydrochloride)

TLC: Rf 0.46 (chloroform:methanol=7:1);
NMR (CD$_3$OD): δ 0.93, 1.30-1.45, 1.60-1.75, 1.95-2.10, 2.13, 2.15-2.30, 2.98, 3.10-3.40, 3.55-3.65, 4.15, 4.34, 7.01-7.21, 7.86, 8.04, 8.26.

Example 3(81)

5-({[{1-[(6-{2,6-dimethyl-4-[(methylsulfonyl)amino]phenoxy}-3-pyridinyl)methyl]-4-piperidinyl}(pentyl)amino]carbonyl}amino)-2,4-difluorobenzamide hydrochloride (or dihydrochloride)

TLC: Rf 0.50 (chloroform:methanol=7:1);
NMR (CD$_3$OD): δ 0.93, 1.30-1.45, 1.60-1.70, 2.00-2.10, 2.06, 2.15-2.30, 2.99, 3.00-3.40, 3.50-3.70, 4.10, 4.32, 7.03, 7.08, 7.14, 7.86, 7.98, 8.20.

Example 3(82)

5-({[{1-[(6-(4-[(ethylsulfonyl)amino]phenoxy}-3-pyridinyl)methyl]-4-piperidinyl}(pentyl)amino]carbonyl)amino)-2,4-difluorobenzamide hydrochloride (or dihydrochloride)

TLC: Rf 0.46 (chloroform:methanol=7:1);
NMR (CD$_3$OD): δ 0.93, 1.30-1.45, 1.33, 1.60-1.70, 2.00-2.10, 2.20-2.40, 3.00-3.40, 3.11, 3.50-3.70, 4.15, 4.34, 7.08-7.17, 7.32, 7.86, 8.03, 8.28.

Example 3(83)

5-({[{1-[(6-{2-chloro-4-[(methylsulfonyl)amino]phenoxy}-3-pyridinyl)methyl]-4-piperidinyl}(pentyl)amino]carbonyl}amino)-2,4-difluorobenzamide hydrochloride (or dihydrochloride)

TLC: Rf 0.45 (chloroform:methanol=7:1);
NMR (CD$_3$OD): δ 0.93, 1.30-1.50, 1.60-1.75, 2.00-2.10, 2.15-2.25, 3.02, 3.05-3.35, 3.50-3.70, 4.10, 4.33, 7.14-7.28, 7.42, 7.86, 8.00, 8.20.

Example 3(84)

N-(4-{[5-({4-[{[(4-fluorophenyl)amino]carbonyl}(phenyl)amino]-1-piperidinyl}methyl)-2-pyridinyl]oxy}-3-methoxyphenyl)methanesulfonamide hydrochloride (or dihydrochloride)

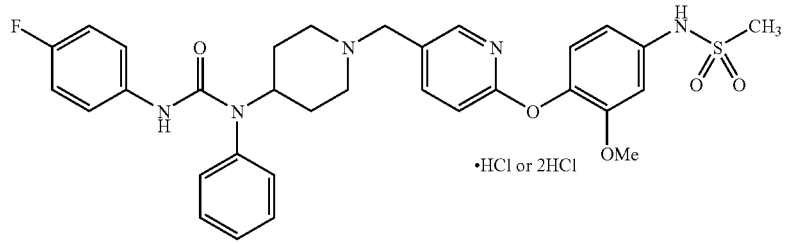

TLC: Rf 0.45 (dichloromethane:methanol=9:1);
NMR (CD$_3$OD): δ 1.64-1.82, 2.11-2.21, 3.00, 3.10-3.24, 3.48-3.57, 3.71, 4.31, 4.67, 6.87-7.00, 7.02-7.09, 7.12, 7.20, 7.32, 7.45-7.59, 8.03, 8.26.

Example 3(85)

N-(4-{[5-({4-[{[(2,4-difluorophenyl)amino]carbonyl}(phenyl)amino]-1-piperidinyl}methyl)-2-pyridinyl]oxy}-3-methoxyphenyl)methanesulfonamide hydrochloride (or dihydrochloride)

Amorphous powder;

TLC: Rf 0.45 (dichloromethane:methanol=9:1);
NMR (CD$_3$OD): δ 1.67-1.82, 2.11-2.24, 3.00, 3.12-3.24, 3.50-3.57, 3.71, 4.30, 4.67, 6.84-6.97, 7.01-7.08, 7.11, 7.35, 7.48-7.61, 8.02, 8.24.

Example 3(86)

5-{[(butyl{1-[(6-{2-methyl-4-[(methylsulfonyl)amino]phenoxy}-3-pyridinyl)methyl]-4-piperidinyl}amino)carbonyl]amino}-2-chloro-4-fluorobenzamide hydrochloride (or dihydrochloride)

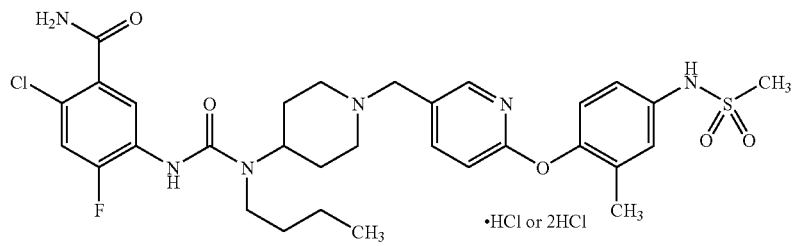

TLC: Rf 0.40 (chloroform:methanol=10:1);
NMR (CD$_3$OD): δ 0.97, 1.30-1.50, 1.55-1.70, 1.90-2.10, 2.12, 2.20-2.40, 2.97, 3.00-3.20, 3.25-3.35, 3.50-3.70, 4.20, 4.33, 7.00-7.21, 7.32, 7.66, 8.01, 8.24.

Example 3(87)

5-{[(butyl{1-[(6-{4-[(ethylsulfonyl)amino]phenoxy}-3-pyridinyl)methyl]-4-piperidinyl}amino)carbonyl]amino}-2-chloro-4-fluorobenzamide hydrochloride (or dihydrochloride)

TLC: Rf 0.40 (chloroform:methanol=10:1);
NMR (CD$_3$OD): δ 0.98, 1.33, 1.35-1.50, 1.60-1.70, 1.95-2.10, 2.20-2.40, 3.10, 3.10-3.20, 3.20-3.40, 3.50-3.65, 4.15, 4.33, 7.08-7.12, 7.30-7.34, 7.65, 7.99, 8.24.

Example 3(88)

5-{[(butyl{1-[(6-{4-[(ethylsulfonyl)amino]-2-methylphenoxy}-3-pyridinyl)methyl]-4-piperidinyl}amino)carbonyl]amino}-2,4-difluorobenzamide hydrochloride (or dihydrochloride)

TLC: Rf 0.62 (dichloromethane:methanol=9:1);
NMR (CD$_3$OD): δ 0.98, 1.33, 1.28-1.45, 1.59-1.70, 1.97-2.08, 2.12, 2.18-2.34, 3.11, 3.06-3.20, 3.25-3.35, 3.52-3.63, 4.12, 4.33, 7.00, 7.07, 7.13, 7.15, 7.20, 7.86, 8.01, 8.24.

Example 3(89)

5-{[(butyl{1-[(6-{2-methyl-4-[(methylsulfonyl)amino]phenoxy}-3-pyridinyl)methyl]-4-piperidinyl}amino)carbonyl]amino}-2,4-difluoro-N-methylbenzamide hydrochloride (or dihydrochloride)

TLC: Rf 0.53 (dichloromethane:methanol=9:1);
NMR (CD$_3$OD): δ 0.97, 1.30-1.47, 1.58-1.70, 1.95-2.07, 2.13, 2.20-2.37, 2.91, 2.98, 3.04-3.21, 3.22-3.35, 3.52-3.64, 4.18, 4.34, 7.01-7.24, 7.79, 8.06, 8.27.

Example 3(90)

5-{[(butyl{1-[(6-{4-[(ethylsulfonyl)amino]phenoxy}-3-pyridinyl)methyl]-4-piperidinyl}amino)carbonyl]amino}-2,4-difluoro-N-methylbenzamide hydrochloride (or dihydrochloride)

TLC: Rf 0.53 (dichloromethane:methanol=9:1);
NMR (CD$_3$OD): δ 0.98, 1.33, 1.30-1.47, 1.59-1.70, 1.98-2.05, 2.20-2.38, 2.91, 3.11, 3.07-3.21, 3.22-3.35, 3.52-3.64, 4.18, 4.35, 7.08-7.16, 7.32, 7.79, 8.06, 8.29.

Example 3(91)

5-{[(butyl{1-[(6-{2-chloro-4-[(methylsulfonyl)amino]phenoxy}-3-pyridinyl)methyl]-4-piperidinyl}amino)carbonyl]amino}-2,4-difluoro-N-methylbenzamide hydrochloride (or dihydrochloride)

TLC: Rf 0.53 (dichloromethane:methanol=9:1);
NMR (CD$_3$OD): δ 0.97, 1.32-1.45, 1.58-1.70, 1.97-2.05, 2.20-2.37, 2.91, 3.02, 3.04-3.21, 3.22-3.35, 3.51-3.62, 4.18, 4.34, 7.06-7.29, 7.42, 7.79, 8.06, 8.23.

Example 3(92)

5-{[(butyl{1-[(6-{2-methoxy-4-[(methylsulfonyl)amino]phenoxy}-3-pyridinyl)methyl]-4-piperidinyl}amino)carbonyl]amino}-2,4-difluoro-N-methylbenzamide hydrochloride (or dihydrochloride)

TLC: Rf 0.52 (dichloromethane:methanol=9:1);
NMR (CD$_3$OD): δ 0.97, 1.32-1.45, 1.58-1.70, 1.95-2.05, 2.19-2.37, 2.91, 3.00, 3.04-3.21, 3.22-3.35, 3.54-3.62, 3.72, 4.18, 4.34, 6.90, 7.04-7.17, 7.79, 8.06, 8.27.

Example 3(93)

2-(5-{[(butyl{1-[(6-{4-[(methylsulfonyl)amino]phenoxy}-3-pyridinyl)methyl]-4-piperidinyl}amino)carbonyl]amino}-2,4-difluorophenyl)acetamide hydrochloride (or dihydrochloride)

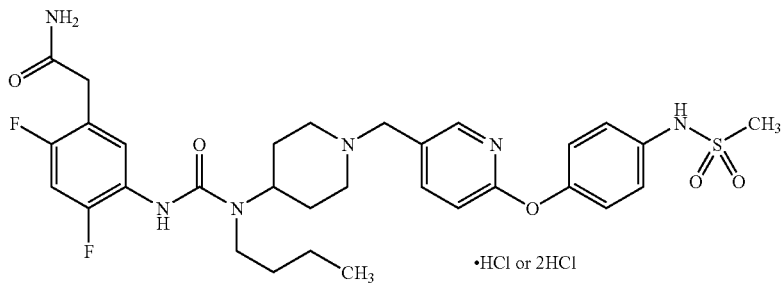

TLC: Rf 0.42 (chloroform:methanol=7:1);
NMR (CD₃OD): δ 0.97, 1.30-1.50, 1.50-1.70, 1.95-2.10, 2.15-2.30, 2.97, 3.05-3.20, 3.20-3.40, 3.50-3.60, 3.53, 4.10, 4.33, 7.00, 7.08-7.14, 7.30-7.34, 7.97, 8.24.

Example 3(94)

2-[2,4-difluoro-5-({[{1-[(6-{4-[(methylsulfonyl)amino]phenoxy}-3-pyridinyl)methyl]-4-piperidinyl}(pentyl)amino]carbonyl}amino)phenyl]acetamide hydrochloride (or dihydrochloride)

TLC: Rf 0.43 (chloroform:methanol=7:1);
NMR (CD₃OD): δ 0.93, 1.30-1.50, 1.55-1.75, 1.90-2.10, 2.15-2.35, 2.97, 3.10-3.20, 3.20-3.40, 3.50-3.60, 3.53, 4.15, 4.33, 7.00, 7.08-7.14, 7.30-7.34, 7.99, 8.25.

Example 3(95)

5-{[(butyl{1-[(6-{4-[(methylsulfonyl)amino]phenoxy}-3-pyridinyl)methyl]-4-piperidinyl}amino)carbonyl]amino}-2,4-difluoro-N-methylbenzamide hydrochloride (or dihydrochloride)

TLC: Rf 0.41 (chloroform:methanol=7:1);
NMR (CD₃OD): δ 0.98, 1.35-1.50, 1.65-1.80, 1.95-2.10, 2.20-2.35, 2.91, 2.97, 3.05-3.20, 3.20-3.40, 3.55-3.70, 4.10, 4.34, 7.08-7.16, 7.32, 7.80, 8.00, 8.24.

Example 3(96)

2,4-difluoro-N-methyl-5-({[{1-[(6-{4-[(methylsulfonyl)amino]phenoxy}-3-pyridinyl)methyl]-4-piperidinyl}(pentyl)amino]carbonyl}amino)benzamide hydrochloride (or dihydrochloride)

TLC: Rf 0.43 (chloroform:methanol=7:1);
NMR (CD₃OD): δ 0.93, 1.30-1.50, 1.60-1.75, 1.95-2.10, 2.20-2.40, 2.91, 2.97, 3.05-3.20, 3.20-3.40, 3.50-3.70, 4.15, 4.34, 7.08-7.16, 7.32, 7.79, 8.00, 8.24.

Example 3(97)

5-({[{1-[(6-{4-[(ethylsulfonyl)amino]phenoxy}-3-pyridinyl)methyl]-4-piperidinyl}(pentyl)amino]carbonyl}amino)-2,4-difluoro-N-methylbenzamide hydrochloride (or dihydrochloride)

TLC: Rf 0.45 (chloroform:methanol=7:1);
NMR (CD₃OD): δ 0.93, 1.33, 1.30-1.45, 1.60-1.70, 1.90-2.10, 2.15-2.30, 2.91, 3.05-3.20, 3.10, 3.20-3.40, 3.50-3.60, 4.10, 4.33, 7.07-7.16, 7.32, 7.79, 7.97, 8.24.

Example 3(98)

2,4-difluoro-N-methyl-5-({[{1-[(6-{2-methyl-4-[(methylsulfonyl)amino]phenoxy}-3-pyridinyl)methyl]-4-piperidinyl}(pentyl)amino]carbonyl}amino)benzamide hydrochloride (or dihydrochloride)

TLC: Rf 0.45 (chloroform:methanol=7:1);
NMR (CD₃OD): δ 0.93, 1.30-1.40, 1.60-1.70, 1.95-2.05, 2.13, 2.20-2.40, 2.91, 2.98, 3.05-3.20, 3.20-3.40, 3.55-3.65, 4.15, 4.34, 7.11-7.21, 7.79, 8.04, 8.26.

Example 3(99)

N-[4-(4-{[4-(butyl{[(1,5-dimethyl-1H-pyrazol-4-yl)amino]carbonyl}amino)-1-piperidinyl]methyl}phenoxy)phenyl]methanesulfonamide dihydrochloride TLC: Rf 0.84 (chloroform:methanol=4:1);
NMR (CD₃OD): δ 0.97, 1.30-1.50, 1.60-1.80, 1.90-2.10, 2.10-2.30, 2.27, 2.95, 3.00-3.20, 3.20-3.40, 3.50-3.60, 3.92, 4.20, 4.29, 7.02-7.08, 7.31, 7.51, 7.84.

Example 3(100)

4-(4-{[4-(butyl{[(2,4-difluorophenyl)amino]carbonyl}amino)-1-piperidinyl]methyl}phenoxy)-N-[2-(dimethylamino)ethyl]benzenesulfonamide dihydrochloride TLC: Rf 0.40 (dichloromethane:methanol=5:1);
NMR (CD₃OD): δ 0.98, 1.36-1.43, 1.60-1.70, 1.98-2.02, 2.20-2.35, 2.94, 3.10-3.34, 3.56-3.60, 4.21, 4.34, 6.90-7.01, 7.18-7.21, 7.36, 7.62, 7.89.

Example 3(101)

5-{[(butyl{1-[(6-{4-[(methylsulfonyl)amino]phenoxy}-1-oxide-3-pyridinyl)methyl]-4-piperidinyl}amino)carbonyl]amino}-2,4-difluorobenzamide hydrochloride TLC: Rf 0.54 (chloroform:methanol=4:1);

NMR (CD₃OD): δ 0.99, 1.30-1.50, 1.55-1.70, 1.95-2.15, 2.20-2.40, 3.01, 3.10-3.40, 3.55-3.70, 4.15, 4.39, 7.12-7.21, 7.25, 7.40, 7.81, 7.87, 8.70.

Example 3(102)

5-[({butyl[1-(4-{4-[(methylsulfonyl)amino] phenoxy}benzyl)-4-piperidinyl]amino}carbonyl) amino]-N-[2-(dimethylamino)ethyl]-2,4-difluorobenzamide dihydrochloride TLC: Rf 0.17 (chloroform:methanol=10:1);
NMR (CD₃OD): δ 0.98, 1.30-1.50, 1.60-1.80, 1.90-2.10, 2.20-2.40, 2.95, 2.98, 3.00-3.20, 3.20-3.40, 3.50-3.80, 4.20, 4.29, 7.02-7.08, 7.17, 7.29, 7.52, 7.91.

Example 3(103)

5-{[(benzyl {1-[(6-{4-[(methylsulfonyl)amino]phenoxy}-3-pyridinyl)methyl]-4-piperidinyl}amino) carbonyl]amino}-2,4-difluorobenzamide hydrochloride (or dihydrochloride)

TLC: Rf 0.51 (dichloromethane:methanol=9:1);
NMR (CD₃OD): δ 1.97-2.06, 2.07-2.22, 2.97, 3.04-3.18, 3.47-3.58, 4.30, 4.37, 4.66, 7.04-7.17, 7.21-7.45, 7.89, 8.00, 8.24.

Example 3(104)

methyl 4-[4-({4-[({[5-(aminocarbonyl)-2,4-difluorophenyl]amino}carbonyl)(butyl)amino]-1-piperidinyl}methyl)phenoxy]-3-methoxybenzoate hydrochloride TLC: Rf 0.58 (dichloromethane:methanol=9:1);

NMR (CD₃OD): δ 0.98, 1.32-1.44, 1.58-1.70, 1.95-2.04, 2.12-2.30, 3.08-3.18, 3.22-3.35, 3.51-3.61, 3.82, 3.91, 4.14, 4.28, 6.99, 7.09, 7.14, 7.47, 7.67, 7.73, 7.85.

Example 3(105)

2,4-difluoro-5-{[(hexyl{1-[(6-{4-[(methylsulfonyl) amino]phenoxy}-3-pyridinyl)methyl]-4-piperidinyl}amino)carbonyl]amino}benzamide hydrochloride (or dihydrochloride)

TLC: Rf 0.47 (chloroform:methanol=7:1);

NMR (CD₃OD): δ 0.91, 1.30-1.50, 1.60-1.70, 2.00-2.10, 2.20-2.35, 2.97, 3.00-3.20, 3.20-3.40, 3.50-3.70, 4.10, 4.33, 7.08-7.18, 7.32, 7.86, 7.98, 8.24.

Example 3(106)

methyl N-[4-(4-{[4-(butyl{[(2,4-difluorophenyl) amino]carbonyl}amino)piperidin-1-yl] methyl}phenoxy)phenyl]-N-(methylsulfonyl)glycinate hydrochloride TLC: Rf 0.46 (dichloromethane:methanol=9:1);
NMR (CD₃OD): δ 0.96, 1.27-1.44, 1.55-1.90, 2.10-2.20, 2.95-3.07, 3.08, 3.21-3.34, 3.53, 3.74, 4.05, 4.46, 6.85-7.04, 7.03-7.45, 7.47.

Example 3(107)

methyl N-{4-[4-({4-[({[5-(aminocarbonyl)-2,4-difluorophenyl]amino}carbonyl)(butyl)amino]piperidin-1-yl}methyl)phenoxy]phenyl}-N-(methylsulfonyl)glycinate hydrochloride TLC: Rf 0.52 (dichloromethane:methanol=9:1);
NMR (CD₃OD): δ 0.97, 1.32-1.42, 1.58-1.68, 1.70-1.97, 2.12-2.28, 2.99-3.12, 3.08, 3.20-3.35, 3.57, 3.74, 4.02, 4.46, 6.92-7.04, 7.16, 7.36, 7.47, 8.54.

Example 4

5-{[(butyl{1-[(6-{4-[(methylamino)carbonyl]phenoxy}-3-pyridinyl)methyl]-4-piperidinyl}amino) carbonyl]amino}-2,4-difluorobenzamide hydrochloride (or dihydrochloride)

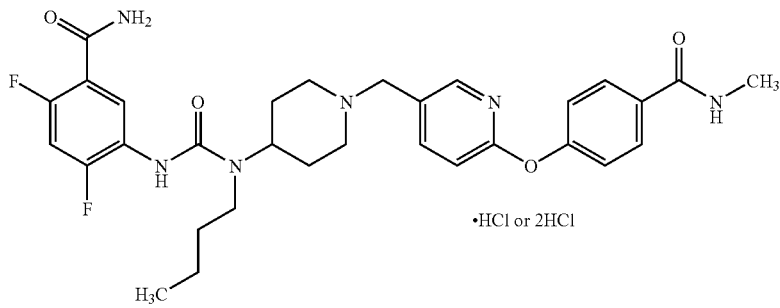

To a solution of the compound prepared in Example 3(53) (132 mg) in dimethylformamide (1 ml) was added 1-hydroxybenzotriazole (46 mg), 1-ethyl-3-[3-(dimethylamino) propyl]carbodiimide hydrochloride (65 mg) and a solution of 33% methylamine in methanol (32 μl). The reaction mixture was stirred for 2.5 hours at room temperature. To the mixture was added a saturated aqueous solution of sodium hydrogen carbonate, and extract with ethyl acetate. The extract was dried over anhydrous sodium sulfate, and concentrated. The obtained residue was purified by column chromatography on silica gel (ethyl acetate:methanol=5:1). To a solution of the obtained compound in ethyl acetate was added 4N hydrogen chloride in ethyl acetate solution. The reaction mixture was concentrated to give the title compound (73 mg) having the following physical data.

TLC: Rf 0.48 (dichloromethane:methanol=9:1);
NMR (CD$_3$OD): δ 0.97, 1.32-1.45, 1.58-1.70, 1.95-2.08, 2.25-2.40, 2.92, 3.10-3.22, 3.27-3.38, 3.58-3.64, 4.24, 4.37, 7.13, 7.15, 7.24, 7.86, 7.90, 8.12, 8.33.

Examples 4(1)-4(9)

By the same procedure as described in Example 4 using the corresponding amine compounds instead of methylamine and the compound prepared in Example 3(53) or the compound prepared in Example 3(47), the following compounds of the present invention were obtained.

Example 4(1)

5-({[[1-({6-[4-(aminocarbonyl)phenoxy]-3-pyridinyl}methyl)-4-piperidinyl](butyl)amino]carbonyl}amino)-2,4-difluorobenzamide hydrochloride (or dihydrochloride)

TLC: Rf 0.47 (dichloromethane:methanol=9:1);
NMR (CD$_3$OD): δ 0.98, 1.35-1.48, 1.59-1.70, 1.95-2.08, 2.19-2.38, 3.06-3.22, 3.24-3.35, 3.55-3.65, 4.18, 4.36, 7.14, 7.16, 7.23, 7.86, 7.96, 8.05, 8.30.

Example 4(2)

5-{[(butyl{1-[(6-{4-[(dimethylamino)carbonyl]phenoxy}-3-pyridinyl)methyl]-4-piperidinyl}amino)carbonyl]amino}-2,4-difluorobenzamide hydrochloride (or dihydrochloride)

TLC: Rf 0.50 (dichloromethane:methanol=9:1);
NMR (CD$_3$OD): δ 0.97, 1.34-1.45, 1.58-1.70, 1.95-2.08, 2.20-2.40, 3.02-3.22, 3.24-3.35, 3.52-3.65, 4.19, 4.36, 7.14, 7.16, 7.25, 7.52, 7.86, 8.09, 8.30.

Example 4(3)

5-[({butyl[1-({6-[4-(4-morpholinylcarbonyl)phenoxy]-3-pyridinyl}methyl)-4-piperidinyl]amino}carbonyl)amino]-2,4-difluorobenzamide hydrochloride (or dihydrochloride)

TLC: Rf 0.50 (dichloromethane:methanol=9:1);
NMR (CD$_3$OD): δ 0.98, 1.32-1.47, 1.59-1.70, 1.95-2.08, 2.20-2.39, 3.10-3.20, 3.25-3.35, 3.45-3.82, 4.18, 4.36, 7.14, 7.16, 7.25, 7.52, 7.86, 8.08, 8.30.

Example 4(4)

5-({[butyl(1-{[6-(4-{[(2-methoxyethyl)amino]carbonyl}phenoxy)-3-pyridinyl]methyl}-4-piperidinyl)amino]carbonyl}amino)-2,4-difluorobenzamide hydrochloride (or dihydrochloride)

TLC: Rf 0.50 (dichloromethane:methanol=9:1);
NMR (CD$_3$OD): δ 0.98, 1.35-1.47, 1.60-1.70, 1.95-2.08, 2.20-2.38, 3.08-3.21, 3.25-3.40, 3.57, 3.51-3.64, 4.16, 4.36, 7.14, 7.16, 7.23, 7.86, 7.90, 8.05, 8.30.

Example 4(5)

5-[({butyl[1-({6-[4-({2-(dimethylamino)ethyl]amino}carbonyl)phenoxy]-3-pyridinyl}methyl)-4-piperidinyl]amino}carbonyl)amino]-2,4-difluorobenzamide dihydrochloride (or trihydrochloride)

TLC: Rf 0.35 (dichloromethane:methanol=5:1);
NMR (CD$_3$OD): δ 0.97, 1.35-1.45, 1.59-1.70, 1.94-2.05, 2.23-2.40, 2.99, 3.10-3.22, 3.22-3.35, 3.40, 3.55-3.65, 3.78, 4.22, 4.37, 7.14, 7.17, 7.27, 7.86, 7.99, 8.13, 8.34.

Example 4(6)

5-({[butyl(1-{[6-(4-{[(2-methoxyethyl)amino]carbonyl}-2,6-dimethylphenoxy)-3-pyridinyl]methyl}-4-piperidinyl)amino]carbonyl}amino)-2,4-difluorobenzamide hydrochloride (or dihydrochloride)

TLC: Rf 0.51 (dichloromethane:methanol=9:1);
NMR (CD$_3$OD): δ 0.97, 1.34-1.46, 1.57-1.68, 1.98-2.08, 2.13, 2.18-2.35, 3.08-3.21, 3.22-3.40, 3.56, 3.51-3.64, 4.17, 4.33, 7.11, 7.14, 7.62, 7.86, 8.06, 8.22.

Example 4(7)

5-({[(1-{4-[4-(aminocarbonyl)-2-methoxyphenoxy]benzyl}-4-piperidinyl)(butyl)amino]carbonyl}amino)-2,4-difluorobenzamide hydrochloride TLC: Rf 0.41 (dichloromethane:methanol=9:1);
NMR (CD$_3$OD): δ 0.98, 1.32-1.47, 1.58-1.70, 1.97-2.05, 2.12-2.31, 3.04-3.18, 3.22-3.35, 3.51-3.60, 3.82, 4.15, 4.27, 6.97, 7.09, 7.14, 7.47, 7.53, 7.65, 7.85.

Example 4(8)

5-{[(butyl{1-[4-(2-methoxy-4-{[(2-methoxyethyl)amino]carbonyl}phenoxy)benzyl]-4-piperidinyl}amino)carbonyl]amino}-2,4-difluorobenzamide hydrochloride TLC: Rf 0.53 (dichloromethane:methanol=9:1);
NMR (CD$_3$OD): δ 0.98, 1.32-1.47, 1.58-1.70, 1.95-2.04, 2.12-2.30, 3.04-3.18, 3.22-3.35, 3.50-3.61, 3.57, 3.82, 4.14, 4.27, 6.97, 7.09, 7.14, 7.45, 7.47, 7.61, 7.85.

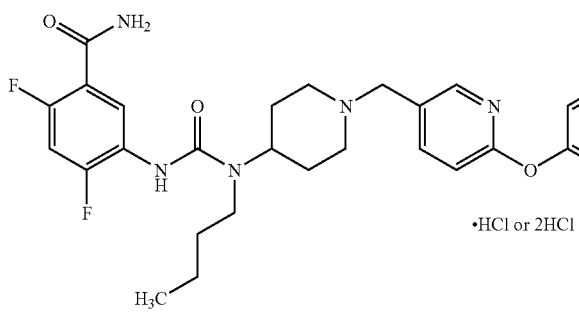

·HCl or 2HCl

Example 4(9)

5-({[butyl(1-{4-[2-methoxy-4-(4-morpholinylcarbonyl)phenoxy]benzyl}-4-piperidinyl)amino]carbonyl}amino)-2,4-difluorobenzamide hydrochloride TLC: Rf 0.52 (dichloromethane:methanol=9:1);

NMR (CD$_3$OD): δ 0.98, 1.32-1.44, 1.58-1.70, 1.95-2.04, 2.12-2.30, 3.04-3.17, 3.22-3.35, 3.47-3.81, 3.79, 4.14, 4.27, 6.97, 7.05, 7.12, 7.14, 7.20, 7.45, 7.85.

Example 5

[[4-(4-{[4-(butyl{[(2,4-difluorophenyl)amino]carbonyl}amino)-1-piperidinyl]methyl}phenoxy)phenyl](methylsulfonyl)amino]acetic acid hydrochloride

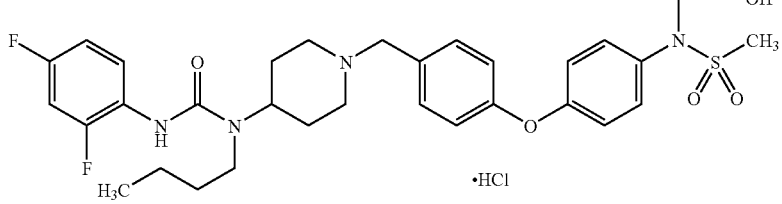

To a solution of the compound prepared in Example 3(106) (80 mg) in methanol (1 ml) was added 2N aqueous solution of sodium hydroxide (0.5 ml). The reaction mixture was stirred for 2.5 hours at room temperature. To the reaction mixture on ice bath was added 1N hydrochloric acid until the pH of the solution was below 5, then it was extracted with ethyl acetate. The extract was dried over anhydrous sodium sulfate, concentrated. The obtained residue was purified by column chromatography on silica gel (dichloromethane:methanol=9:1). To a solution of the obtained compound in ethyl acetate was added 4N hydrogen chloride in ethyl acetate solution. The reaction mixture was concentrated to give the title compound (64 mg) having the following physical data.

TLC: Rf 0.45 (dichloromethane:methanol=9:1);

NMR (CD$_3$OD): δ 0.98, 1.32-1.45, 1.57-1.70, 1.92-2.05, 2.12-2.31, 3.09, 3.06-3.20, 3.22-3.35, 3.51-3.61, 4.17, 4.30, 4.43, 6.88-7.05, 7.06, 7.12, 7.36, 7.51-7.58.

Example 5(1)

[{4-[4-({4-[({[5-(aminocarbonyl)-2,4-difluorophenyl]amino}carbonyl)(butyl)amino]-1-piperidinyl}methyl)phenoxy]phenyl}(methylsulfonyl)amino]acetic acid hydrochloride By the same procedure as described in Example 5 using the compound prepared in Example 3(107), the following the title compound was obtained.

TLC: Rf 0.17 (dichloromethane:methanol=9:1);

NMR (CD$_3$OD): δ 0.97, 1.30-1.42, 1.57-1.70, 1.90-2.02, 2.11-2.30, 2.95-3.10, 3.10, 3.23-3.40, 3.41-3.52, 4.16, 4.21, 4.30, 7.01, 7.06, 7.13, 7.48, 7.57, 7.86.

Example 6(1)-6(20)

By the same procedure as described in Example 3 using the corresponding aldehyde compound instead of the compound prepared in Example 1 and the corresponding amine compound instead of the compound prepared in Example 2, the following compounds of the present invention were obtained.

Example 6(1)

2-(5-{[(butyl{1-[(6-{4-[(methylsulfonyl)amino]phenoxy}-3-pyridinyl)methyl]-4-piperidinyl}amino)carbonyl]amino}-2,4-difluorophenyl)acetamide hydrochloride (or dihydrochloride)

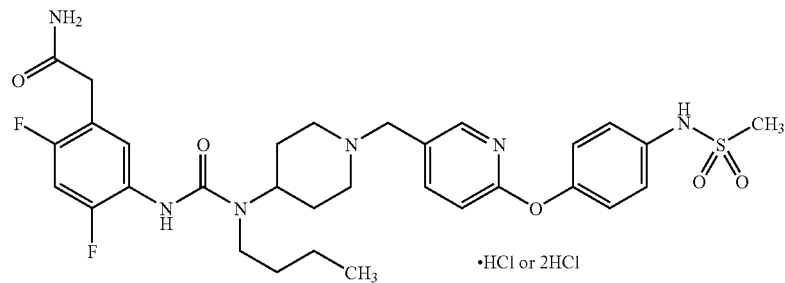

TLC: Rf 0.42 (chloroform:methanol=7:1);

NMR (CD$_3$OD): δ 0.97, 1.30-1.50, 1.50-1.70, 1.95-2.10, 2.15-2.30, 2.97, 3.05-3.20, 3.20-3.40, 3.50-3.60, 3.53, 4.10, 4.33, 7.00, 7.08-7.14, 7.30-7.34, 7.97, 8.24.

Example 6(2)

2-[2,4-difluoro-5-({[{1-[(6-{4-[(methylsulfonyl) amino]phenoxy}-3-pyridinyl)methyl]-4-piperidinyl} (pentyl)amino]carbonyl}amino)phenyl]acetamide hydrochloride (or dihydrochloride)

TLC: Rf 0.43 (chloroform:methanol=7:1);
NMR (CD$_3$OD): δ 0.93, 1.30-1.50, 1.55-1.75, 1.90-2.10, 2.15-2.35, 2.97, 3.10-3.20, 3.20-3.40, 3.50-3.60, 3.53, 4.15, 4.33, 7.00, 7.08-7.14, 7.30-7.34, 7.99, 8.25.

Example 6(3)

5-{[(butyl{1-[(6-{4-[(methylsulfonyl)amino]phenoxy}-3-pyridinyl)methyl]-4-piperidinyl}amino) carbonyl]amino}-2,4-difluoro-N-methylbenzamide hydrochloride (or dihydrochloride)

TLC: Rf 0.41 (chloroform:methanol=7:1);
NMR (CD$_3$OD): δ 0.98, 1.35-1.50, 1.65-1.80, 1.95-2.10, 2.20-2.35, 2.91, 2.97, 3.05-3.20, 3.20-3.40, 3.55-3.70, 4.10, 4.34, 7.08-7.16, 7.32, 7.80, 8.00, 8.24.

Example 6(4)

2,4-difluoro-N-methyl-5-({[{1-[(6-{4-[(methylsulfonyl)amino]phenoxy}-3-pyridinyl)methyl]-4-piperidinyl}(pentyl)amino]carbonyl}amino)benzamide hydrochloride (or dihydrochloride)

TLC: Rf 0.43 (chloroform:methanol=7:1);
NMR (CD$_3$OD): δ 0.93, 1.30-1.50, 1.60-1.75, 1.95-2.10, 2.20-2.40, 2.91, 2.97, 3.05-3.20, 3.20-3.40, 3.50-3.70, 4.15, 4.34, 7.08-7.16, 7.32, 7.79, 8.00, 8.24.

Example 6(5)

5-({[{1-[(6-{4-[(ethylsulfonyl)amino]phenoxy}-3-pyridinyl)methyl]-4-piperidinyl}(pentyl)amino] carbonyl}amino)-2,4-difluoro-N-methylbenzamide hydrochloride (or dihydrochloride)

TLC: Rf 0.45 (chloroform:methanol=7:1);
NMR (CD$_3$OD): δ 0.93, 1.33, 1.30-1.45, 1.60-1.70, 1.90-2.10, 2.15-2.30, 2.91, 3.05-3.20, 3.10, 3.20-3.40, 3.50-3.60, 4.10, 4.33, 7.07-7.16, 7.32, 7.79, 7.97, 8.24.

Example 6(6)

2,4-difluoro-N-methyl-5-({[{1-[(6-{2-methyl-4-[(methylsulfonyl)amino]phenoxy}-3-pyridinyl)methyl]-4-piperidinyl}(pentyl)amino]carbonyl}amino)benzamide hydrochloride (or dihydrochloride)

TLC: Rf 0.45 (chloroform:methanol=7:1);
NMR (CD$_3$OD): δ 0.93, 1.30-1.40, 1.60-1.70, 1.95-2.05, 2.13, 2.20-2.40, 2.91, 2.98, 3.05-3.20, 3.20-3.40, 3.55-3.65, 4.15, 4.34, 7.11-7.21, 7.79, 8.04, 8.26.

Example 6(7)

5-{[(butyl{1-[(6-{2-chloro-4-[(ethylsulfonyl)amino] phenoxy}-3-pyridinyl)methyl]-4-piperidinyl}amino) carbonyl]amino}-2,4-difluorobenzamide hydrochloride (or dihydrochloride)

TLC: Rf 0.46 (dichloromethane:methanol=9:1);
NMR (CD$_3$OD): δ 0.97, 1.33, 1.30-1.47, 1.59-1.70, 1.95-2.08, 2.20-2.37, 3.15, 3.05-3.20, 3.22-3.35, 3.52-3.62, 4.18, 4.34, 7.10-7.28, 7.41, 7.86, 8.05, 8.24.

Example 6(8)

5-({[(1-{4-[4-(aminocarbonyl)phenoxy]benzyl}-4-piperidinyl)(butyl)amino]carbonyl}amino)-2,4-difluorobenzamide hydrochloride TLC: Rf 0.40 (dichloromethane:methanol=9:1);
NMR (CD$_3$OD): δ 0.98, 1.32-1.49, 1.59-1.70, 1.95-2.09, 2.19-2.38, 3.08-3.20, 3.27-3.35, 3.51-3.65, 4.18, 4.32, 7.07, 7.08, 7.16, 7.57, 7.86, 7.91.

Example 6(9)

5-({[butyl(1-{4-[4-(4-morpholinylcarbonyl)phenoxy]benzyl}-4-piperidinyl)amino]carbonyl}amino)-2,4-difluorobenzamide hydrochloride TLC: Rf 0.45 (dichloromethane:methanol=9:1);
NMR (CD$_3$OD): δ 0.98, 1.31-1.47, 1.60-1.70, 1.98-2.07, 2.15-2.30, 3.04-3.20, 3.25-3.35, 3.50-3.80, 4.13, 4.31, 7.08-7.18, 7.48, 7.54, 7.86.

Example 6(10)

2-{5-[({butyl[1-(4-{4-[(methylsulfonyl)amino] phenoxy}benzyl)-4-piperidinyl]amino}carbonyl) amino]-2,4-difluorophenyl}acetamide hydrochloride TLC: Rf 0.42 (chloroform:methanol=7:1);
NMR (CD$_3$OD): δ 0.98, 1.30-1.50, 1.60-1.75, 1.95-2.10, 2.10-2.30, 2.95, 3.05-3.40, 3.53, 3.55-3.65, 4.15, 4.28, 7.00-7.08, 7.28, 7.29, 7.49.

Example 6(11)

2-{5-[({butyl[1-({6-[4-(methylsulfonyl)phenoxy]-3-pyridinyl}methyl)-4-piperidinyl]amino}carbonyl) amino]-2,4-difluorophenyl}acetamide hydrochloride (or dihydrochloride)

TLC: Rf 0.44 (chloroform:methanol=7:1);
NMR (CD$_3$OD): δ 0.98, 1.30-1.50, 1.60-1.70, 1.90-2.10, 2.15-2.30, 3.05-3.40, 3.15, 3.53, 3.55-3.65, 4.15, 4.36, 7.00, 7.23, 7.33, 7.40, 8.01, 8.04, 8.29.

Example 6(12)

2-{5-[({butyl[1-({6-[2-chloro-4-(methylsulfonyl) phenoxy]-3-pyridinyl}methyl)-4-piperidinyl] amino}carbonyl)amino]-2,4-difluorophenyl}acetamide hydrochloride (or dihydrochloride)

TLC: Rf 0.42 (chloroform:methanol=7:1);
NMR (CD$_3$OD): δ 0.98, 1.30-1.50, 1.60-1.70, 1.95-2.10, 2.15-2.35, 3.00-3.40, 3.30, 3.53, 3.55-3.65, 4.15, 4.37, 7.00, 7.25, 7.33, 7.35, 7.53, 8.06, 8.16, 8.31.

Example 6(13)

2-[5-({[{1-[(6-{4-[(ethylsulfonyl)amino]phenoxy}-3-pyridinyl)methyl]-4-piperidinyl}(pentyl)amino] carbonyl}amino)-2,4-difluorophenyl]acetamide hydrochloride (or dihydrochloride)

TLC: Rf 0.33 (chloroform:methanol=7:1);

NMR (CD₃OD): δ 0.93, 1.30-1.50, 1.33, 1.60-1.70, 1.90-2.10, 2.15-2.35, 3.00-3.40, 3.10, 3.53, 3.55-3.65, 4.10, 4.33, 7.00, 7.07-7.13, 7.32, 7.33, 7.97, 8.24.

Example 6(14)

2-[2,4-difluoro-5-({[{1-[(6-{2-methyl-4-[(methylsulfonyl)amino]phenoxy}-3-pyridinyl)methyl]-4-piperidinyl}(pentyl)amino]carbonyl}amino)phenyl]acetamide hydrochloride (or dihydrochloride)

TLC: Rf 0.45 (chloroform:methanol=7:1);
NMR (CD₃OD): δ 0.93, 1.30-1.50, 1.60-1.70, 1.90-2.10, 2.12, 2.20-2.40, 2.97, 3.00-3.40, 3.53, 3.55-3.65, 4.15, 4.33, 6.96-7.21, 7.33, 8.01, 8.24.

Example 6(15)

2-[2,4-difluoro-5-({[[1-({6-[4-(methylsulfonyl)phenoxy]-3-pyridinyl}methyl)-4-piperidinyl](pentyl)amino]carbonyl}amino)phenyl]acetamide hydrochloride (or dihydrochloride)

TLC: Rf 0.39 (chloroform:methanol=7:1);
NMR (CD₃OD): δ 0.93, 1.30-1.50, 1.60-1.70, 1.90-2.10, 2.10-2.30, 3.00-3.40, 3.15, 3.53, 3.55-3.65, 4.15, 4.36, 7.00, 7.22, 7.33, 7.40, 8.01, 8.04, 8.29.

Example 6(16)

2-[5-({[[1-({6-[2-chloro-4-(methylsulfonyl)phenoxy]-3-pyridinyl}methyl)-4-piperidinyl](pentyl)amino]carbonyl}amino)-2,4-difluorophenyl]acetamide hydrochloride (or dihydrochloride)

TLC: Rf 0.44 (chloroform:methanol=7:1);
NMR (CD₃OD): δ 0.94, 1.30-1.50, 1.60-1.70, 1.90-2.10, 2.10-2.30, 3.00-3.40, 3.30, 3.53, 3.55-3.65, 4.10, 4.35, 7.00, 7.25, 7.33, 7.37, 7.52, 8.05, 8.16, 8.31.

Example 6(17)

N'-(4-fluorophenyl)-N-[1-({6-[4-(methylsulfonyl)phenoxy]pyridin-3-yl}methyl)piperidin-4-yl]-N-phenylurea hydrochloride (or dihydrochloride)

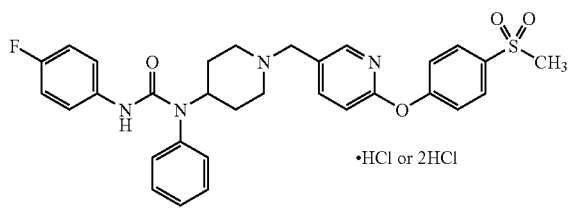

·HCl or 2HCl

TLC: Rf 0.54 (dichloromethane:methanol=9:1);
NMR (CD₃OD): δ 1.62-1.80, 2.14-2.03, 3.14, 3.12-3.25, 3.48-3.58, 4.30, 4.67, 6.95, 7.16-7.25, 7.30-7.40, 7.46-7.58, 7.96, 8.00, 8.22.

Example 6(18)

N-[1-({6-[2-chloro-4-(methylsulfonyl)phenoxy]pyridin-3-yl}methyl)piperidin-4-yl]-N'-(4-fluorophenyl)-N-phenylurea hydrochloride (or dihydrochloride)

TLC: Rf 0.54 (dichloromethane:methanol=9:1);

NMR (CD₃OD): δ 1.62-1.80, 2.15-2.23, 3.12-3.28, 3.31, 3.49-3.59, 4.30, 4.68, 6.95, 7.10, 7.18-7.25, 7.30-7.40, 7.49-7.58, 7.98, 8.15, 8.24.

Example 6(19)

N-[1-({6-[2-chloro-4-(methylsulfonyl)phenoxy]pyridin-3-yl}methyl)piperidin-4-yl]-N'-(2,4-difluorophenyl)-N-phenylurea hydrochloride (or dihydrochloride)

TLC: Rf 0.54 (dichloromethane:methanol=9:1);
NMR (CD₃OD): δ 1.62-1.80, 2.15-2.25, 3.10-3.30, 3.31, 3.50-3.60, 4.31, 4.68, 6.84-6.96, 7.21, 7.30-7.39, 7.48-7.60, 7.98, 8.15, 8.24.

Example 6(20)

5-({[butyl(1-{[6-(4-{[(2-methoxyethyl)amino]carbonyl}-2-methylphenoxy)pyridin-3-yl]methyl}piperidin-4-yl)amino]carbonyl}amino)-2,4-difluorobenzamide hydrochloride (or dihydrochloride)

TLC: Rf 0.52 (dichloromethane:methanol=9:1);
NMR (CD₃OD): δ 0.97, 1.32-1.47, 1.60-1.70, 1.97-2.04, 2.21, 2.20-2.37, 3.10-3.20, 3.21-3.40, 3.57, 3.50-3.62, 4.18, 4.34, 7.10-7.20, 7.72, 7.80, 7.86, 8.06, 8.26.

Example 7(1)-7(121)

By the same procedure as described in Example 3 using the corresponding aldehyde compound instead of the compound prepared in Example 1 and the corresponding amine compound instead of the compound prepared in Example 2, and it was converted into free form, if necessary, the following compounds of the present invention were obtained.

Example 7(1)

5-({[[1-({6-[2,6-dimethyl-4-(methylsulfonyl)phenoxy]-3-pyridinyl}methyl)-4-piperidinyl](pentyl)amino]carbonyl}amino)-2,4-difluorobenzamide hydrochloride (or dihydrochloride)

TLC: Rf 0.42 (chloroform:methanol=7:1);
NMR (CD₃OD): δ 0.93, 1.30-1.50, 1.60-1.80, 1.95-2.10, 2.17, 2.20-2.35, 3.00-3.40, 3.14, 3.50-3.70, 4.15, 4.33, 7.14, 7.21, 7.74, 7.86, 8.07, 8.18.

Example 7(2)

5-({[[1-({6-[2-chloro-4-(methylsulfonyl)phenoxy]-3-pyridinyl}methyl)-4-piperidinyl](pentyl)amino]carbonyl}amino)-2,4-difluorobenzamide hydrochloride (or dihydrochloride)

TLC: Rf 0.48 (chloroform:methanol=7:1);
NMR (CD₃OD): δ 0.93, 1.30-1.50, 1.60-1.80, 1.95-2.10, 2.20-2.40, 3.10-3.40, 3.30, 3.50-3.70, 4.15, 4.37, 7.14, 7.25, 7.35, 7.53, 7.86, 8.10, 8.16, 8.32.

Example 7(3)

5-[({butyl[1-({6-[2-chloro-4-(methylsulfonyl)phenoxy]-3-pyridinyl}methyl)-4-piperidinyl]amino}carbonyl)amino]-2-fluorobenzamide hydrochloride (or dihydrochloride)

TLC: Rf 0.35 (chloroform:methanol=7:1);

NMR (CD$_3$OD): δ 0.97, 1.30-1.50, 1.60-1.80, 1.95-2.10, 2.20-2.40, 3.10-3.40, 3.30, 3.50-3.70, 4.15, 4.36, 7.14, 7.25, 7.35, 7.50, 7.53, 7.78, 8.07, 8.16, 8.32.

Example 7(4)

5-[({butyl[1-({6-[2-methyl-4-(methylsulfonyl)phenoxy]-3-pyridinyl}methyl)-4-piperidinyl]amino}carbonyl)amino]-2-fluorobenzamide hydrochloride (or dihydrochloride)

TLC: Rf 0.36 (chloroform:methanol=7:1);
NMR (CD$_3$OD): δ 0.97, 1.30-1.50, 1.55-1.70, 1.90-2.10, 2.20-2.40, 2.26, 3.00-3.40, 3.14, 3.50-3.70, 4.20, 4.35, 7.11-7.30, 7.53, 7.76-7.85, 7.92, 8.07, 8.24.

Example 7(5)

2,4-difluoro-5-{[(hexyl{1-[(6-{4-[(methylsulfonyl)amino]phenoxy}-3-pyridinyl)methyl]-4-piperidinyl}amino)carbonyl]amino}benzamide hydrochloride (or dihydrochloride)

TLC: Rf 0.37 (chloroform:methanol=7:1);
NMR (CD$_3$OD): δ 0.98, 1.30-1.50, 1.60-1.70, 1.90-2.05, 2.20-2.35, 2.97, 3.00-3.35, 3.50-3.70, 4.20, 4.34, 7.08-7.17, 7.32, 7.86, 8.02, 8.24.

Example 7(6)

2,4-difluoro-5-{[((2-methylbenzyl){1-[(6-{4-[(methylsulfonyl)amino]phenoxy}-3-pyridinyl)methyl]-4-piperidinyl}amino)carbonyl]amino}benzamide hydrochloride (or dihydrochloride)

TLC: Rf 0.53 (dichloromethane:methanol=9:1);
NMR (CD$_3$OD): δ 1.98-2.20, 2.36, 2.97, 3.04-3.18, 3.48-3.57, 4.30, 4.43, 4.57, 7.04-7.33, 7.85, 7.98, 8.23.

Example 7(7)

2,4-difluoro-5-({[[1-({6-[2-methyl-4-(methylsulfonyl)phenoxy]-3-pyridinyl}methyl)-4-piperidinyl](pentyl)amino]carbonyl}amino)benzamide hydrochloride (or dihydrochloride)

TLC: Rf 0.38 (chloroform:methanol=7:1);
NMR (CD$_3$OD): δ 0.94, 1.30-1.50, 1.60-1.80, 1.90-2.10, 2.26, 2.20-2.40, 3.05-3.40, 3.14, 3.50-3.70, 4.15, 4.33, 7.11-7.29, 7.81-7.89, 7.92, 8.03, 8.23.

Example 7(8)

2,4-difluoro-5-{[({1-[(6-{4-[(methylsulfonyl)amino]phenoxy}-3-pyridinyl)methyl]-4-piperidinyl}amino)carbonyl]amino}benzamide hydrochloride (or dihydrochloride)

TLC: Rf 0.37 (dichloromethane:methanol=9:1);
NMR (CD$_3$OD): δ 1.65-1.80, 2.20-2.30, 2.98, 3.08-3.21, 3.50-3.60, 3.83, 4.34, 7.07-7.19, 7.33, 8.02, 8.27, 8.38.

Example 7(9)

N'-(4-fluorophenyl)-N-[1-({6-[2-methoxy-4-(methylsulfonyl)phenoxy]-3-pyridinyl}methyl)-4-piperidinyl]-N-phenylurea hydrochloride (or dihydrochloride)

TLC: Rf 0.55 (dichloromethane:methanol=9:1);
NMR (CD$_3$OD): δ 1.64-1.80, 2.12-2.22, 3.17, 3.10-3.25, 3.48-3.58, 3.79, 4.27, 4.67, 6.95, 7.12, 7.22, 7.30-7.38, 7.45-7.64, 7.93, 8.12.

Example 7(10)

N'-(2,4-difluorophenyl)-N-[1-({6-[2-methyl-4-(methylsulfonyl)phenoxy]-3-pyridinyl}methyl)-4-piperidinyl]-N-phenylurea hydrochloride (or dihydrochloride)

TLC: Rf 0.56 (dichloromethane:methanol=9:1);
NMR (CD$_3$OD): δ 1.65-1.80, 2.15-2.28, 2.24, 3.13, 3.12-3.24, 3.50-3.58, 4.29, 4.68, 6.85-6.98, 7.17, 7.26, 7.34-7.38, 7.48-7.60, 7.81, 7.91, 7.98, 8.17.

Example 7(11)

N'-(2,4-difluorophenyl)-N-[1-({6-[2,6-dimethyl-4-(methylsulfonyl)phenoxy]-3-pyridinyl}methyl)-4-piperidinyl]-N-phenylurea hydrochloride (or dihydrochloride)

TLC: Rf 0.56 (dichloromethane:methanol=9:1);
NMR (CD$_3$OD): δ 1.62-1.80, 2.15, 2.12-2.23, 3.13, 3.10-3.24, 3.50-3.58, 4.27, 4.68, 6.85-6.98, 7.18, 7.33-7.37, 7.50-7.60, 7.73, 7.96, 8.11.

Example 7(12)

N'-(2,4-difluorophenyl)-N-[1-({6-[2-methoxy-4-(methylsulfonyl)phenoxy]-3-pyridinyl}methyl)-4-piperidinyl]-N-phenylurea hydrochloride (or dihydrochloride)

TLC: Rf 0.55 (dichloromethane:methanol=9:1);
NMR (CD$_3$OD): δ 1.64-1.80, 2.15-2.24, 3.17, 3.12-3.25, 3.48-3.58, 3.79, 4.28, 4.68, 6.85-6.98, 7.12, 7.33-7.37, 7.50-7.60, 7.95, 8.13.

Example 7(13)

2,4-difluoro-5-[({hexyl[1-({6-[2-methoxy-4-(methylsulfonyl)phenoxy]-3-pyridinyl}methyl)-4-piperidinyl]amino}carbonyl)amino]benzamide hydrochloride (or dihydrochloride)

TLC: Rf 0.35 (chloroform:methanol=7:1);
NMR (CD$_3$OD): δ 0.91, 1.25-1.45, 1.60-1.75, 1.90-2.10, 2.20-2.40, 3.05-3.40, 3.14, 3.50-3.70, 3.81, 4.15, 4.35, 7.14, 7.15, 7.38, 7.60-7.65, 7.86, 8.09, 8.24.

Example 7(14)

N'-(4-fluorophenyl)-N-[1-({6-[2-methyl-4-(methylsulfonyl)phenoxy]-3-pyridinyl}methyl)-4-piperidinyl]-N-phenylurea hydrochloride (or dihydrochloride)

TLC: Rf 0.75 (dichloromethane:methanol=9:1);

NMR (CD₃OD): δ 1.63-1.80, 2.12-2.23, 2.24, 3.13, 3.10-3.25, 3.48-3.57, 4.29, 4.67, 6.95, 7.15-7.35, 7.47-7.60, 7.81, 7.91, 7.97, 8.17.

Example 7(15)

N-[1-({6-[2,6-dimethyl-4-(methylsulfonyl)phenoxy]-3-pyridinyl}methyl)-4-piperidinyl]-N'-(4-fluorophenyl)-N-phenylurea hydrochloride (or dihydrochloride)

TLC: Rf 0.75 (dichloromethane:methanol=9:1);
NMR (CD₃OD): δ 1.64-1.80, 2.15, 2.10-2.23, 3.13, 3.10-3.25, 3.48-3.58, 4.27, 4.67, 6.95, 7.15-7.25, 7.30-7.35, 7.48-7.60, 7.73, 7.97, 8.11.

Example 7(16)

5-{[(butyl{1-[(2-methyl-6-{4-[(methylsulfonyl)amino]phenoxy}-3-pyridinyl)methyl]-4-piperidinyl}amino)carbonyl]amino}-2,4-difluorobenzamide hydrochloride (or dihydrochloride)

TLC: Rf 0.56 (dichloromethane:methanol=9:1);
NMR (CD₃OD): δ 0.98, 1.32-1.45, 1.58-1.70, 1.95-2.05, 2.24-2.40, 2.67, 2.99, 3.20-3.35, 3.60-3.69, 4.28, 4.43, 6.95, 7.14, 7.22, 7.37, 7.87, 8.20.

Example 7(17)

4-chloro-2-fluoro-5-({[[1-({6-[2-methyl-4-(methylsulfonyl)phenoxy]-3-pyridinyl}methyl)-4-piperidinyl](pentyl)amino]carbonyl}amino)benzamide hydrochloride (or dihydrochloride)

TLC: Rf 0.55 (dichloromethane:methanol=9:1);
NMR (CD₃OD): δ 0.94, 1.30-1.50, 1.67-1.80, 1.98-2.06, 2.26, 2.19-2.38, 3.10-3.20, 3.14, 3.25-3.35, 3.55-3.65, 4.20, 4.34, 7.21, 7.28, 7.41, 7.83, 7.90-7.99, 8.06, 8.24.

Example 7(18)

4-chloro-5-({[[1-({6-[2,6-dimethyl-4-(methylsulfonyl)phenoxy]-3-pyridinyl}methyl)-4-piperidinyl](pentyl)amino]carbonyl}amino)-2-fluorobenzamide hydrochloride (or dihydrochloride)

TLC: Rf 0.55 (dichloromethane:methanol=9:1);
NMR (CD₃OD): δ 0.94, 1.30-1.47, 1.65-1.80, 1.98-2.08, 2.17, 2.15-2.35, 3.08-3.20, 3.13, 3.25-3.35, 3.55-3.65, 4.19, 4.33, 7.21, 7.41, 7.74, 7.97, 8.06, 8.18.

Example 7(19)

5-{[(butyl{1-[(6-{4-[(methylsulfonyl)amino]phenoxy}-3-pyridinyl)methyl]-4-piperidinyl}amino)carbonyl]amino}-4-chloro-2-fluorobenzamide hydrochloride (or dihydrochloride)

TLC: Rf 0.54 (dichloromethane:methanol=9:1);
NMR (CD₃OD): δ 0.98, 1.35-1.48, 1.62-1.75, 1.98-2.08, 2.19-2.38, 2.97, 3.08-3.20, 3.25-3.35, 3.55-3.63, 4.17, 4.34, 7.09, 7.13, 7.32, 7.42, 7.94, 8.02, 8.27.

Example 7(20)

5-[({butyl[1-({6-[4-(methylsulfonyl)phenoxy]-3-pyridinyl}methyl)-4-piperidinyl]amino}carbonyl)amino]-4-chloro-2-fluorobenzamide hydrochloride (or dihydrochloride)

TLC: Rf 0.54 (dichloromethane:methanol=9:1);
NMR (CD₃OD): δ 0.99, 1.38-1.50, 1.64-1.75, 1.98-2.07, 2.20-2.38, 3.15, 3.08-3.20, 3.25-3.35, 3.58-3.65, 4.18, 4.36, 7.22, 7.40, 7.41, 7.94, 8.02, 8.07, 8.30.

Example 7(21)

5-[({butyl[1-({6-[2-chloro-4-(methylsulfonyl)phenoxy]-3-pyridinyl}methyl)-4-piperidinyl]amino}carbonyl)amino]-4-chloro-2-fluorobenzamide hydrochloride (or dihydrochloride)

TLC: Rf 0.55 (dichloromethane:methanol=9:1);
NMR (CD₃OD): δ 0.99, 1.38-1.45, 1.64-1.75, 1.98-2.07, 2.20-2.38, 3.08-3.22, 3.25-3.35, 3.31, 3.58-3.65, 4.18, 4.37, 7.25, 7.36, 7.41, 7.53, 7.94, 8.09, 8.16, 8.32.

Example 7(22)

5-[({butyl[1-({6-[2,6-dimethyl-4-(methylsulfonyl)phenoxy]-3-pyridinyl}methyl)-4-piperidinyl]amino}carbonyl)amino]-4-chloro-2-fluorobenzamide hydrochloride (or dihydrochloride)

TLC: Rf 0.56 (dichloromethane:methanol=9:1);
NMR (CD₃OD): δ 0.98, 1.35-1.48, 1.62-1.75, 1.97-2.08, 2.17, 2.19-2.38, 3.08-3.21, 3.14, 3.25-3.35, 3.52-3.65, 4.19, 4.33, 7.21, 7.41, 7.73, 7.94, 8.07, 8.18.

Example 7(23)

N-(4-{[5-({4-[{[(4-fluorophenyl)amino]carbonyl}(phenyl)amino]-1-piperidinyl}methyl)-2-pyrazinyl]oxy}phenyl)methanesulfonamide dihydrochloride TLC: Rf 0.50 (dichloromethane:methanol=9:1);
NMR (CD₃OD): δ 1.70-1.84, 2.14-2.23, 2.97, 3.20-3.35, 3.55-3.65, 4.40, 4.68, 6.95, 7.17, 7.22, 7.29-7.38, 7.48-7.60, 8.19, 8.48.

Example 7(24)

N-(4-{[5-({4-[[(cyclohexylamino)carbonyl](phenyl)amino]-1-piperidinyl}methyl)-2-pyridinyl]oxy}phenyl)methanesulfonamide hydrochloride (or dihydrochloride)

TLC: Rf 0.51 (dichloromethane:methanol=9:1);
NMR (CD₃OD): δ 0.93-1.15, 1.20-1.38, 1.49-1.80, 2.08-2.18, 2.97, 3.10-3.21, 3.47-3.58, 4.28, 4.62, 7.07, 7.12, 7.18-7.25, 7.33, 7.42-7.55, 7.98, 8.23.

Example 7(25)

N-[4-({5-[(4-{phenyl[(3-thienylamino)carbonyl]amino}-1-piperidinyl)methyl]-2-pyridinyl}oxy)phenyl]methanesulfonamide hydrochloride (or dihydrochloride)

TLC: Rf 0.50 (dichloromethane:methanol=9:1);
NMR (CD$_3$OD): δ 1.64-1.80, 2.12-2.20, 2.98, 3.12-3.26, 3.50-3.59, 4.32, 4.68, 6.91, 7.10, 7.04-7.20, 7.27-7.37, 7.48-7.60, 8.07, 8.31.

Example 7(26)

N-(4-{[5-({4-[(anilinocarbonyl)(phenyl)amino]-1-piperidinyl}methyl)-2-pyridinyl]oxy}phenyl)methanesulfonamide hydrochloride (or dihydrochloride)

TLC: Rf 0.56 (dichloromethane:methanol=9:1);
NMR (CD$_3$OD): δ 1.62-1.80, 2.15-2.24, 2.97, 3.12-3.23, 3.49-3.57, 4.27, 4.68, 6.97-7.14, 7.18-7.22, 7.28-7.38, 7.48-7.60, 7.89, 8.17.

Example 7(27)

N-(4-{[5-({4-[[(benzylamino)carbonyl](phenyl)amino]-1-piperidinyl}methyl)-2-pyridinyl]oxy}phenyl)methanesulfonamide hydrochloride (or dihydrochloride)

TLC: Rf 0.55 (dichloromethane:methanol=9:1);
NMR (CD$_3$OD): δ 1.60-1.78, 2.08-2.18, 2.97, 3.08-3.21, 3.48-3.55, 4.25, 4.29, 4.64, 7.08, 7.10-7.27, 7.32, 7.40-7.58, 8.01, 8.27.

Example 7(28)

N-{4-[(5-{[4-(phenyl{[(2-phenylethyl)amino]carbonyl}amino)-1-piperidinyl]methyl}-2-pyridinyl)oxy]phenyl}methanesulfonamide hydrochloride (or dihydrochloride)

TLC: Rf 0.55 (dichloromethane:methanol=9:1);
NMR (CD$_3$OD): δ 1.57-1.73, 2.04-2.13, 2.67, 2.98, 3.10-3.22, 3.27-3.35, 3.48-3.55, 4.31, 4.60, 7.04-7.25, 7.34, 7.40-7.47, 8.06, 8.31.

Example 7(29)

N-(4-{[5-({4-[{[(4-fluorophenyl)amino]carbonyl}(3-thienyl)amino]-1-piperidinyl}methyl)-2-pyridinyl]oxy}phenyl)methanesulfonamide hydrochloride (or dihydrochloride)

TLC: Rf 0.30 (chloroform:methanol=10:1);
NMR (CD$_3$OD): δ 1.60-1.80, 2.10-2.20, 2.97, 3.10-3.25, 3.50-3.60, 4.29, 4.65, 6.93-7.13, 7.22-7.33, 7.53, 7.61, 7.94, 8.21.

Example 7(30)

N-[4-({5-[(4-{3-thienyl[(3'-thienylamino)carbonyl]amino}-1-piperidinyl)methyl]-2-pyridinyl}oxy)phenyl]methanesulfonamide hydrochloride (or dihydrochloride)

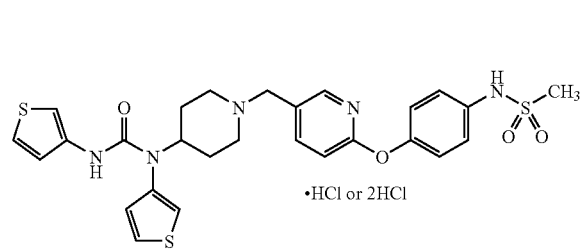

TLC: Rf 0.55 (dichloromethane:methanol=9:1);
NMR (CD$_3$OD): δ 1.62-1.78, 2.11-2.20, 2.97, 3.12-3.25, 3.48-3.58, 4.28, 4.67, 6.95, 7.00, 7.06, 7.11, 7.17-7.23, 7.31, 7.49, 7.60, 7.90, 8.18.

Example 7(31)

N-(4-{[5-({4-[{[(3-fluorophenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.56 (dichloromethane:methanol=9:1);
NMR (CD$_3$OD): δ 1.62-1.80, 2.12-2.24, 2.97, 3.12-3.25, 3.48-3.58, 4.27, 4.68, 6.72, 6.93, 7.03-7.35, 7.48-7.60, 7.89, 8.17.

Example 7(32)

N-(4-{[5-({4-[{[(2-fluorophenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.56 (dichloromethane:methanol=9:1);
NMR (CD$_3$OD): δ 1.63-1.80, 2.18-2.25, 2.97, 3.12-3.25, 3.48-3.58, 4.28, 4.69, 6.98-7.15, 7.31, 7.35-7.40, 7.50-7.62, 7.73, 7.90, 8.17.

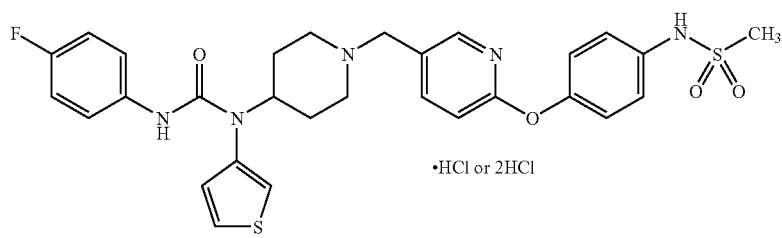

Example 7(33)

N-(4-{[5-({4-[{[(4-methoxyphenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.48 (dichloromethane:methanol=9:1);
NMR (CD$_3$OD): δ 1.62-1.80, 2.13-2.21, 2.97, 3.12-3.25, 3.48-3.57, 3.73, 4.27, 4.67, 6.79, 7.05, 7.09, 7.10, 7.28-7.35, 7.47-7.58, 7.90, 8.17.

Example 7(34)

N-(4-{[5-({4-[{[(3-methoxyphenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.48 (dichloromethane:methanol=9:1);
NMR (CD$_3$OD): δ 1.62-1.80, 2.13-2.25, 2.97, 3.12-3.25, 3.48-3.57, 3.72, 4.28, 4.67, 6.58, 6.73, 6.94, 7.04-7.15, 7.29-7.35, 7.49-7.60, 7.90, 8.18.

Example 7(35)

N-(4-{[5-({4-[{[(2-methoxyphenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.48 (dichloromethane:methanol=9:1);
NMR (CD$_3$OD): δ 1.62-1.80, 2.15-2.27, 2.97, 3.12-3.25, 3.50-3.60, 3.55, 4.29, 4.71, 6.80-6.97, 7.05, 7.11, 7.31, 7.37, 7.51-7.64, 7.91, 7.95, 8.18.

Example 7(36)

N-(4-{[5-({4-[{[(4-methylphenyl)amino]carbonyl}(phenyl)amino]-1-piperidinyl}methyl)-2-pyridinyl]oxy}phenyl)methanesulfonamide Amorphous powder;
TLC: Rf 0.48 (dichloromethane:methanol=9:1);
NMR (CD$_3$OD): δ 1.34-1.50, 1.80-1.91, 2.10-2.20, 2.23, 2.83-2.98, 2.95, 3.44, 4.43, 6.88, 6.98-7.10, 7.28, 7.45-7.57, 7.73, 7.98.

Example 7(37)

N-(4-{[5-({4-[{[(3-methylphenyl)amino]carbonyl}(phenyl)amino]-1-piperidinyl}methyl)-2-pyridinyl]oxy}phenyl)methanesulfonamide TLC: Rf 0.48 (dichloromethane:methanol=9:1);
NMR (CD$_3$OD): δ 1.35-1.50, 1.80-1.91, 2.08-2.20, 2.24, 2.84-2.98, 2.94, 3.44, 4.43, 6.80, 6.87, 6.97-7.12, 7.26-7.34, 7.44-7.58, 7.73, 7.98.

Example 7(38)

N-(4-{[5-({4-[{[(2-methylphenyl)amino]carbonyl}(phenyl)amino]-1-piperidinyl}methyl)-2-pyridinyl]oxy}phenyl)methanesulfonamide TLC: Rf 0.48 (dichloromethane:methanol=9:1);
NMR (CD$_3$OD): δ 1.38-1.54, 1.84-1.96, 1.91, 2.10-2.20, 2.85-2.98, 2.95, 3.44, 4.43, 6.88, 6.97, 7.02-7.14, 7.28, 7.35, 7.42-7.60, 7.73, 7.98.

Example 7(39)

N-(4-{[5-({4-[{[(4-chlorophenyl)amino]carbonyl}(phenyl)amino]-1-piperidinyl}methyl)-2-pyridinyl]oxy}phenyl)methanesulfonamide White amorphous powder;

TLC: Rf 0.52 (dichloromethane:methanol=9:1);
NMR (CDCl$_3$): δ 1.32-1.48, 1.80-1.89, 2.08-2.20, 2.82-2.90, 3.01, 3.40, 4.53, 5.83, 6.43, 6.85, 7.08-7.28, 7.44-7.55, 7.61, 8.00.

Example 7(40)

N-(4-{[5-({4-[{[(3-chlorophenyl)amino]carbonyl}(phenyl)amino]-1-piperidinyl}methyl)-2-pyridinyl]oxy}phenyl)methanesulfonamide TLC: Rf 0.52 (dichloromethane:methanol=9:1);
NMR (CDCl$_3$): δ 1.32-1.50, 1.80-1.90, 2.08-2.20, 2.82-2.90, 3.01, 3.41, 4.53, 5.85, 6.52, 6.85, 6.94, 7.02-7.15, 7.19-7.28, 7.35, 7.44-7.55, 7.61, 8.01.

Example 7(41)

N-(4-{[5-({4-[{[(2-chlorophenyl)amino]carbonyl}(phenyl)amino]-1-piperidinyl}methyl)-2-pyridinyl]oxy}phenyl)methanesulfonamide TLC: Rf 0.52 (dichloromethane:methanol=9:1);
NMR (CDCl$_3$): δ 1.38-1.53, 1.82-1.90, 2.08-2.20, 2.83-2.92, 3.01, 3.41, 4.53, 6.47, 6.59, 6.85, 6.87, 7.12, 7.18, 7.22-7.28, 7.42-7.55, 7.61, 8.01, 8.27.

Example 7(42)

N-(4-{[5-({4-[{[(4-fluorophenyl)amino]carbonyl}(1-methyl-1H-pyrazol-4-yl)amino]-1-piperidinyl}methyl)-2-pyridinyl]oxy}phenyl)methanesulfonamide TLC: Rf 0.40 (dichloromethane:methanol=9:1);
NMR (CDCl$_3$): δ 1.30-1.48, 1.70-1.80, 2.08-2.19, 2.81-2.90, 3.01, 3.41, 3.96, 4.46, 6.26, 6.35, 6.85, 6.92, 7.11, 7.18-7.28, 7.37, 7.61, 8.01.

Example 7(43)

2-fluoro-5-({[{1-[(6-{4-[(methylsulfonyl)amino]phenoxy}-3-pyridinyl)methyl]-4-piperidinyl}(phenyl)amino]carbonyl}amino)benzamide

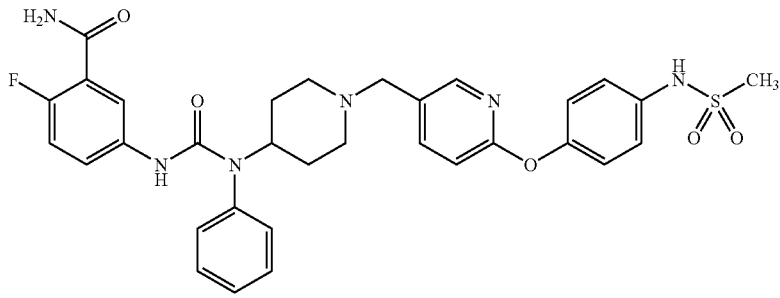

Free form;
White amorphous powder;
TLC: Rf 0.45 (dichloromethane:methanol=9:1);
NMR (CDCl$_3$): δ 1.32-1.48, 1.80-1.90, 2.08-2.20, 2.81-2.92, 3.00, 3.40, 4.55, 5.86, 5.97, 6.62-6.77, 6.85, 7.06, 7.11, 7.18-7.30, 7.34, 7.45-7.55, 7.61, 8.00, 8.04.
Hydrochloride (or dihydrochloride);
White amorphous powder;
TLC: Rf 0.45 (dichloromethane:methanol=9:1);
NMR (CD$_3$OD): δ 1.62-1.81, 2.12-2.23, 2.97, 3.12-3.35, 3.47-3.58, 4.29, 4.67, 7.07-7.16, 7.29-7.36, 7.43, 7.48-7.58, 7.68, 7.95, 8.22.

Example 7(44)

4-fluoro-N-{1-[(6-{4-[(methylsulfonyl)amino]phenoxy}-3-pyridinyl)methyl]-4-piperidinyl}-N-phenylbenzamide TLC: Rf 0.58 (chloroform:methanol=7:1);
NMR (CDCl$_3$): δ 1.50-1.70, 1.85-1.95, 2.10-2.30, 2.85-2.95, 2.98, 3.41, 4.72, 6.75-6.84, 6.95-6.98, 7.07, 7.19-7.25, 7.59, 7.99.

Example 7(45)

N-[4-({5-[(4-{phenyl[(3-pyridinylamino)carbonyl]amino}-1-piperidinyl)methyl]-2-pyridinyl}oxy)phenyl]methanesulfonamide TLC: Rf 0.40 (dichloromethane:methanol=9:1);
NMR (CDCl$_3$): δ 1.34-1.50, 1.80-1.90, 2.10-2.20, 2.80-2.90, 3.00, 3.40, 4.54, 5.87, 6.83, 7.09, 7.18, 7.20-7.28, 7.45-7.55, 7.59, 7.91, 7.99, 8.16, 8.20.

Example 7(46)

N-(4-{[5-({4-[(aminocarbonyl)(phenyl)amino]-1-piperidinyl}methyl)-2-pyridinyl]oxy}phenyl)methanesulfonamide TLC: Rf 0.38 (dichloromethane:methanol=9:1);
NMR (CDCl$_3$): δ 1.30-1.44, 1.76-1.85, 2.08-2.18, 2.80-2.88, 3.01, 3.39, 4.20, 4.48, 6.83, 6.90, 7.11, 7.13-7.18, 7.22-7.28, 7.35-7.45, 7.59, 7.98.

Example 7(47)

N-(4-{[5-({4-[{[(4-fluorophenyl)amino]carbonyl}(4-methoxyphenyl)amino]-1-piperidinyl}methyl)-2-pyridinyl]oxy}phenyl)methanesulfonamide TLC: Rf 0.43 (dichloromethane:methanol=9:1);
NMR (CDCl$_3$): δ 1.31-1.49, 1.77-1.86, 2.09-2.18, 2.81-2.90, 3.01, 3.40, 3.86, 4.50, 5.85, 6.38, 6.84, 6.89, 6.96, 7.08-7.25, 7.60, 7.99.

Example 7(48)

N-(4-{[5-({4-[{[(4-fluorophenyl)amino]carbonyl}(3-methoxyphenyl)amino]-1-piperidinyl}methyl)-2-pyridinyl]oxy}phenyl)methanesulfonamide TLC: Rf 0.43 (dichloromethane:methanol=9:1);
NMR (CDCl$_3$): δ 1.37-1.51, 1.80-1.89, 2.08-2.18, 2.81-2.90, 3.01, 3.40, 3.83, 4.51, 5.87, 6.38, 6.73, 6.80, 6.84, 6.90, 6.98, 7.08-7.26, 7.37, 7.60, 8.00.

Example 7(49)

N-(4-{[5-({3-[{[(4-fluorophenyl)amino]carbonyl}(phenyl)amino]-8-azabicyclo[3.2.1]oct-8-yl}methyl)-2-pyridinyl]oxy}phenyl)methanesulfonamide hydrochloride (or dihydrochloride)

TLC: Rf 0.29 (chloroform:methanol=10:1);
NMR (CD$_3$OD): δ 1.90-2.05, 2.20-2.30, 2.35-2.50, 2.60-2.75, 2.97, 3.85-3.95, 4.16, 4.55, 6.92-6.98, 7.06-7.14, 7.19-7.24, 7.29-7.33, 7.36-7.40, 7.48-7.58, 8.01, 8.25.

Example 7(50)

4-{[5-({4-[{[(4-fluorophenyl)amino]carbonyl}(phenyl)amino]-1-piperidinyl}methyl)-2-pyridinyl]oxy}benzoic acid hydrochloride (or dihydrochloride)

TLC: Rf 0.39 (chloroform:methanol=10:1);
NMR (CD$_3$OD): δ 1.65-1.80, 2.10-2.25, 3.10-3.30, 3.50-3.60, 4.30, 4.65, 6.92-6.98, 7.13, 7.19-7.24, 7.31-7.34, 7.49-7.55, 7.96, 8.08, 8.25.

Example 7(51)

N-(4-{[5-({4-[{[(2,4-difluorophenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.63 (chloroform:methanol=10:1);
NMR (CD$_3$OD): δ 1.65-1.80, 2.10-2.30, 2.98, 3.10-3.30, 3.50-3.60, 4.31, 4.70, 6.88-6.92, 7.09, 7.15, 7.32-7.34, 7.33, 7.51-7.58, 8.04, 8.29.

Example 7(52)

N-(4-{[5-({4-[{[(3-fluoro-4-methoxyphenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.50 (dichloromethane:methanol=9:1);
NMR (CD$_3$OD): δ 1.65-1.82, 2.12-2.22, 2.98, 3.12-3.28, 3.48-3.58, 3.79, 4.32, 4.67, 6.84-6.96, 7.09, 7.13-7.22, 7.28-7.38, 7.45-7.58, 8.05, 8.30.

Example 7(53)

N-(4-{[5-({4-[{[(3-chloro-4-methoxyphenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.50 (dichloromethane:methanol=9:1);
NMR (CD$_3$OD): δ 1.68-1.82, 2.12-2.22, 2.98, 3.12-3.28, 3.48-3.58, 3.81, 4.32, 4.68, 6.92, 7.06, 7.09, 7.16, 7.30-7.38, 7.45-7.58, 8.05, 8.30.

Example 7(54)

N-(4-{[5-({4-[{[(6-methyl-3-pyridinyl)amino]carbonyl}(phenyl)amino]-1-piperidinyl}methyl)-2-pyridinyl]oxy}phenyl)methanesulfonamide dihydrochloride (or trihydrochloride)

Amorphous powder;

TLC: Rf 0.48 (dichloromethane:methanol=9:1);

NMR (CD$_3$OD): δ 1.68-1.85, 2.12-2.25, 2.68, 2.97, 3.15-3.28, 3.50-3.60, 4.31, 4.71, 7.07, 7.13, 7.29-7.38, 7.50-7.62, 7.73, 8.01, 8.25, 8.31, 8.97.

Example 7(55)

N-(4-{[5-({4-[{[(4-fluorophenyl)amino]carbonyl}(phenyl)amino]-1-piperidinyl}methyl)-2-pyridinyl]oxy}phenyl)acetamide hydrochloride (or dihydrochloride)

Amorphous powder;

TLC: Rf 0.23 (chloroform:methanol=10:1);

NMR (CD$_3$OD): δ 1.60-1.80, 2.10-2.25, 3.10-3.25, 3.50-3.60, 3.55, 4.28, 4.70, 6.95, 7.04-7.10, 7.19-7.24, 7.31-7.38, 7.49-7.55, 7.93, 8.21.

Example 7(56)

N-{4-[4-({4-[{[(4-fluorophenyl)amino]carbonyl}(phenyl)amino]-1-piperidinyl}methyl)-3,5-dimethyl-1H-pyrazol-1-yl]phenyl}methanesulfonamide dihydrochloride

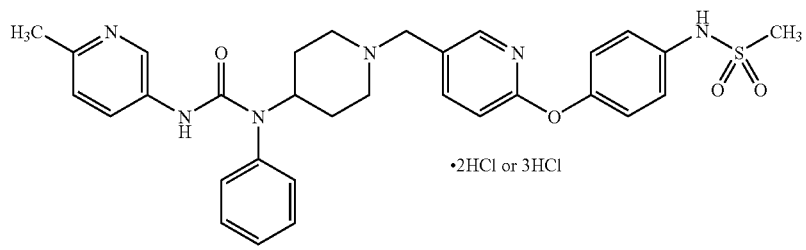

•2HCl or 3HCl

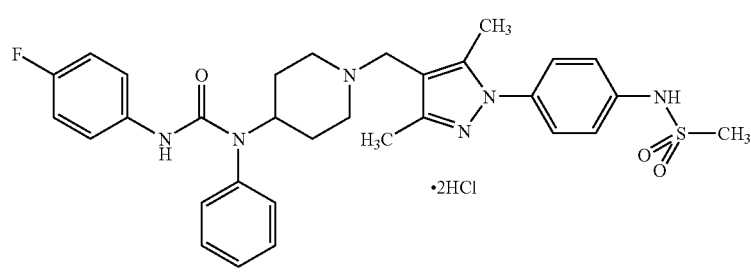

•2HCl

TLC: Rf 0.21 (chloroform:methanol=10:1);
NMR (CD₃OD): δ 1.70-1.85, 2.10-2.25, 2.31, 2.33, 3.03, 3.20-3.35, 3.55-3.65, 4.20, 4.70, 6.96, 7.21-7.25, 7.33-7.41, 7.50-7.56.

Example 7(57)

4-[4-({4-[{[(4-fluorophenyl)amino]carbonyl}(phenyl)amino]-1-piperidinyl}methyl)-3,5-dimethyl-1H-pyrazol-1-yl]-N-[2-(4-morpholinyl)ethyl]benzenesulfonamide trihydrochloride

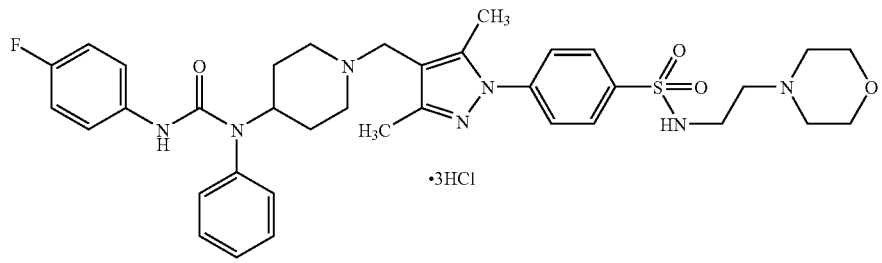

TLC: Rf 0.20 (chloroform:methanol=10:1);
NMR (CD₃OD): δ 1.70-1.85, 2.10-2.25, 2.34, 2.41, 3.20-3.40, 3.50-3.65, 3.80-3.95, 4.00-4.15, 4.21, 4.70, 6.96, 7.20-7.25, 7.35, 7.45-7.56, 7.75, 8.05.

Example 7(58)

N-{4-[(5-{4-((3,5-dimethyl-4-isoxazolyl){[(4-fluorophenyl)amino]carbonyl}amino)-1-piperidinyl]methyl}-2-pyridinyl)oxy]phenyl}methane sulfonamide hydrochloride (or dihydrochloride)

TLC: Rf 0.53 (dichloromethane:methanol=9:1);
NMR (CD₃OD): δ 1.68-1.88, 2.09-2.23, 2.20, 2.40, 2.97, 3.12-3.25, 3.50-3.60, 4.32, 4.60, 6.99, 7.09, 7.13, 7.25-7.35, 8.01, 8.25.

Example 7(59)

N-{4-[(5-{[4-(1,3-benzothiazol-6-yl{[(4-fluorophenyl)amino]carbonyl}amino)-1-piperidinyl]methyl}-2-pyridinyl)oxy]phenyl}methane sulfonamide dihydrochloride (or trihydrochloride)

TLC: Rf 0.49 (dichloromethane:methanol=9:1);

NMR (CD₃OD): δ 1.68-1.85, 2.19-2.28, 2.97, 3.12-3.25, 3.50-3.60, 4.30, 4.71, 6.94, 7.07, 7.13, 7.23, 7.32, 7.51, 8.00, 8.15, 8.20, 8.25, 9.46.

Example 7(60)

N-(4-{[5-({4-[{[(3,4-difluorophenyl)amino]carbonyl}(phenyl)amino]-1-piperidinyl}methyl)-2-pyridinyl]oxy}phenyl)methanesulfonamide hydrochloride (or dihydrochloride)

TLC: Rf 0.51 (dichloromethane:methanol=9:1);
NMR (CD₃OD): δ 1.64-1.81, 2.12-2.22, 2.97, 3.12-3.25, 3.48-3.58, 4.29, 4.68, 6.93, 7.02-7.15, 7.28-7.35, 7.38, 7.45-7.58, 7.95, 8.21.

Example 7(61)

N-(4-{[5-({4-[[(2,3-dihydro-1,4-benzodioxin-6-ylamino)carbonyl](phenyl)amino]-1-piperidinyl}methyl)-2-pyridinyl]oxy}phenyl)methanesulfonamide hydrochloride (or dihydrochloride)

TLC: Rf 0.51 (dichloromethane:methanol=9:1);
NMR (CD₃OD): δ 1.63-1.80, 2.12-2.22, 2.97, 3.11-3.25, 3.48-3.55, 4.17, 4.29, 4.68, 6.56, 6.66, 6.81, 7.07, 7.12, 7.27-7.35, 7.45-7.58, 7.96, 8.22.

Example 7(62)

N-(4-{[5-({4-[{[(2,4-difluorophenyl)amino]carbonyl}(3-thienyl)amino]-1-piperidinyl}methyl)-2-pyridinyl]oxy}phenyl)methanesulfonamide hydrochloride (or dihydrochloride)

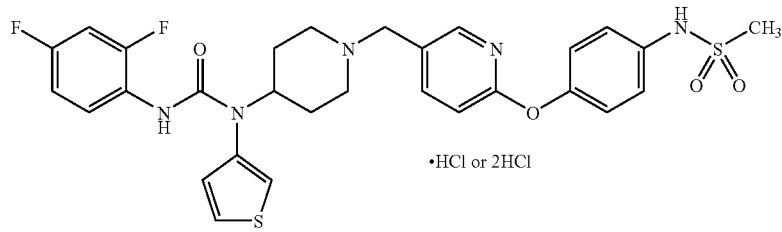

TLC: Rf 0.52 (dichloromethane:methanol=9:1);
NMR (CD$_3$OD): δ 1.63-1.80, 2.12-2.22, 2.97, 3.12-3.25, 3.48-3.58, 4.28, 4.68, 6.85-6.98, 7.03-7.08, 7.11, 7.31, 7.53-7.60, 7.64, 7.89, 8.18.

Example 7(63)

N-(4-{[5-({4-[{[(3,4-difluorophenyl)amino]carbonyl}(3-thienyl)amino]-1-piperidinyl}methyl)-2-pyridinyl]oxy}phenyl)methanesulfonamide hydrochloride (or dihydrochloride)

TLC: Rf 0.52 (dichloromethane:methanol=9:1);
NMR (CD$_3$OD): δ 1.62-1.80, 2.10-2.20, 2.97, 3.12-3.25, 3.48-3.58, 4.28, 4.68, 6.94-7.16, 7.31, 7.40, 7.51, 7.61, 7.90, 8.18.

Example 7(64)

N-(4-{[5-({4-[{[(4-fluorophenyl)amino]carbonyl}(2-methoxyphenyl)amino]-1-piperidinyl}methyl)-2-pyridinyl]oxy}phenyl)methanesulfonamide hydrochloride (or dihydrochloride)

TLC: Rf 0.52 (dichloromethane:methanol=9:1);
NMR (CD$_3$OD): δ 1.61-1.83, 2.15-2.25, 2.97, 3.10-3.22, 3.48-3.56, 3.84, 4.28, 4.58, 6.95, 7.05-7.29, 7.32, 7.46, 7.97, 8.23.

Example 7(65)

N-{4-[(5-{[4-((4-fluorophenyl){[(4-fluorophenyl)amino]carbonyl}amino)-1-piperidinyl]methyl}-2-pyridinyl)oxy]phenyl}methanesulfonamide hydrochloride (or dihydrochloride)

TLC: Rf 0.52 (dichloromethane:methanol=9:1);
NMR (CD$_3$OD): δ 1.60-1.78, 2.12-2.21, 2.97, 3.10-3.25, 3.48-3.58, 4.28, 4.65, 6.95, 7.05, 7.09, 7.19-7.37, 7.90, 8.17.

Example 7(66)

N-{4-[(5-{[4-((3-fluorophenyl){[(4-fluorophenyl)amino]carbonyl}amino)-1-piper

NMR (CD$_3$OD): δ 1.65-1.85, 2.12-2.25, 2.97, 3.12-3.25, 3.48-3.58, 4.28, 4.65, 6.95, 7.04-7.20, 7.22-7.33, 7.30, 7.53, 7.90, 8.17. idinyl]methyl}-2-pyridinyl)oxy]phenyl} methanesulfonamide hydrochloride (or dihydrochloride)
TLC: Rf 0.52 (dichloromethane:methanol=9:1);

Example 7(67)

N'-(4-chlorophenyl)-N-[1-({6-[4-(methylsulfonyl)phenoxy]-3-pyridinyl}methyl)-4-piperidinyl]-N-phenylurea hydrochloride (or dihydrochloride)

TLC: Rf 0.26 (ethyl acetate);
NMR (CD$_3$OD): δ 1.60-1.80, 2.10-2.30, 3.10-3.30, 3.14, 3.50-3.60, 4.30, 4.65, 7.17-7.23, 7.31-7.39, 7.52-7.55, 7.90-8.02, 8.21.

Example 7(68)

N'-(4-fluorophenyl)-N-[1-({6-[4-(methylsulfonyl)phenoxy]-3-pyridinyl}methyl)-4-piperidinyl]-N-(3-thienyl)urea hydrochloride (or dihydrochloride)

TLC: Rf 0.29 (chloroform:methanol=10:1);
NMR (CD$_3$OD): δ 1.60-1.80, 2.05-2.20, 3.14, 3.15-3.25, 3.50-3.60, 4.29, 4.65, 6.97, 7.04, 7.18-7.27, 7.38, 7.52, 7.61, 7.96-8.02, 8.23.

Example 7(69)

2-chloro-N-methyl-5-({[{1-[(6-{4-[(methylsulfonyl)amino]phenoxy}-3-pyridinyl)methyl]-4-piperidinyl}(phenyl)amino]carbonyl}amino)benzamide hydrochloride (or dihydrochloride)

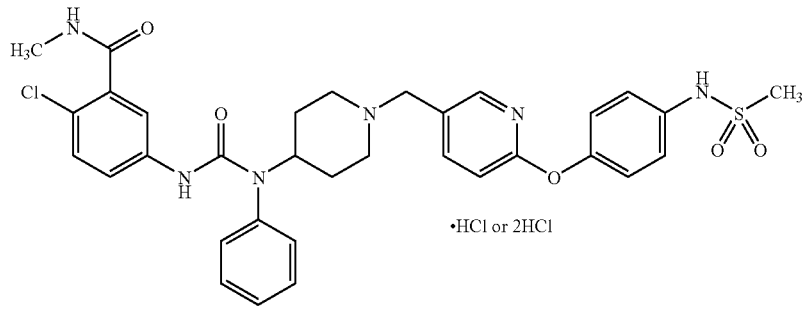

•HCl or 2HCl

TLC: Rf 0.50 (dichloromethane:methanol=9:1);
NMR (CD$_3$OD): δ 1.65-1.81, 2.12-2.22, 2.86, 2.97, 3.12-3.25, 3.49-3.58, 4.29, 4.67, 7.07, 7.13, 7.25-7.35, 7.43, 7.46-7.60, 7.96, 8.22.

Example 7(70)

2-chloro-N,N-dimethyl-5-({[{1-[(6-{4-[(methylsulfonyl)amino]phenoxy}-3-pyridinyl)methyl]-4-piperidinyl}(phenyl)amino]carbonyl}amino)benzamide hydrochloride (or dihydrochloride)

TLC: Rf 0.50 (dichloromethane:methanol=9:1);
NMR (CD$_3$OD): δ 1.65-1.81, 2.12-2.22, 2.86, 2.97, 3.08, 3.12-3.25, 3.49-3.58, 4.30, 4.67, 7.08, 7.14, 7.27-7.36, 7.48-7.60, 7.99, 8.25.

Example 7(71)

N-(4-{[5-({4-[{[(4-chloro-3-nitrophenyl)amino]carbonyl}(phenyl)amino]-1-piperidinyl}methyl)-2-pyridinyl]oxy}phenyl)methanesulfonamide TLC: Rf 0.39 (chloroform:methanol=7:1);

NMR (CDCl₃): δ 1.40-1.60, 1.80-1.90, 2.10-2.20, 2.80-2.90, 2.99, 3.46, 4.51, 4.64, 6.08, 6.84, 7.09, 7.21-7.27, 7.31-7.41, 7.51-7.54, 7.61, 7.89, 8.01.

Example 7(72)

N-(4-{[5-({4-[({[4-(methylsulfonyl)phenyl]amino}carbonyl)(phenyl)amino]-1-piperidinyl}methyl)-2-pyridinyl]oxy}phenyl)methanesulfonamide hydrochloride (or dihydrochloride)

TLC: Rf 0.52 (chloroform:methanol=10:1);
NMR (CD₃OD): δ 1.65-1.85, 2.10-2.30, 2.97, 3.05, 3.10-3.30, 3.50-3.60, 4.29, 4.70, 7.06, 7.11, 7.30-7.35, 7.32, 7.51-7.58, 7.77, 7.94, 8.20.

Example 7(73)

N-(4-{[5-({4-[({[3-(methylsulfonyl)phenyl]amino}carbonyl)(phenyl)amino]-1-piperidinyl}methyl)-2-pyridinyl]oxy}phenyl)methanesulfonamide hydrochloride (or dihydrochloride)

TLC: Rf 0.49 (chloroform:methanol=10:1);
NMR (CD₃OD): δ 1.65-1.85, 2.10-2.25, 2.98, 3.07, 3.10-3.30, 3.50-3.60, 4.31, 4.70, 7.08, 7.15, 7.31-7.36, 7.44-7.59, 8.02, 8.02, 8.26.

Example 7(74)

2-chloro-5-({[[1-(4-{4-[(methylsulfonyl)amino]phenoxy}benzyl)-4-piperidinyl](phenyl)amino]carbonyl}amino)benzamide hydrochloride TLC: Rf 0.43 (dichloromethane:methanol=9:1);
NMR (CD₃OD): δ 1.62-1.79, 2.12-2.22, 2.95, 3.10-3.22, 3.45-3.55, 4.22, 4.67, 7.01, 7.02, 7.25-7.34, 7.41, 7.46-7.58.

Example 7(75)

N-(4-{[5-({4-[({[4-chloro-3-(4-morpholinylcarbonyl)phenyl]amino}carbonyl)(phenyl)amino]-1-piperidinyl}methyl)-2-pyridinyl]oxy}phenyl)methanesulfonamide hydrochloride (or dihydrochloride)

TLC: Rf 0.43 (dichloromethane:methanol=9:1);
NMR (CD₃OD): δ 1.65-1.82, 2.12-2.22, 2.98, 3.14-3.35, 3.49-3.80, 4.31, 4.67, 7.08, 7.14, 7.28-7.37, 7.45-7.59, 8.02, 8.27.

Example 7(76)

2-chloro-5-({[{1-[(6-{4-[(methylsulfonyl)amino]phenoxy}-3-pyridinyl)methyl]-4-piperidinyl}(phenyl)amino]carbonyl}amino)benzoic acid hydrochloride (or dihydrochloride)

TLC: Rf 0.48 (dichloromethane:methanol=5:1);
NMR (CD₃OD): δ 1.64-1.82, 2.12-2.25, 2.97, 3.12-3.24, 3.47-3.60, 4.29, 4.67, 7.06, 7.11, 7.28-7.36, 7.41, 7.45-7.60, 7.82, 7.94, 8.20.

Example 7(77)

N'-(4-chloro-3-nitrophenyl)-N-[1-({6-[4-(methylsulfonyl)phenoxy]-3-pyridinyl}methyl)-4-piperidinyl]-N-phenylurea TLC: Rf 0.50 (ethyl acetate);
NMR (CDCl₃): δ 1.35-1.55, 1.80-1.90, 2.10-2.25, 2.90-3.00, 3.06, 3.44, 4.50, 6.04, 6.93, 7.20-7.39, 7.31-7.41, 7.50-7.53, 7.67, 7.92-8.05.

Example 7(78)

2-[4-({4-[{[(4-fluorophenyl)amino]carbonyl}(phenyl)amino]-1-piperidinyl}methyl)phenoxy]-5-[(methylsulfonyl)amino]benzamide hydrochloride TLC: Rf 0.53 (dichloromethane:methanol=9:1);
NMR (CD₃OD): δ 1.62-1.79, 2.12-2.21, 2.99, 3.08-3.22, 3.43-3.57, 4.23, 4.67, 6.95, 7.01, 7.06, 7.22, 7.29-7.35, 7.32-7.59, 7.70.

Example 7(79)

2-fluoro-5-({[[1-({6-[4-(methylsulfonyl)phenoxy]-3-pyridinyl}methyl)-4-piperidinyl](phenyl)amino]carbonyl}amino)benzamide hydrochloride (or dihydrochloride)

TLC: Rf 0.45 (dichloromethane:methanol=9:1);
NMR (CD₃OD): δ 1.64-1.81, 2.13-2.25, 3.14, 3.10-3.25, 3.50-3.58, 4.31, 4.67, 7.08, 7.19, 7.30-7.58, 7.69, 7.95-8.04, 8.23.

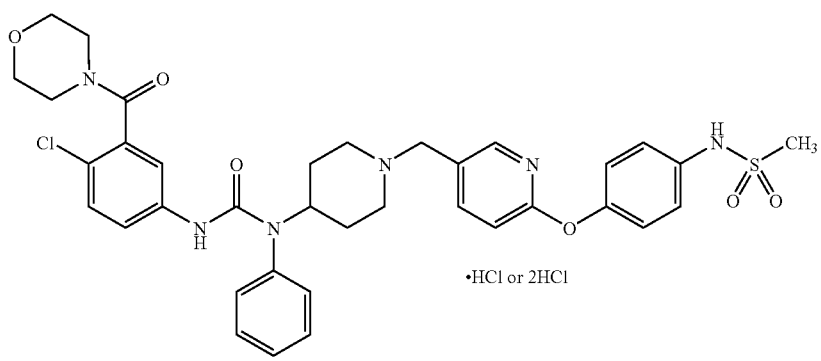

·HCl or 2HCl

Example 7(80)

2-fluoro-5-{[((3-fluorophenyl){1-[(6-{4-[(methylsulfonyl)amino]phenoxy}-3-pyridinyl)methyl]-4-piperidinyl}amino)carbonyl]amino}benzamide hydrochloride (or dihydrochloride)

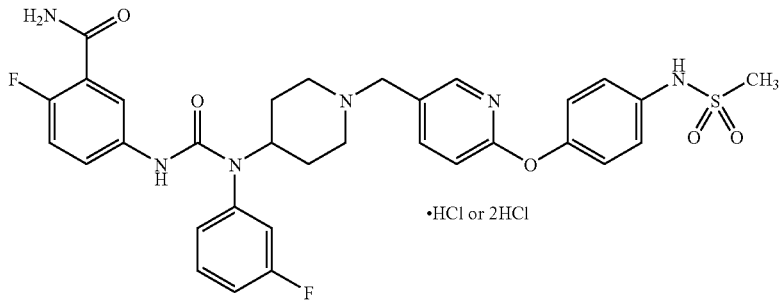

·HCl or 2HCl

TLC: Rf 0.49 (dichloromethane:methanol=9:1);
NMR (CD₃OD): δ 1.68-1.85, 2.14-2.23, 2.97, 3.12-3.25, 3.50-3.58, 4.30, 4.65, 7.04-7.19, 7.25, 7.31, 7.46, 7.51, 7.70, 7.92, 8.23.

Example 7(81)

2-fluoro-5-[({(3-fluorophenyl)[1-({6-[4-(methylsulfonyl)phenoxy]-3-pyridinyl}methyl)-4-piperidinyl]amino}carbonyl)amino]benzamide hydrochloride (or dihydrochloride)

TLC: Rf 0.52 (dichloromethane:methanol=9:1);
NMR (CD₃OD): δ 1.68-1.87, 2.15-2.25, 3.14, 3.12-3.25, 3.50-3.58, 4.31, 4.67, 7.09, 7.12-7.20, 7.25, 7.37, 7.46, 7.54, 7.71, 7.90-8.04, 8.23.

Example 7(82)

2-fluoro-5-[({(3-fluorophenyl)[1-({6-[2-methoxy-4-(methylsulfonyl)phenoxy]-3-pyridinyl}methyl)-4-piperidinyl]amino}carbonyl)amino]benzamide hydrochloride (or dihydrochloride)

TLC: Rf 0.52 (dichloromethane:methanol=9:1);
NMR (CD₃OD): δ 1.67-1.85, 2.15-2.25, 3.17, 3.12-3.25, 3.48-3.58, 3.80, 4.28, 4.65, 7.04-7.19, 7.25, 7.35, 7.46, 7.50-7.65, 7.71, 7.95, 8.13.

Example 7(83)

N-[2-fluoro-5-({[{1-[(6-{4-[(methylsulfonyl)amino]phenoxy}-3-pyridinyl)methyl]-4-piperidinyl}(phenyl)amino]carbonyl}amino)phenyl]acetamide hydrochloride (or dihydrochloride)

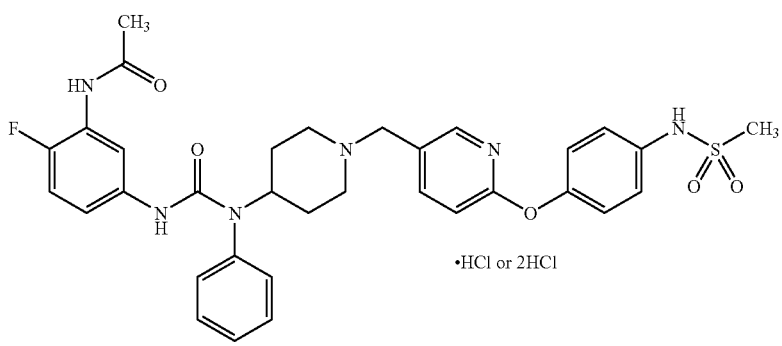

·HCl or 2HCl

White amorphous powder;
TLC: Rf 0.36 (chloroform:methanol=10:1);
NMR (CD₃OD): δ 1.60-1.80, 2.10-2.30, 2.12, 2.97, 3.10-3.25, 3.45-3.55, 4.27, 4.65, 7.00-7.12, 7.30-7.33, 7.49-7.55, 7.78, 7.90, 8.18.

Example 7(84)

N-[2-fluoro-5-({[{1-[(6-{2-methoxy-4-[(methylsulfonyl)amino]phenoxy}-3-pyridinyl)methyl]-4-piperidinyl}(phenyl)amino]carbonyl}amino)phenyl]acetamide hydrochloride (or dihydrochloride)

TLC: Rf 0.31 (chloroform:methanol 10:1);

NMR (CD₃OD): δ 1.60-1.80, 2.10-2.30, 2.12, 2.99, 3.10-3.25, 3.45-3.55, 3.69, 4.26, 4.65, 6.87, 6.98-7.08, 7.06, 7.31-7.34, 7.49-7.55, 7.78, 7.86, 8.11.

Example 7(85)

N-[2-fluoro-5-({[[1-({6-[4-(methylsulfonyl)phenoxy]-3-pyridinyl}methyl)-4-piperidinyl](phenyl)amino]carbonyl}amino)phenyl]acetamide hydrochloride (or dihydrochloride)

TLC: Rf 0.53 (chloroform:methanol=10:1);
NMR (CD₃OD): δ 1.60-1.80, 2.10-2.30, 2.12, 3.10-3.25, 3.14, 3.45-3.55, 4.30, 4.65, 7.00-7.05, 7.19, 7.31-7.39, 7.50-7.55, 7.90, 7.94-8.02, 8.11.

Example 7(86)

N-[2-fluoro-5-({[[1-({6-[2-methoxy-4-(methylsulfonyl)phenoxy]-3-pyridinyl}methyl)-4-piperidinyl](phenyl)amino]carbonyl}amino)phenyl]acetamide hydrochloride (or dihydrochloride)

TLC: Rf 0.52 (chloroform:methanol=10:1);
NMR (CD$_3$OD): δ 1.60-1.80, 2.10-2.30, 2.12, 3.10-3.25, 3.17, 3.45-3.55, 3.79, 4.26, 4.66, 7.00-7.11, 7.19, 7.31-7.36, 7.49-7.63, 7.78, 7.78, 8.11.

Example 7(87)

2-fluoro-5-{[((3-fluorophenyl){1-[(6-{2-methoxy-4-[(methylsulfonyl)amino]phenoxy}-3-pyridinyl)methyl]-4-piperidinyl}amino)carbonyl]amino}benzamide hydrochloride (or dihydrochloride)

TLC: Rf 0.44 (dichloromethane:methanol=9:1);
NMR (CD$_3$OD): δ 1.69-1.85, 2.12-2.25, 3.00, 3.12-3.25, 3.48-3.58, 3.70, 4.28, 4.65, 6.87, 6.99-7.19, 7.25, 7.46, 7.54, 7.71, 7.93, 8.17.

Example 7(88)

2-fluoro-5-({[{1-[(6-{2-methoxy-4-[(methylsulfonyl)amino]phenoxy}-3-pyridinyl)methyl]-4-piperidinyl}(phenyl)amino]carbonyl}amino)benzamide hydrochloride (or dihydrochloride)

TLC: Rf 0.44 (dichloromethane:methanol=9:1);
NMR (CD$_3$OD): δ 1.64-1.81, 2.12-2.24, 3.00, 3.12-3.25, 3.48-3.58, 3.70, 4.28, 4.67, 6.87, 7.00-7.12, 7.29-7.35, 7.42, 7.47-7.58, 7.68, 7.94, 8.18.

Example 7(89)

2-fluoro-5-({[[1-({6-[2-methoxy-4-(methylsulfonyl)phenoxy]-3-pyridinyl}methyl)-4-piperidinyl](phenyl)amino]carbonyl}amino)benzamide hydrochloride (or dihydrochloride)

TLC: Rf 0.44 (dichloromethane:methanol=9:1);
NMR (CD$_3$OD): δ 1.64-1.80, 2.12-2.22, 3.17, 3.12-3.25, 3.48-3.58, 3.79, 4.28, 4.67, 7.04-7.14, 7.29-7.38, 7.43, 7.48-7.64, 7.68, 7.94, 8.13.

Example 7(90)

N-{4-[(5-{[4-((3-fluorophenyl){[(6-methyl-3-pyridinyl)amino]carbonyl}amino)-1-piperidinyl]methyl}-2-pyridinyl)oxy]phenyl}methanesulfonamide dihydrochloride (or trihydrochloride)

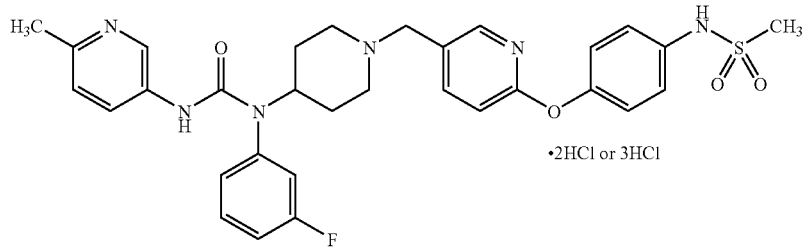

White amorphous powder;
TLC: Rf 0.49 (dichloromethane:methanol=9:1);
NMR (CD$_3$OD): δ 1.70-1.90, 2.12-2.25, 2.68, 2.97, 3.12-3.35, 3.48-3.60, 4.33, 4.70, 7.08, 7.12-7.23, 7.25-7.35, 7.55, 7.73, 8.05, 8.23-8.34, 8.96.

Example 7(91)

N-(3-fluorophenyl)-N'-(6-methyl-3-pyridinyl)-N-[1-({6-[4-(methylsulfonyl)phenoxy]-3-pyridinyl}methyl)-4-piperidinyl]urea dihydrochloride (or trihydrochloride)

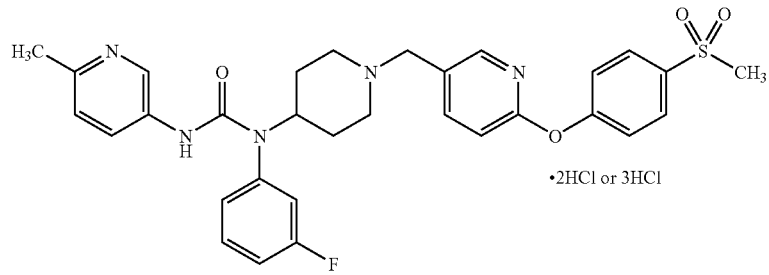

TLC: Rf 0.50 (dichloromethane:methanol=9:1);
NMR (CD$_3$OD): δ 1.70-1.90, 2.12-2.25, 2.68, 3.14, 3.12-3.35, 3.48-3.60, 4.33, 4.70, 7.12-7.21, 7.29, 7.38, 7.56, 7.73, 8.00, 8.03, 8.22-8.36, 8.96.

Example 7(92)

N-(3-fluorophenyl)-N-[1-({6-[2-methoxy-4-(methylsulfonyl)phenoxy]-3-pyridinyl}methyl)-4-piperidinyl]-N'-(6-methyl-3-pyridinyl)urea dihydrochloride (or trihydrochloride)

TLC: Rf 0.50 (dichloromethane:methanol=9:1);
NMR (CD$_3$OD): δ 1.70-1.90, 2.12-2.25, 2.68, 3.17, 3.12-3.35, 3.48-3.60, 3.80, 4.30, 4.70, 7.12, 7.15-7.23, 7.29, 7.35, 7.51-7.64, 7.73, 7.99, 8.15, 8.31, 8.96.

Example 7(93)

N-[2-fluoro-5-({[{1-[(6-{4-[(methylsulfonyl)amino]phenoxy}-3-pyridinyl)methyl]-4-piperidinyl}(phenyl)amino]carbonyl}amino)phenyl]methanesulfonamide hydrochloride (or dihydrochloride)

TLC: Rf 0.33 (ethyl acetate:methanol=10:1);
NMR (CD$_3$OD): δ 1.60-1.80, 2.10-2.30, 2.97, 2.97, 3.10-3.25, 3.40-3.60, 4.27, 4.65, 7.03-7.11, 7.29-7.33, 7.44-7.54, 7.87, 8.16.

Example 7(94)

N-[2-fluoro-5-({[[1-({6-[4-(methylsulfonyl)phenoxy]-3-pyridinyl}methyl)-4-piperidinyl](phenyl)amino]carbonyl}amino)phenyl]methanesulfonamide hydrochloride (or dihydrochloride)

TLC: Rf 0.41 (ethyl acetate:methanol=10:1);
NMR (CD$_3$OD): δ 1.60-1.80, 2.10-2.30, 2.97, 3.14, 3.15-3.25, 3.45-3.55, 4.30, 4.62, 7.03-7.06, 7.18, 7.31-7.39, 7.44-7.54, 7.95-8.02, 8.22.

Example 7(95)

N-[2-fluoro-5-({[[1-({6-[2-methoxy-4-(methylsulfonyl)phenoxy]-3-pyridinyl}methyl)-4-piperidinyl](phenyl)amino]carbonyl}amino)phenyl]methanesulfonamide hydrochloride (or dihydrochloride)

TLC: Rf 0.39 (ethyl acetate:methanol=10:1);
NMR (CD$_3$OD): δ 1.60-1.80, 2.10-2.25, 2.97, 3.10-3.25, 3.17, 3.45-3.55, 3.79, 4.26, 4.65, 7.03-7.06, 7.12, 7.31-7.36, 7.45-7.63, 7.91, 8.10.

Example 7(96)

2-[4-({4-[[({4-fluoro-3-[(methylsulfonyl)amino]phenyl}amino)carbonyl](phenyl)amino]-1-piperidinyl}methyl)phenoxy]-5-[(methylsulfonyl)amino]benzamide hydrochloride

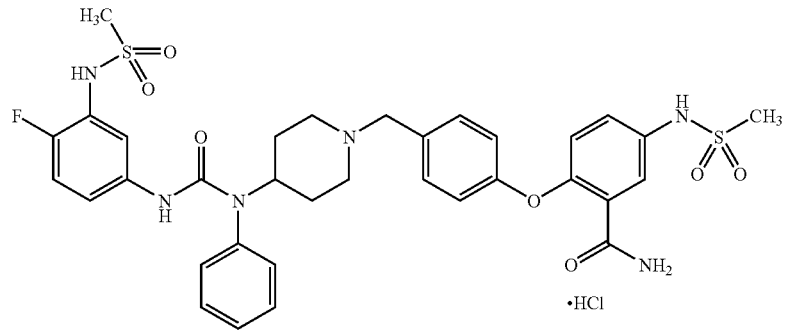

TLC: Rf 0.20 (ethyl acetate:methanol=10:1);
NMR (CD$_3$OD): δ 1.60-1.80, 2.10-2.30, 2.97, 2.99, 3.10-3.20, 3.45-3.55, 4.23, 4.65, 6.99-7.04, 7.31-7.55, 7.69.

Example 7(97)

2-fluoro-N-methyl-5-({[{1-[(6-{4-[(methylsulfonyl)amino]phenoxy}-3-pyridinyl)methyl]-4-piperidinyl}(phenyl)amino]carbonyl}amino)benzamide hydrochloride (or dihydrochloride)

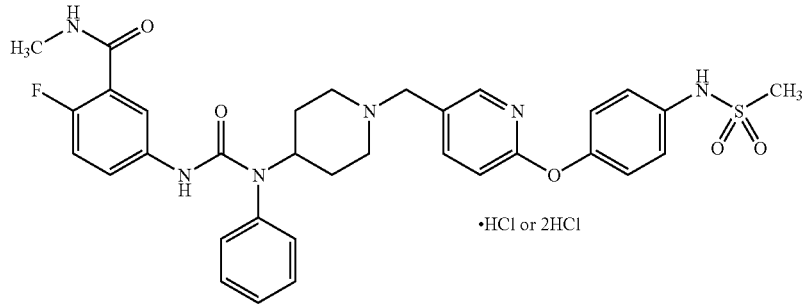

TLC: Rf 0.50 (dichloromethane:methanol=9:1);
NMR (CD$_3$OD): δ 1.65-1.81, 2.12-2.23, 2.89, 2.97, 3.12-3.25, 3.48-3.58, 4.29, 4.67, 7.01-7.15, 7.27-7.35, 7.40, 7.47-7.57, 7.61, 7.95, 8.21.

Example 7(98)

2-fluoro-N-methyl-5-({[[1-({6-[4-(methylsulfonyl)phenoxy]-3-pyridinyl}methyl)-4-piperidinyl](phenyl)amino]carbonyl}amino)benzamide hydrochloride (or dihydrochloride)

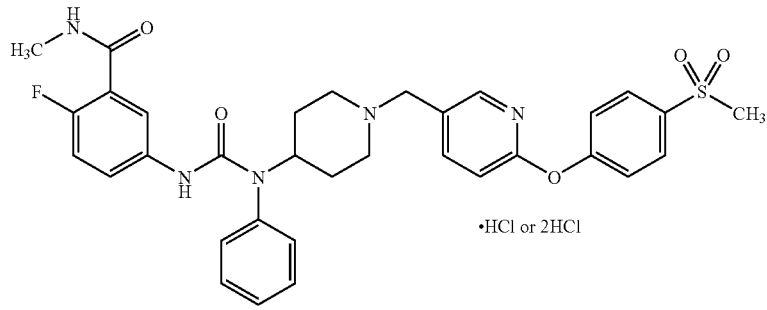

TLC: Rf 0.50 (dichloromethane:methanol=9:1);
NMR (CD$_3$OD): δ 1.65-1.81, 2.12-2.23, 2.89, 3.14, 3.12-3.25, 3.48-3.59, 4.30, 4.67, 7.06, 7.18, 7.30-7.43, 7.47-7.57, 7.61, 7.94-8.05, 8.22.

Example 7(99)

N'-(6-methyl-3-pyridinyl)-N-[1-({6-[4-(methylsulfonyl)phenoxy]-3-pyridinyl}methyl)-4-piperidinyl]-N-phenylurea dihydrochloride (or trihydrochloride)

TLC: Rf 0.49 (dichloromethane:methanol=9:1);
NMR (CD$_3$OD): δ 1.70-1.87, 2.12-2.24, 2.68, 3.14, 3.17-3.35, 3.50-3.60, 4.33, 4.71, 7.18, 7.32-7.36, 7.38, 7.42-7.59, 7.72, 8.00, 8.05, 8.27, 8.30, 8.96.

Example 7(100)

2-[4-[({4-[({[3-(acetylamino)-4-fluorophenyl]amino}carbonyl)(phenyl)amino]-1-piperidinyl}methyl)phenoxy]-5-[(methylsulfonyl)amino]benzamide hydrochloride

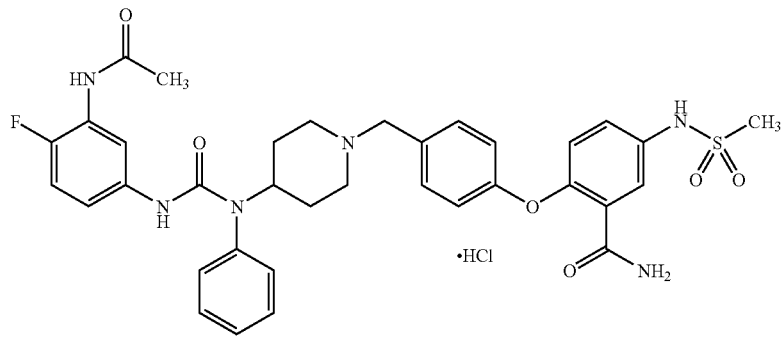

TLC: Rf 0.43 (dichloromethane:methanol=9:1);
NMR (CD$_3$OD): δ 1.61-1.80, 2.12, 2.05-2.22, 2.99, 3.05-3.21, 3.45-3.55, 4.23, 4.67, 6.97-7.08, 7.28-7.35, 7.35-7.58, 7.69, 7.77.

Example 7(101)

N-(3-methyl-4-{[5-({4-[{[(6-methyl-3-pyridinyl)amino]carbonyl}(phenyl)amino]-1-piperidinyl}methyl)-2-pyridinyl]oxy}phenyl)methanesulfonamide dihydrochloride (or trihydrochloride)

TLC: Rf 0.48 (dichloromethane:methanol=9:1);
NMR (CD$_3$OD): δ 1.68-1.85, 2.11, 2.12-2.23, 2.67, 2.97, 3.12-3.28, 3.50-3.60, 4.30, 4.71, 7.02, 7.04, 7.15, 7.20, 7.31-7.38, 7.49-7.60, 7.73, 8.00, 8.17, 8.22, 8.31, 8.96.

Example 7(102)

N-(3-chloro-4-{[5-({4-[{[(6-methyl-3-pyridinyl)amino]carbonyl}(phenyl)amino]-1-piperidinyl}methyl)-2-pyridinyl]oxy}phenyl)methanesulfonamide dihydrochloride (or trihydrochloride)

TLC: Rf 0.48 (dichloromethane:methanol=9:1);
NMR (CD$_3$OD): δ 1.65-1.85, 2.12-2.25, 2.67, 3.01, 3.15-3.28, 3.48-3.58, 4.30, 4.72, 7.12, 7.19-7.28, 7.31-7.37, 7.41, 7.48-7.60, 7.74, 7.98, 8.17, 8.30, 8.97.

Example 7(103)

N-(4-{[5-({4-[{[(6-methyl-3-pyridinyl)amino]carbonyl}(phenyl)amino]-1-piperidinyl}methyl)-2-pyridinyl]oxy}phenyl)ethanesulfonamide dihydrochloride (or trihydrochloride)

TLC: Rf 0.48 (dichloromethane:methanol=9:1);
NMR (CD$_3$OD): δ 1.32, 1.70-1.85, 2.15-2.25, 2.68, 3.11, 3.15-3.28, 3.50-3.60, 4.33, 4.71, 7.08, 7.14, 7.30-7.38, 7.50-7.60, 7.73, 8.07, 8.28-8.35, 8.96.

Example 7(104)

N-{4-[(5-{[4-((3-methylphenyl){[(6-methyl-3-pyridinyl)amino]carbonyl}amino)-1-piperidinyl]methyl}-2-pyridinyl)oxy]phenyl}methanesulfonamide dihydrochloride (or trihydrochloride)

TLC: Rf 0.48 (dichloromethane:methanol=9:1);
NMR (CD$_3$OD): δ 1.68-1.87, 2.12-2.23, 2.41, 2.68, 2.97, 3.13-3.28, 3.50-3.60, 4.31, 4.71, 7.05-7.18, 7.29-7.37, 7.43, 7.73, 8.01, 8.13, 8.26, 8.31, 8.96.

Example 7(105)

2-fluoro-5-{[((3-methylphenyl){1-[(6-{4-[(methylsulfonyl)amino]phenoxy}-3-pyridinyl)methyl]-4-piperidinyl}amino)carbonyl]amino}benzamide hydrochloride (or dihydrochloride)

TLC: Rf 0.46 (dichloromethane:methanol=9:1);
NMR (CD$_3$OD): δ 1.65-1.81, 2.12-2.24, 2.40, 2.97, 3.13-3.28, 3.48-3.58, 4.29, 4.67, 7.04-7.17, 7.28-7.35, 7.37-7.47, 7.68, 7.95, 8.21.

Example 7(106)

2-fluoro-N-methyl-5-{[((3-methylphenyl){1-[(6-{4-[(methylsulfonyl)amino]phenoxy}-3-pyridinyl)methyl]-4-piperidinyl}amino)carbonyl]amino}benzamide hydrochloride (or dihydrochloride)

TLC: Rf 0.49 (dichloromethane:methanol=9:1);
NMR (CD$_3$OD): δ 1.65-1.81, 2.12-2.22, 2.40, 2.89, 2.97, 3.12-3.26, 3.48-3.58, 4.30, 4.67, 7.02-7.18, 7.28-7.35, 7.36-7.44, 7.61, 7.99, 8.25.

Example 7(107)

N-(2-fluoro-5-{[((3-methylphenyl){1-[(6-{4-[(methylsulfonyl)amino]phenoxy}-3-pyridinyl)methyl]-4-piperidinyl}amino)carbonyl]amino}phenyl)acetamide hydrochloride (or dihydrochloride)

TLC: Rf 0.45 (ethyl acetate:methanol=10:1);
NMR (CD$_3$OD): δ 1.60-1.80, 2.10-2.25, 2.12, 2.40, 2.97, 3.10-3.30, 3.50-3.60, 4.27, 4.65, 7.00-7.15, 7.30, 7.31, 7.42, 7.78, 7.90, 8.17.

Example 7(108)

N-(2-fluoro-5-{[((3-fluorophenyl){1-[(6-{4-[(methylsulfonyl)amino]phenoxy}-3-pyridinyl)methyl]-4-piperidinyl}amino)carbonyl]amino}phenyl)acetamide hydrochloride (or dihydrochloride)

TLC: Rf 0.46 (ethyl acetate:methanol=10:1);
NMR (CD$_3$OD): δ 1.60-1.80, 2.10-2.25, 2.13, 2.97, 3.10-3.30, 3.50-3.60, 4.28, 4.65, 6.98-7.17, 7.29, 7.31, 7.54, 7.82, 7.94, 8.20.

Example 7(109)

N-(4-{[5-({4-[{[(6-methyl-3-pyridinyl)amino]carbonyl}(phenyl)amino]-1-piperidinyl}methyl)-2-pyrazinyl]oxy}phenyl)methanesulfonamide trihydrochloride TLC: Rf 0.49 (dichloromethane:methanol=9:1);
NMR (CD$_3$OD): δ 1.71-1.88, 2.15-2.26, 2.68, 2.97, 3.22-3.35, 3.58-3.68, 4.42, 4.75, 7.17, 7.29-7.38, 7.52-7.62, 7.73, 8.17, 8.20, 8.31, 8.48, 8.97.

Example 7(110)

2-fluoro-5-{[((3-fluorophenyl){1-[(6-{4-[(methylsulfonyl)amino]phenoxy}-3-pyridinyl)methyl]-4-piperidinyl}amino)carbonyl]amino}-N-methylbenzamide hydrochloride (or dihydrochloride)

TLC: Rf 0.45 (dichloromethane:methanol=9:1);
NMR (CD$_3$OD): δ 1.70-1.85, 2.15-2.23, 2.89, 2.97, 3.12-3.25, 3.50-3.58, 4.30, 4.65, 7.03-7.19, 7.25, 7.32, 7.42, 7.54, 7.65, 7.99, 8.25.

Example 7(111)

N-(4-{[5-({4-[{[(6-methyl-3-pyridinyl)amino]carbonyl}(phenyl)amino]-1-azepanyl}methyl)-2-pyridinyl]oxy}phenyl)methanesulfonamide dihydrochloride (or trihydrochloride)

TLC: Rf 0.42 (dichloromethane:methanol=9:1);
NMR (CD$_3$OD): δ 1.70-2.50, 2.67, 2.98, 3.18-3.35, 3.40-3.62, 4.37, 4.50, 7.10, 7.16, 7.30-7.40, 7.48-7.60, 7.72, 8.12, 8.29, 8.33, 8.96.

Example 7(112)

N-(4-{[5-({(3R)-3-[{[(6-methyl-3-pyridinyl)amino]carbonyl}(phenyl)amino]-1-pyrrolidinyl}methyl)-2-pyridinyl]oxy}phenyl)methanesulfonamide dihydrochloride (or trihydrochloride)

TLC: Rf 0.48 (dichloromethane:methanol=9:1);
NMR (CD$_3$OD): δ 2.40, 2.65, 2.69, 2.98, 3.41-3.65, 3.80-3.98, 4.30-4.72, 7.08-7.20, 7.28-7.62, 7.74, 8.14, 8.32, 8.39, 8.51, 8.97.

Example 7(113)

N-(4-{[5-({(3S)-3-[{[(6-methyl-3-pyridinyl)amino]carbonyl}(phenyl)amino]-1-pyrrolidinyl}methyl)-2-pyridinyl]oxy}phenyl)methanesulfonamide dihydrochloride (or trihydrochloride)

TLC: Rf 0.48 (dichloromethane:methanol=9:1);
NMR (CD$_3$OD): δ 2.40, 2.65, 2.69, 2.98, 3.41-3.65, 3.80-3.98, 4.30-4.72, 7.08-7.20, 7.28-7.62, 7.74, 8.14, 8.32, 8.39, 8.51, 8.97.

Example 7(114)

N-(2-fluoro-5-{[((3-fluorophenyl){1-[(6-{2-methyl-4-[(methylsulfonyl)amino]phenoxy}-3-pyridinyl)methyl]-4-piperidinyl}amino)carbonyl]amino}phenyl)acetamide hydrochloride (or dihydrochloride)

TLC: Rf 0.29 (ethyl acetate:methanol=10:1);

NMR (CD$_3$OD): δ 1.65-1.90, 2.00-2.20, 2.11, 2.12, 2.97, 3.10-3.30, 3.50-3.60, 4.27, 4.63, 6.98-7.06, 7.13-7.27, 7.53, 7.81, 7.94, 8.17.

Example 7(115)

N-[5-({[{1-[(6-{4-[(ethylsulfonyl)amino]phenoxy}-3-pyridinyl)methyl]-4-piperidinyl}(3-fluorophenyl)amino]carbonyl}amino)-2-fluorophenyl]acetamide hydrochloride (or dihydrochloride)

TLC: Rf 0.24 (ethyl acetate:methanol=10:1);
NMR (CD$_3$OD): δ 1.32, 1.60-1.80, 2.10-2.30, 2.12, 3.08, 3.10-3.25, 3.50-3.60, 4.29, 4.70, 7.00-7.16, 7.25, 7.31, 7.54, 7.81, 7.95, 8.22.

Example 7(116)

2-fluoro-5-({[{1-[(6-{2-methyl-4-[(methylsulfonyl)amino]phenoxy}-3-pyridinyl)methyl]-4-piperidinyl}(phenyl)amino]carbonyl}amino)benzamide hydrochloride (or dihydrochloride)

TLC: Rf 0.48 (dichloromethane:methanol=9:1);
NMR (CD$_3$OD): δ 1.68-1.82, 2.12, 2.09-2.22, 2.98, 3.12-3.25, 3.48-3.59, 4.31, 4.68, 7.01-7.23, 7.30-7.37, 7.43, 7.47-7.58, 7.68, 8.03, 8.27.

Example 7(117)

5-({[{1-[(6-{4-[(ethylsulfonyl)amino]phenoxy}-3-pyridinyl)methyl]-4-piperidinyl}(phenyl)amino]carbonyl}amino)-2-fluorobenzamide hydrochloride (or dihydrochloride)

TLC: Rf 0.48 (dichloromethane:methanol=9:1);
NMR (CD$_3$OD): δ 1.32, 1.65-1.82, 2.12-2.22, 3.10, 3.10-3.25, 3.49-3.58, 4.31, 4.68, 7.05-7.10, 7.13, 7.29-7.36, 7.43, 7.47-7.58, 7.68, 8.02, 8.28.

Example 7(118)

N-{4-[(5-{[4-((3-fluorophenyl){[(6-methyl-3-pyridinyl)amino]carbonyl}amino)-1-piperidinyl]methyl}-2-pyridinyl)oxy]phenyl}ethanesulfonamide dihydrochloride (or trihydrochloride)

TLC: Rf 0.46 (dichloromethane:methanol=9:1);

Example 7(119)

2-{[5-({4-[{[(6-methyl-3-pyridinyl)amino]carbonyl}(phenyl)amino]-1-piperidinyl}methyl)-2-pyridinyl]oxy}-5-[(methylsulfonyl)amino]benzamide dihydrochloride (or trihydrochloride)

TLC: Rf 0.69 (chloroform:methanol=5:1);
NMR (CD$_3$OD): δ 1.70-1.90, 2.10-2.30, 2.68, 2.93, 3.20-3.40, 3.50-3.60, 4.41, 4.70, 7.04, 7.33-7.43, 7.50-7.60, 7.73, 7.96, 8.17, 8.27, 8.30, 8.54, 8.96.

Example 7(120)

2-[(5-{[4-((3-fluorophenyl){[(6-methyl-3-pyridinyl)amino]carbonyl}amino)-1-piperidinyl]methyl}-2-pyridinyl)oxy]-5-[(methylsulfonyl)amino]benzamide dihydrochloride (or trihydrochloride)

TLC: Rf 0.59 (chloroform:methanol=5:1);
NMR (CD$_3$OD): δ 1.70-1.90, 2.10-2.30, 2.68, 2.93, 3.20-3.40, 3.50-3.70, 4.41, 4.70, 7.03, 7.15-7.20, 7.30, 7.41, 7.56, 7.74, 7.96, 8.25-8.35, 8.39, 8.54, 8.97.

Example 7(121)

2-{[5-({4-[({[3-(acetylamino)-4-fluorophenyl]amino}carbonyl)(3-fluorophenyl)amino]-1-piperidinyl}methyl)-2-pyridinyl]oxy}-5-[(methylsulfonyl)amino]benzamide hydrochloride (or dihydrochloride)

TLC: Rf 0.56 (chloroform:methanol=5:1);
NMR (CD$_3$OD): δ 1.70-1.90, 2.10-2.30, 2.12, 2.93, 3.20-3.40, 3.50-3.70, 4.37, 4.65, 6.99-7.10, 7.03, 7.15-7.20, 7.25, 7.40, 7.54, 7.82, 7.96, 8.15, 8.28, 8.49.

Example 8

4-{[5-({4-[{[(4-fluorophenyl)amino]carbonyl}(phenyl)amino]-1-piperidinyl}methyl)-2-pyridinyl]oxy}-N-(2-methoxyethyl)benzamide hydrochloride (or dihydrochloride)

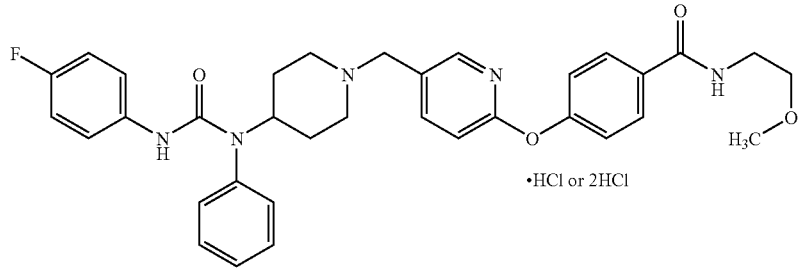

•HCl or 2HCl

NMR (CD$_3$OD): δ 1.32, 1.72-1.90, 2.12-2.25, 2.68, 3.11, 3.18-3.30, 3.50-3.60, 4.34, 4.70, 7.07-7.23, 7.29, 7.33, 7.56, 7.74, 8.10, 8.29-8.38, 8.97.

To a solution of the compound prepared in Example 7(50) (80 mg) in N,N-dimethylformamide (3 ml) was added O-(7-azabenzotriazol-1-yl)-N,N,N',N'-tetramethyluronium hexafluorophosphate (84 mg), diisopropylethylamine (38 μl) and 1-methoxyethylamine (19 μl), and stirred overnight. To the reaction mixture was added a saturated aqueous solution of sodium hydrogen carbonate, extracted with ethyl acetate. The organic layer was dried over anhydrous sodium sulfate, concentrated. The obtained residue was treated with 4N hydrogen chloride in ethyl acetate solution to give the title compound (65 mg) having the following physical data.

TLC: Rf 0.49 (chloroform:methanol=10:1);

NMR (CD$_3$OD): δ 1.65-1.80, 2.10-2.25, 3.10-3.30, 3.30-3.40, 3.50-3.60, 3.56, 4.29, 4.70, 6.92-6.98, 7.11, 7.19-7.24, 7.31-7.34, 7.52-7.55, 7.89, 7.90, 8.20.

Example 8(1)

N'-(4-fluorophenyl)-N-[1-({6-[4-(4-morpholinylcarbonyl)phenoxy]-3-pyridinyl}methyl)-4-piperidinyl]-N-phenylurea hydrochloride (or dihydrochloride)

By the same procedure as described in Example 8 using morpholine instead of 1-methoxyethylamine the following the title compound having the following physical data was obtained.

TLC: Rf 0.51 (chloroform:methanol 10:1);

NMR (CD$_3$OD): δ 1.65-1.80, 2.10-2.25, 3.10-3.25, 3.40-3.55, 3.55-3.80, 4.26, 4.65, 6.92-6.95, 7.11, 7.19-7.23, 7.32-7.34, 7.49-7.55, 7.94, 8.18.

Example 9

N-(4-{[5-({4-[{[(3-amino-4-chlorophenyl)amino]carbonyl}(phenyl)amino]-1-piperidinyl}methyl)-2-pyridinyl]oxy}phenyl)methanesulfonamide dihydrochloride (or trihydrochloride)

To a solution of the compound prepared in Example 7(71) (720 mg) in acetic acid (10 ml) and water (10 ml) was added iron powder (244 mg), and the mixture was stirred for 2 hours at 40° C. The reaction mixture was filtrated through Celite (registered trademark). After the filtrate was neutralized with 1N aqueous solution of sodium hydroxide, it was extracted with ethyl acetate. The organic layer was washed with water and brine, dried over anhydrous sodium sulfate, and concentrated. The obtained residue was purified by column chromatography on silica gel (dichloromethane:methanol=20:1). To this free form treated with 4N hydrogen chloride in ethyl acetate solution to give the title compound (420 mg) having the following physical data.

TLC: Rf 0.48 (chloroform:methanol=10:1);

NMR (CD$_3$OD): δ 1.65-1.80, 2.10-2.30, 2.97, 3.10-3.25, 3.50-3.60, 4.28, 4.70, 7.05, 7.10, 7.15, 7.29-7.32, 7.30, 7.37, 7.50-7.55, 7.72, 7.90, 8.17.

Example 10

N-[2-chloro-5-({[{1-[(6-{4-[(methylsulfonyl)amino]phenoxy}-3-pyridinyl)methyl]-4-piperidinyl}(phenyl)amino]carbonyl}amino)phenyl]methanesulfonamide hydrochloride (or dihydrochloride)

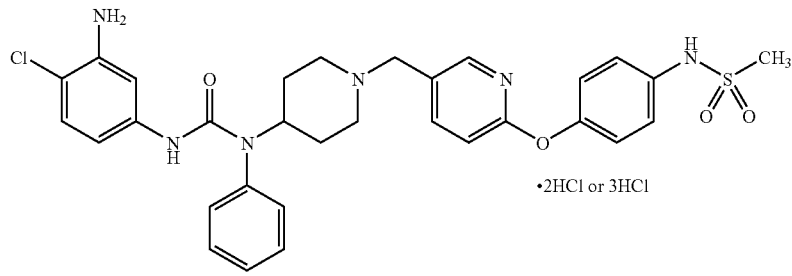

•2HCl or 3HCl

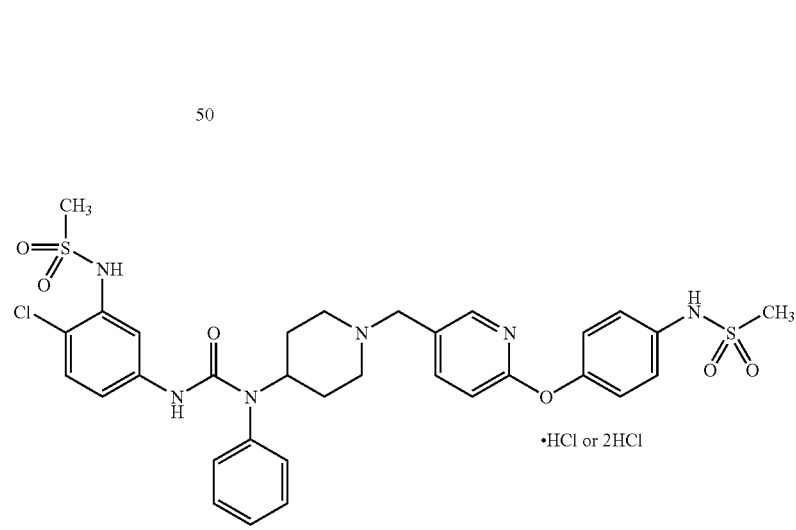

•HCl or 2HCl

To mixture of the free form compound prepared in Example 9 (160 mg) and triethylamine (36 µl) in tetrahydrofuran (5 ml) was added methanesulfonyl chloride (20 µl), and the mixture was stirred overnight at room temperature. The reaction mixture was extracted with ethyl acetate, dried over anhydrous sodium sulfate, and concentrated. The obtained residue was dissolved in tetrahydrofuran (10 ml), and to this solution was added tetrabutylammonium fluoride (146 µl). The mixture was stirred for 3 hours at 60° C. To the mixture was added water, extracted with ethyl acetate. The organic layer was washed with water and brine, dried over anhydrous sodium sulfate, and concentrated. The obtained residue was purified by column chromatography on silica gel (dichloromethane:methanol=20:1). The obtained compound was treated with 4N hydrogen chloride in ethyl acetate solution to give the title compound (35 mg) having the following physical data.

TLC: Rf 0.48 (chloroform:methanol=10:1);

NMR (CD$_3$OD): δ 1.65-1.80, 2.10-2.25, 2.97, 2.97, 3.10-3.25, 3.50-3.60, 4.29, 4.70, 7.06, 7.10-7.15, 7.28-7.34, 7.52-7.58, 7.94, 8.21.

Example 11

N-[2-chloro-5-({[{1-[(6-{4-[(methylsulfonyl)amino]phenoxy}-3-pyridinyl)methyl]-4-piperidinyl}(phenyl)amino]carbonyl}amino)phenyl]acetamide hydrochloride (or dihydrochloride)

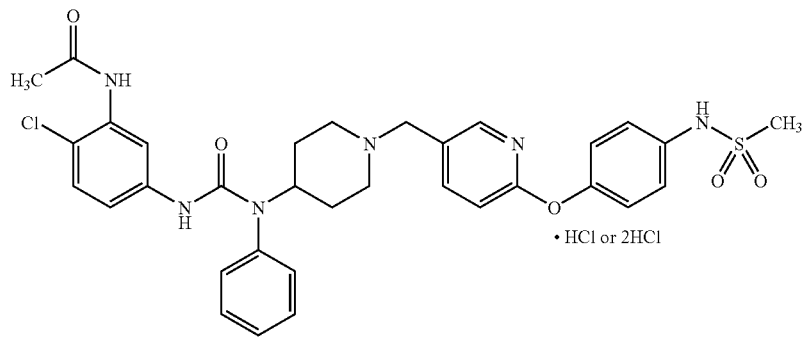

• HCl or 2HCl

To a solution of the free form compound prepared in Example 9 (160 mg) in pyridine (4 ml) was added acetic acid anhydride (72.4 µl), and the mixture was stirred overnight at room temperature. The reaction mixture was extracted with ethyl acetate, dried over anhydrous sodium sulfate, and concentrated. To a solution of the obtained residue in methanol (4 ml) was added 28% sodium methoxide in methanol solution (506 µl), stirred for 30 minutes at room temperature. The reaction mixture was concentrated, added water, and extracted with ethyl acetate. The organic layer was washed with water and brine, dried over anhydrous sodium sulfate, and concentrated. The obtained residue was treated with 4N hydrogen chloride in ethyl acetate solution to give the title compound (64 mg) having the following physical data.

TLC: Rf 0.40 (chloroform:methanol=10:1);

NMR (CD$_3$OD): δ 1.65-1.80, 2.13, 2.15-2.25, 2.97, 3.10-3.35, 3.50-3.60, 4.30, 4.65, 7.07, 7.12-7.16, 7.25-7.34, 7.49-7.51, 7.68, 7.99, 8.25.

Example 12

N-[2-chloro-5-({[[1-({6-[4-(methylsulfonyl)phenoxy]-3-pyridinyl}methyl)-4-piperidinyl](phenyl)amino]carbonyl}amino)phenyl]acetamide hydrochloride (or dihydrochloride)

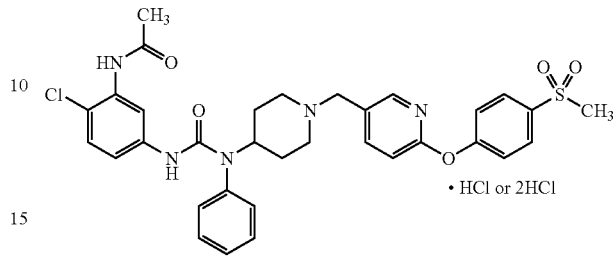

• HCl or 2HCl

To a solution of amine compound prepared by the reduction which procedure was described in Example 9 using the compound prepared in Example 7(77) (160 mg) and 1,8-diazabicyclo[5.4.0]undec-7-ene (34 µl) in tetrahydrofuran (5 ml) was added acetic acid anhydride (63 µl), and the mixture was refluxed for 4 hours. The reaction mixture was poured into water, and extracted with ethyl acetate. The organic layer was washed with water and brine, dried over anhydrous sodium sulfate, and concentrated. To a solution of the obtained residue in methanol (4 ml) was added 28% sodium methoxide in methanol solution (447 µl), stirred for 30 minutes at room temperature. The reaction mixture was concentrated, added water, and extracted with ethyl acetate. The organic layer was washed with water and brine, dried over anhydrous sodium sulfate, and concentrated. The obtained residue was purified by column chromatography on silica gel (ethyl acetate:methanol=20:1). The obtained compound was treated with 4N hydrogen chloride in ethyl acetate solution to give the title compound (89 mg) having the following physical data.

TLC: Rf 0.56 (ethyl acetate:methanol=10:1);

NMR (CD$_3$OD): δ 1.60-1.80, 2.10-2.25, 2.14, 3.14, 3.15-3.30, 3.50-3.60, 4.30, 4.70, 7.15-7.39, 7.51-7.55, 7.68, 7.96, 8.00, 8.22.

Biological Examples

It is proved by the following experiment that the compound of the present invention represented by formula (I) has the antagonistic activity against chemokine receptor, especially CCR5, and the inhibitory activity against cell migration, and also has the proper condition to be a very useful medicament.

Biological Example 1

Antagonistic Activity Test Against CCR5

It can be proved by, for example, the procedure described in JP-A-2004-256531 that the compound of the present invention has the antagonistic activity against CCR5.

Biological Example 2

Cell Migration Test

It was proved by, for example, the following experiment that the compound of the present invention has the inhibitory activity against cell migration.

Preparation of PBMC (Peripheral Blood Mononuclear Cell)

Human venous blood (50 mL) collected by using syringe with heparin sodium (final concentration: 10 U/mL, heparin sodium injection 1000 U/mL, Shimizu Pharmaceutical Co., Ltd.) was stored into 50 mL of conical tube made by polypropylene. To a Lymphoprep tube (HYCOMED PHARMA, Cat. No 1019818), 16.5 mL of DPBS (−) (GIBCO, CatNo. 14190-136) and a blood sample were added, jiggled several times, then centrifuged at 3000 rpm for 10 minutes at room temperature. About 7 mL of PBMC phase (center phase) was collected into 50 mL of conical tube made by polypropylene using a Pasteur pipette, and DPBS (−) was added to a final concentration (50 mL), than centrifuged at 1200 rpm for 10 minutes at room temperature. After removing a supernatant, residue was redissolved with 50 mL of DPBS (−). The suspension of the cell was centrifuged at 1500 rpm for 3 minutes at room temperature. The supernatant was removed, then 3 mL of hemolysis buffer (0.8% $NH_4Cl$, 0.1% $KHCO_3$, 1 mmol/L EDTA) was added thereto to suspend enough, and then left 2 minutes at room temperature. The suspension was added by 30 mL of DPBS (−), centrifuged at 1500 rpm for 3 minutes at room temperature. The supernatant was removed to give PBMC.

Culture of Human PBMC

After anti human CD3 antibody OKT3 (Janssen Pharmaceutical K.K., 1 µg/mL) coated 24 well plate overnight at 4° C., it was blocked by culture medium (RPMI 1640 (GIBCO, Cat. No. 11875-085), 10% FBS (GIBCO, Cat. No. 112318-028), 1% PSF (GIBCO, Cat. No. 15240-096)) in 30 minutes at 37° C. Prepared human PBMC was seeded into the plate coated by OKT3 ($2\times10^6$ cells/well), cultured in a few days at 37° C. PBMC was collected, and seeded into the plate uncoated by OKT3 ($2\times10^6$ cells/well) in the presence of human IL2 (5 ng/mL), then cultured. PBMC was subculture every two or three days.

Analysis of Human CCR5 Expression Using FACS

After 10 µL of FITC labeled anti human CCR5 antibody (2D7) (BD Pharmingen, Cat. No. 555992) and PE labeled anti human CD45RO antibody (BD Pharmingen, Cat. No. 347967) was added to the human PBMC cultured in $1\times10^6$ cells, the mixture was shaded 15 minutes or left 30 minutes on the ice, then DPBS (GIBCO) was added thereto and washed. The cell was suspended with 500 µL of DPBS, and then fluorescence intensity was measured by using FACS.

In Vitro Experiment of Cell Migration

50 µL of $5\times10^5$ cells of the human PBMC suspension (culture medium) and 50 µL of the solution of the test compound (0-2 µmol/L: double concentration of a final concentration) were added to an upper well of transwell (coster), and 300 µL of 60 nmol/L of the human MIP-1β (Pepro tech, Cat. No. 300-09) and 300 µL of a double concentration of the solution of the test compound were added to a lower well. It was prepared that a concentration of DMSO in upper well was 0.01%. The solution was incubated 1.5 hours in the atmosphere of carbon dioxide gas (37° C., 5% $CO_2$, degree of humidity: 95%). After the solvent of upper well was aspirated, 100 µL of 20 µmol/L of EDTA/DPBS (−) was added thereto, and incubated 30 minutes at 4° C., then centrifuged at 1500 rpm for 5 minutes. 100 µL of the solution was transferred to white 96 well plate for fluorescence from lower well by pipetting, an amount of cells was measured by using Celltiter Glo (Promega) (a measurement of ATP), Cell migration inhibition ratio was calculated by the following calculating formula. The value of $IC_{50}$ was calculated from cell migration inhibition ratio of each concentration. The value was an average value (n=3).

As a result, the compounds of the present invention showed inhibitory activity against human MIP-1β-induced cell migration of human cultured PBMC with an $IC_{50}$ value of 0.01 µM or less. For example, the compound prepared in Example 7(29) showed an $IC_{50}$ value of 0.0012 µM.

Cell migration inhibition ratio=$(Ea-Ec)/(Eb-Ec)\times100$

Ea: measured value when a test compound (0.01% in DMSO) is added

Eb: measured value when no test compound but only DMSO is added

Ec: measured value when no test compound but only DMSO is added with no added ligand to lower well

Biological Example 3

Stability Test in Liver Microsome of Monkey

It was demonstrated that the compounds of the present invention have metabolic stability by the following experiments, for example.

To a solution of 100 mmol/L phosphate buffer (pH7.4, it was prepared from 100 mmol/L of aqueous solution of dipotassium hydrogen phosphate and 100 mmol/L of aqueous solution of potassium dihydrogen phosphate.), liver microsome of monkey (final concentration: 1 mg/mL) and a test compound (final concentration: 5 µmol/L) was added and the mixture solution was pre-incubated for 5 minutes. The mixture solution was added by NADPH generating system (13 mmol/L β-$NADP^+$ (final concentration: 1.3 mmol/L), 33 mmol/L G-6-P (final concentration: 3.3 mmol/L), 10 U/mL G-6-P DH (from Yeast) (final concentration: 0.4 U/mL), and 33 mmol/L magnesium chloride solution (final concentration: 3.3 mmol/L)). While the mixture was incubated at 37° C., 100 µL of the reaction solution was taken out 0 and 30 minutes after the start, and was added to acetonitrile (2 mL) to terminate the reaction (n=2). After internal standard solution was added thereto, the mixture solution was agitated, and then centrifuged at 3000 rpm for 5 minutes. 100 µL of the resulting supernatant was mixed with 100 µL of mobile phase A, and then was analyzed by LC/MS/MS.

The condition of LC/MS/MS for analysis is outlined below.

| LC condition: | |
|---|---|
| Column: | XTerra RP8 3.5 µm (2.1 mmID × 50 mm) (Waters Corporation) |
| Temperature of column: | 40° C. |
| Mobile phase A: | 5 mmol/L aqueous ammonium acetate solution/acetonitrile (80/20, V/V) |
| Mobile phase B: | 5 mmol/L aqueous ammonium acetate solution/acetonitrile (20/80, V/V) |

-continued

| LC condition: | |
|---|---|
| Temperature of sample: | 4° C. |
| Injection volume of sample: | 5 μL |
| Time for analysis: | 10 min |

Composition of mobile phases, and Flow rate:

TABLE 1

| Time (min) | Flow rate (μL/min) | A (%) | B (%) |
|---|---|---|---|
| 0.00 | 300 | 95.0 | 5.0 |
| 1.00 | 300 | 95.0 | 5.0 |
| 1.10 | 300 | 5.0 | 95.0 |
| 5.00 | 300 | 5.0 | 95.0 |
| 5.10 | 300 | 95.0 | 5.0 |
| 10.00 | 300 | 95.0 | 5.0 |

| MS/MS condition: | |
|---|---|
| Measuring equipment: | API3000 (AB/MDS SCIEX) |
| Ionization method: | Electrospray ionization (ESI, Positive) |

The appropriate monitoring ion was selected for an each sample. For example, 647.5 (m/z) as parent ion and 277.0 (m/z) as daughter ion were selected for the compound prepared in Example 7(83).

The residual ratio of the unmetabolite (%) of the test compound in liver microsome of monkey was calculated by the following calculation formula.

The residual ratio of the unmetabolite (%) =
(a concentration of the test compound at 30 minutes)/
(a concentration of the test compound at 0 minute)×100

As a result, it was proven that the compounds of the present invention are metabolic stable in liver microsome. For example, the residual ratio of the unmetabolite of the compound prepared in Example 7(83) was 88%.

Biological Example 4

Pharmacokinetics Test in Blood in Monkey

It was demonstrated that the compounds of the present invention have a good property of pharmacokinetics in blood by the following experiments, for example.

Each of five test compounds were weighed, and dissolved in Soltol (Trademark; BASF Takeda Vitamins Ltd.)/propylene glycol=7/3 heated to 50° C. to be 5 mg/mL solution thereof. Equal amount of each five samples were weighed, mixed, and then diluted with distilled water for injection by five times to make a solution for oral administration. The solution for oral administration (1 mg/kg) was forced intragastric administering to cynomolgus monkey (male, Hamri Co., Ltd) with sonde (n=3). The administering was done in the fasting state but they have freedom to drink water. Each 1 mL of blood samples were collected from superficial cephalic vein, using a heparinized syringe, 5, 15, 30 minutes, 1, 2, 4, 6, 8 and 24 hours after administration. Collected samples were stored into ice, centrifuged at 3000 rpm for 15 minutes to get plasma. The plasma was stored at −20° C. The plasma sample stored at −20° C. was dissolved, then 100 μL of the resulting solution was added by internal standard solution and acetonitrile (2 mL), agitated, centrifuged at 3000 rpm for 10 minutes. The resulting supernatant was dried with a centrifuge concentrator. The residue was redissolved in 100 μL of mobile phase A, and then 40 μL of the resulting solution was analyzed by LC/MS/MS The condition of LC/MS/MS for analysis is outlined below.

| LC condition: | |
|---|---|
| Measuring equipment: | Waters 2790 (Waters) |
| Column: | YMC-Pack MB-ODS 5 μm (2.1 mmID × 50 mm) (YMC) |
| Temperature of column: | room temperature |
| Flow rate: | 200 μL/minute |
| Mobile Phase: | 20 mmol/L aqueous ammonium acetate solution/acetonitrile (1/1, V/V) |
| MS/MS condition: | |
| Measuring equipment: | QUATTRO Ultima (Micromass) |
| Ionization method: | ES+ |
| Capillary voltage: | 3.20 kV |
| Temperature of source: | 150° C. |
| Temperature of desolvation: | 250° C. |
| Multiplier: | 650 V |

The appropriate monitoring ion was selected for an each sample. For example, 575.64 (m/z) as parent ion and 262.07 (m/z) as daughter ion for the compound prepared in Example 6(17), and 587.20 (m/z) as parent ion and 227.12 (m/z) as daughter ion for the compound prepared in Example 7(54) were selected, respectively.

Transition of plasma concentration of the test compound in monkey was analyzed with non-compartment analytic method using WinNonlin 4.0.1 (Pharsight), and AUC was calculated.

As a result, it was proven that the compounds of the present invention have a good property of pharmacokinetics in blood. For example, the AUC of the compound prepared in Examples 6(17) and 7(54) were 226 ng·h/mL and 1150 ng·h/mL, respectively.

Biological Example 5

Measurement of Bioavailability (BA)

It was demonstrated that the compounds of the present invention have good absorption of oral preparations by the following experiments, for example.

The test compound was weighed, and dissolved in 30% HP-β-CD (Trademark; Mitsubishi Corporation) to make 1 mg/mL solution for intravenous administration. The test compound was weighed, and dissolved in Soltol (Trademark; BASF Takeda Vitamins Ltd.)/propylene glycol=7/3 heated to 50° C. to be 5 mg/mL solution thereof. Equal amount of each five samples were weighed, mixed, and then diluted with distilled water for injection by five times to make a solution for oral administration. The solution for intravenous administration (1 mg/kg) was administered to cynomolgus monkey (male, Hamri Co., Ltd) via superficial cephalic vein by single intravenous dose (n=3). The solution for oral administration (3 mg/kg) was forced intragastric administering to cynomolgus monkey (male, Hamri Co., Ltd) with sonde (n=3). The administering was done in the fasting state but they have freedom to drink water. Each 1 mL of blood samples were collected from superficial cephalic vein, using a heparinized syringe, 5, 15, 30 minutes, 1, 2, 4, 6, 8 and 24 hours after administration. Collected samples were stored into ice, centrifuged at 3000 rpm for 15 minutes to get plasma. The plasma was stored at −20° C. The plasma sample stored at −20° C. was dissolved, then 100 μL of the resulting solution was added by internal standard solution and acetonitrile (2 mL), agitated, centrifuged at 3000 rpm for 10 minutes. The residue was redissolved in 100 μL of mobile phase A, and then 40 μL of the resulting solution was analyzed by LC/MS/MS The condition of LC/MS/MS for analysis is outlined below.

| LC condition: | |
| --- | --- |
| Measuring equipment: | Waters 2790 (Waters) |
| Column: | YMC-Pack MB-ODS 5 μm (2.1 mmID × 50 mm) (YMC) |
| Temperature of column: | room temperature |
| Flow rate: | 200 μL/minute |
| Mobile phase: | 20 mmol/L aqueous ammonium acetate solution/acetonitrile (1/1) |
| MS/MS condition: | |
| Measuring equipment: | QUATTRO Ultima (Micromass) |
| Ionization method: | ES+ |
| Capillary voltage: | 3.20 kV |
| Temperature of source: | 150° C. |
| Temperature of desolvation: | 250° C. |
| Multiplier: | 650 V |

The appropriate monitoring ion was selected for an each sample. For example, 575.64 (m/z) as parent ion and 262.07 (m/z) as daughter ion (cone current: 35V, collision current: 34 eV) were selected for the compound prepared in Example 6(17).

Transition of plasma concentration of the test compound in monkey was analyzed with non-compartment analytic method using WinNonlin 4.0.1 (Pharsight), and AUC was calculated.

BA was calculated by the following calculation formula.

$$BA(\%) = (AUC_{p.o.}/Dose_{p.o.})/(AUC_{i.v.}/Dose_{i.v.}) \times 100$$

$AUC_{p.o.}$: AUC when a test compound is orally administered $Dose_{p.o.}$: amount of the compound administered orally $AUC_{i.v.}$: AUC when a test compound is intravenously administered $Dose_{i.v.}$: amount of the compound administered intravenously As a result, it was proven that the compounds of the present invention have good absorption of oral preparations. For example, a BA of the compound prepared in Example 6(17) was 42%.

Biological Example 6

Model of Renal Allotransplantation in Cynomolgus Monkeys to Evaluate Immunosuppressive Effect of the Compound of the Present Invention Cynomolgus monkeys (body weight: 3-4.5 kg) that were ABO-compatible, major histocompatibility complex (MHC)-different, more specifically, MLR miss-matched donor (male)-recipient (either sex) combinations underwent bilateral nephrectomy with subsequent implantation of an allogenic kidney from a selected donor animal. A test substance (a compound of the present invention and/or an immunosuppressant agent) was administered daily starting on Day-1 (the day before transplantation) until the day before rejection was defined. The efficacy was assessed by comparing the length of the survival of the transplanted kidney.

The compound of the present invention was administered in combination with subtherapeutic immunosuppressant agent on the market (Cyclosporine, sirolimus, and/or tacrolimus). The efficacy was demonstrated by comparing with administration of immunosuppressant agent alone.

The compound of the present invention was administered, for example, per os (PO), twice a day at a dose level of 3, 10 or 30 mg/kg.

For example, the presence of rejection was suspected if the serum creatinine levels rise. In particular, rejection of transplanted kidney was defined as an increase in the serum creatinine levels to 8 mg/dL.

As a result, the compound of the present invention showed an immunosuppressive effect in the model of renal allotransplantation in cynomolgus monkeys.

Formulation Examples

Formulation Example 1

N'-(4-fluorophenyl)-N-[1-({6-[4-(methylsulfonyl)phenoxy]pyridin-3-yl}methyl)piperidin-4-yl]-N-phenylurea hydrochloride (10 g), calcium carboxymethyl cellulose (disintegrant, 2.0 g), magnesium stearate (lubricant, 1.0 g) and microcrystalline cellulose (87 g) are admixed in a conventional manner, punched them out to give 1000 tablets each containing 10 mg of active ingredient.

Formulation Example 2

N'-(4-fluorophenyl)-N-[1-({6-[4-(methylsulfonyl)phenoxy]pyridin-3-yl}methyl)piperidin-4-yl]-N-phenylurea hydrochloride (10 g), mannitol (200 g) and distilled water (5 L) are admixed in a conventional manner. Then the solution was filtered through a dustproofing filter, and then 5 ml aliquots were charged into ampoules, which were autoclaved to give 1000 ampoules each containing 10 mg of active ingredient.

INDUSTRIAL APPLICABILITY

The compounds of the present invention represented by formula (I) has the antagonistic activity against chemokine receptor, especially CCR5, so they are useful in preventing and/or treating CCR5-related diseases, for example, various inflammatory diseases (asthma, nephritis, nephropathy, hepatitis, arthritis, rheumatoid arthritis, rhinitis, conjunctivitis, inflammatory bowel disease such as ulcerative colitis, etc.), immunological diseases (autoimmune diseases, rejection in organ transplantation (rejection of graft of solid organ, rejection of graft of pancreatic islet cells in therapy for diabetes, graft-versus-host disease, etc.), immunosuppression, psoriasis, multiple sclerosis, etc.), infectious diseases (infection with human immunodeficiency virus, acquired immunodeficiency syndrome, infection with RSV, etc.), allergic diseases (atopic dermatitis, urticaria, allergic bronchopulmonary aspergillosis, allergic eosinophilic gastroenteritis, etc.), cardiovascular diseases (arteriosclerosis, ischemic reperfusion injury, etc.), acute respiratory distress syndrome, shock accompanying bacterial infection, diabetes, cancer metastasis and so on. Therefore, chemokine receptor antagonist, especially CCR5 antagonist, is useful as medicament.

The invention claimed is:

1. A compound of 5-{[(butyl{1-[(2-methyl-6-{4-[(methylsulfonyl)amino]phenoxy}-3-pyridinyl)methyl]-4-piperidinyl}amino)carbonyl]amino}-2,4-difluorobenzamide, or a salt thereof.

2. The compound according to claim 1, wherein the salt is 5-{[(butyl {1-[(2-methyl-6-{4-[(methylsulfonyl)amino]phenoxy}-3-pyridinyl)methyl]-4-piperidinyl}amino)carbonyl] amino}-2,4-difluorobenzamide hydrochloride or 5-{[(butyl{1-[(2-methyl-6-{4-[(methylsulfonyl)amino]phenoxy}-3-pyridinyl)methyl]-4-piperidinyl}amino)carbonyl]amino}-2,4-difluorobenzamide dihydrochloride.

3. A pharmaceutical composition, which comprises the compound according to claims 1 or 2 or a salt thereof.

* * * * *

SEQUENCE LISTING

<160> NUMBER OF SEQ ID NOS: 3

<210> SEQ ID NO 1
<211> LENGTH: 37
<212> TYPE: DNA
<213> ORGANISM: Artificial
<220> FEATURE:
<223> OTHER INFORMATION: Forward primer for hCCR5Xba1

<400> SEQUENCE: 1

| agctagtcta gatccgttcc cctacaagaa actctcc | 37 |
|---|---|

<210> SEQ ID NO 2
<211> LENGTH: 37
<212> TYPE: DNA
<213> ORGANISM: Artificial
<220> FEATURE:
<223> OTHER INFORMATION: Reverse primer for hCCR5Xba1

<400> SEQUENCE: 2

| agctagtcta gagtgcacaa ctctgactgg gtcacca | 37 |
|---|---|

<210> SEQ ID NO 3
<211> LENGTH: 3383
<212> TYPE: DNA
<213> ORGANISM: Homo sapiens

<400> SEQUENCE: 3

| | |
|---|---|
| agaagagctg agacatccgt tccctacaa gaaactctcc ccgggtggaa caagatggat | 60 |
| tatcaagtgt caagtccaat ctatgacatc aattattata catcggagcc ctgccaaaaa | 120 |
| atcaatgtga agcaaatcgc agcccgcctc ctgcctccgc tctactcact ggtgttcatc | 180 |
| tttggttttg tgggcaacat gctggtcatc ctcatcctga taaactgcaa aaggctgaag | 240 |
| agcatgactg acatctacct gctcaacctg gccatctctg acctgttttt ccttcttact | 300 |
| gtccccttct gggctcacta tgctgccgcc cagtgggact tggaaatac aatgtgtcaa | 360 |
| ctcttgacag ggctctattt tataggcttc ttctctggaa tcttcttcat catcctcctg | 420 |
| acaatcgata ggtacctggc tgtcgtccat gctgtgtttg ctttaaaagc caggacggtc | 480 |
| acctttgggg tggtgacaag tgtgatcact tgggtggtgg ctgtgtttgc gtctctccca | 540 |
| ggaatcatct ttaccagatc tcaaaaagaa ggtcttcatt acacctgcag ctctcatttt | 600 |
| ccatacagtc agtatcaatt ctggaagaat ttccagacat aaagatagt catcttgggg | 660 |
| ctggtcctgc cgctgcttgt catggtcatc tgctactcgg gaatcctaaa aactctgctt | 720 |
| cggtgtcgaa atgagaagaa gaggcacagg gctgtgaggc ttatcttcac catcatgatt | 780 |
| gtttatttc tcttctgggc tccctacaac attgtccttc tctgaacac cttccaggaa | 840 |
| ttctttggcc tgaataattg cagtagctct aacaggttgg accaagctat gcaggtgaca | 900 |
| gagactcttg ggatgacgca ctgctgcatc aaccccatca tctatgcctt tgtcggggag | 960 |
| aagttcagaa actacctctt agtcttcttc caaaagcaca ttgccaaacg cttctgcaaa | 1020 |
| tgctgttcta ttttccagca agaggctccc gagcgagcaa gctcagttta cacccgatcc | 1080 |
| actggggagc aggaaatatc tgtgggcttg acacggac tcaagtgggc tggtgaccca | 1140 |
| gtcagagttg tgcacatggc ttagttttca tacacagcct gggctggggg tggggtggga | 1200 |
| gaggtctttt ttaaaaggaa gttactgtta tagagggtct aagattcatc catttatttg | 1260 |
| gcatctgttt aaagtagatt agatctttta agcccatcaa ttatagaaag ccaaatcaaa | 1320 |

-continued

```
atatgttgat gaaaaatagc aaccttttta tctccccttc acatgcatca agttattgac   1380
aaactctccc ttcactccga aagttcctta tgtatattta aaagaaagcc tcagagaatt   1440
gctgattctt gagtttagtg atctgaacag aaataccaaa attatttcag aaatgtacaa   1500
cttttttacct agtacaaggc aacatatagg ttgtaaatgt gtttaaaaca ggtctttgtc   1560
ttgctatggg gagaaaagac atgaatatga ttagtaaaga aatgacactt ttcatgtgtg   1620
atttcccctc caaggtatgg ttaataagtt tcactgactt agaaccaggc gagagacttg   1680
tggcctggga gagctgggga agcttcttaa atgagaagga atttgagttg gatcatctat   1740
tgctggcaaa gacagaagcc tcactgcaag cactgcatgg gcaagcttgg ctgtagaagg   1800
agacagagct ggttgggaag acatggggag aaggacaag gctagatcat gaagaacctt   1860
gacggcattg ctccgtctaa gtcatgagct gagcagggag atcctggttg gtgttgcaga   1920
aggtttactc tgtggccaaa ggagggtcag gaaggatgag catttagggc aaggagacca   1980
ccaacagccc tcaggtcagg gtgaggatgg cctctgctaa gctcaaggcg tgaggatggg   2040
aaggagggag gtattcgtaa ggatgggaag gagggaggta ttcgtgcagc atatgaggat   2100
gcagagtcag cagaactggg gtggatttgg tttggaagtg agggtcagag aggagtcaga   2160
gagaatccct agtcttcaag cagattggag aaacccttga aaagacatca agcacagaag   2220
gaggaggagg aggtttaggt caagaagaag atggattggt gtaaaaggat gggtctggtt   2280
tgcagagctt gaacacagtc tcacccagac tccaggctgt ctttcactga atgcttctga   2340
cttcatagat ttccttccca tcccagctga aatactgagg ggtctccagg aggagactag   2400
atttatgaat acacgaggta tgaggtctag gaacatactt cagctcacac atgagatcta   2460
ggtgaggatt gattacctag tagtcatttc atgggttgtt gggaggattc tatgaggcaa   2520
ccacaggcag catttagcac atactacaca ttcaataagc atcaaactct tagttactca   2580
ttcagggata gcactgagca aagcattgag caaaggggtc ccatataggt gagggaagcc   2640
tgaaaaacta agatgctgcc tgcccagtgc acacaagtgt aggtatcatt ttctgcattt   2700
aaccgtcaat aggcaaaggg gggaagggac atattcattt ggaataagc tgccttgagc   2760
cttaaaaccc acaaaagtac aatttaccag cctccgtatt tcagactgaa tgggggtggg   2820
gggggcgcct taggtactta ttccagatgc cttctccaga caaaccagaa gcaacagaaa   2880
aaatcgtctc tccctcccctt tgaaatgaat ataccccctta gtgtttgggt atattcattt   2940
caaagggaga gagagaggtt tttttctgtt ctttctcata tgattgtgca catacttgag   3000
actgttttga atttggggga tggctaaaac catcatagta caggtaaggt gagggaatag   3060
taagtggtga gaactactca gggaatgaag gtgtcagaat aataagaggt gctactgact   3120
ttctcagcct ctgaatatga acggtgagca ttgtggctgt cagcaggaag caacgaaggg   3180
aaatgtcttt cctttttgctc ttaagttgtg gagagtgcaa cagtagcata ggaccctacc   3240
ctctgggcca agtcaaagac attctgacat cttagtattt gcatattctt atgtatgtga   3300
aagttacaaa ttgcttgaaa gaaaatatgc atctaataaa aaacaccttc taaaataaaa   3360
aaaaaaaaaa aaaaaaaaaa aaa                                          3383
```